(12) United States Patent
Gale et al.

(10) Patent No.: US 11,400,171 B2
(45) Date of Patent: *Aug. 2, 2022

(54) MANGANESE-BASED CHELATE CONJUGATES FOR MOLECULAR MR IMAGING

(71) Applicant: The General Hospital Corporation, Boston, MA (US)

(72) Inventors: Eric M. Gale, Charlestown, MA (US); Peter Caravan, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/990,368

(22) Filed: Aug. 11, 2020

(65) Prior Publication Data

US 2021/0015948 A1 Jan. 21, 2021

Related U.S. Application Data

(63) Continuation of application No. 15/751,617, filed as application No. PCT/US2016/046874 on Aug. 12, 2016, now Pat. No. 10,835,623.

(60) Provisional application No. 62/356,732, filed on Jun. 30, 2016, provisional application No. 62/204,519, filed on Aug. 13, 2015.

(51) Int. Cl.
| | |
|---|---|
| *A61B 5/055* | (2006.01) |
| *A61K 49/08* | (2006.01) |
| *A61K 49/10* | (2006.01) |
| *A61K 49/14* | (2006.01) |
| *C07D 213/87* | (2006.01) |
| *C07D 233/58* | (2006.01) |
| *C07D 213/40* | (2006.01) |
| *C07K 7/08* | (2006.01) |
| *C07D 213/65* | (2006.01) |
| *C07D 213/80* | (2006.01) |
| *C07D 217/14* | (2006.01) |
| *C07D 235/14* | (2006.01) |
| *C07D 213/68* | (2006.01) |
| *C07K 7/06* | (2006.01) |
| *G16H 10/40* | (2018.01) |
| *C07F 13/00* | (2006.01) |

(52) U.S. Cl.
CPC .......... *A61K 49/085* (2013.01); *A61K 49/103* (2013.01); *A61K 49/14* (2013.01); *C07D 213/40* (2013.01); *C07D 213/65* (2013.01); *C07D 213/68* (2013.01); *C07D 213/80* (2013.01); *C07D 213/87* (2013.01); *C07D 217/14* (2013.01); *C07D 233/58* (2013.01); *C07D 235/14* (2013.01); *C07K 7/06* (2013.01); *C07K 7/08* (2013.01); *G16H 10/40* (2018.01); *A61K 49/101* (2013.01); *C07F 13/005* (2013.01)

(58) Field of Classification Search
None
See application file for complete search history.

(56) References Cited

U.S. PATENT DOCUMENTS

| | | | |
|---|---|---|---|
| 4,622,420 A | 11/1986 | Meares et al. | |
| 4,880,008 A | 11/1989 | Lauffer | |
| 4,889,931 A | 12/1989 | Rocklage et al. | |
| 4,899,755 A | 2/1990 | Lauffer et al. | |
| 6,022,490 A | 2/2000 | Hermant et al. | |
| 6,406,297 B1 | 6/2002 | Raymond et al. | |
| 6,515,113 B2 | 2/2003 | Raymond et al. | |
| 6,549,798 B2 | 4/2003 | Stefancik et al. | |
| 6,869,591 B2 | 3/2005 | Lanza et al. | |
| 6,916,461 B2 | 7/2005 | Platzek et al. | |
| 6,984,373 B2 | 1/2006 | Wescott et al. | |
| 6,991,775 B2 | 1/2006 | Koerner et al. | |
| 7,238,341 B2 | 7/2007 | Zhang et al. | |
| 7,412,279 B2 | 8/2008 | Weisskoff et al. | |
| 8,034,898 B2 | 10/2011 | Caravan et al. | |
| 10,835,623 B2 * | 11/2020 | Gale .................... | C07D 213/87 |
| 2002/0107443 A1 | 8/2002 | Stefancik et al. | |
| 2003/0028101 A1 | 2/2003 | Weisskoff et al. | |
| 2003/0180222 A1 | 9/2003 | Zhang et al. | |
| 2005/0261472 A1 | 11/2005 | Wescott et al. | |
| 2007/0293656 A1 | 12/2007 | Caravan et al. | |
| 2008/0227962 A1 | 9/2008 | Mazzanti | |
| 2012/0211706 A1 | 8/2012 | Kuramochi et al. | |
| 2014/0350256 A1 | 11/2014 | McKenzie | |
| 2015/0336997 A1 | 11/2015 | Caravan | |
| 2017/0057986 A1 | 3/2017 | Schwartz et al. | |

FOREIGN PATENT DOCUMENTS

| | | |
|---|---|---|
| EP | 0713139 | 5/1996 |
| JP | H04337729 A | 7/1998 |
| JP | 2003525282 A | 8/2003 |

(Continued)

OTHER PUBLICATIONS

JP Office Action in Japanese Appln. No. 2018-506981, dated Jun. 8, 2021, 6 pages (with English translation).

(Continued)

*Primary Examiner* — Michael G. Hartley
*Assistant Examiner* — Melissa J Perreira
(74) *Attorney, Agent, or Firm* — Fish & Richardson P.C.

(57) ABSTRACT

Provided herein are examples of metal chelating ligands that have high affinity for manganese. The resultant metal complexes can be used as MRI contrast agents, and can be functionalized with moieties that bind to or cause relaxivity change in the presence of biochemical targets.

45 Claims, 3 Drawing Sheets

Specification includes a Sequence Listing.

(56) References Cited

FOREIGN PATENT DOCUMENTS

| WO | WO 94/01406 | 1/1994 |
|---|---|---|
| WO | WO 96/23526 | 8/1996 |
| WO | WO 2000/060044 | 10/2000 |
| WO | WO 01/08712 | 2/2001 |
| WO | WO 01/09188 | 2/2001 |
| WO | WO 01/64660 | 9/2001 |
| WO | WO 2004/112839 | 12/2004 |
| WO | WO 2008/071679 | 6/2008 |
| WO | WO 2011/100829 | 8/2011 |
| WO | WO 2014/044916 | 3/2014 |
| WO | WO 2014/107722 | 7/2014 |
| WO | WO 2015/085005 | 6/2015 |
| WO | WO 2016/198890 | 12/2016 |

OTHER PUBLICATIONS

Burden-Gully et al., "Molecular Magnetic Resonance Imaging of Tumors with a PTPµ Targeted Contrast Agent," Transl. Oncol., 2013, 6, 329-337.
Caravan et al., "Collagen-targeted MRI contrast agent for molecular imaging of fibrosis," Angew. Chem. Int. Ed., 2007, 46: 8171.
Caravan et al., "Gadolinium(III) Chelates as MRI Contrast Agents: Structure, Dynamics, and Applications," Chem, Rev., 1999, 99:2293-2352.
CN Office Action in Chinese Appln. No. 201680054836.7, dated Aug. 5, 2020, 11 pages (with English translation).
EP Office Action in European Appln. No. 16835998.2, dated Jan. 31, 2020, 9 pages.
Extended European Search Report in Application No. 16835998.2, dated Dec. 18, 2019.
Fulmer, "NMR Chemical Shifts of Trace Impurities: Common Laboratory Solvents, Organics, and Gases in Deuterated Solvents Relevant to the Organometallic Chemist," Organometallics, 2010, 29: 2176-2179.
Gale et al., "A Manganese Alternative to Gadolinium for MRI Contrast," Journal of the American Chemical Society, Dec. 2015, 137: 15548-15557.
Gale et al., "Direct Measurement of the Mn(II) Hydration State in Metal Complexes and Metalloproteins through 17O NMR Line Widths," J. Am. Chem. Soc., 2013, 135:18600-18608.
Google Search, "Trilon B Metal Chelator," dated Sep. 15, 2019, 2 pages.
Hart. J.R., "Ethylenediaminetetraacetic Acid and Related Chelating Agents," Wiley-VCH Verlag GmbH & Co. KGaA, Weinheinn, 2005, p. 1-7.
IN Office Action in Indian Appln. No. 201847009048, dated Jan. 21, 2020, 7 pages.
International Preliminary Report on Patentability in International Application No. PCT/US2016/046874, dated Feb. 22, 2018, 7 pages.
International Search Report and Written Opinion dated Dec. 28, 2016 in International Application No. PCT/US2016/046874, 13 pgs.
Jastrzebska et al., "New enzyme-activated solubility-switchable contrast agent for magnetic resonance imaging: from synthesis to in vivo imaging," J. Med. Chem., Mar. 2009, 52: 1576-1581.
JP Office Action in Japanese Appln. No. 2018-506981, dated Jul. 13, 2020, 6 pages (with English translation).
Kolodziej et al., "Fibrin specific peptides derived by phage display: characterization of peptides and conjugates for imaging," Bioconjugate Chem, Mar. 2012, 23: 548-56.
Kuźnik et al., "A new class of bioactivable self-immolative N,O-ligands," European Journal of Medicinal Chemistry, 2012, 52:184-192.
Lauffer, "Paramagnetic metal complexes as water proton relaxation agents for NMR imaging: theory and design," Chem. Rev, 1987, 87: 901-27.
Ledesma et al., "A new mononuclear manganese (III) complex of an unsvmmetrical hexadentate $N_3O_3$ ligand exhibiting superoxide dismutase and catalase-like activity: synthesis, characterization, properties and kinetics studies," Journal of Inorganic Biochemistry, 146:69-76.
Mulder et al., "Lipid-based nanoparticles for contrast-enhanced MRI and molecular imaging," NMR Biomed, 2006, 19:142-64.
Mummert et al., "Development of a peptide inhibitor of hvaluronan-mediated leukocyte trafficking," Sep. 2000, 192: 769-779.
Nicolle et al., "From monomers to micelles: investigation of the parameters influencing proton relaxtyity," J. Biol. Inorg, Chem., 2002, 7:757-69.
Nielsen et al., "Identification of a major heparin and cell binding site in the LG4 module of the laminin alpha 5 chain," J. Biol. Chem, May 2000, 275: 14517-14523.
Overoye-Chan et al., "EP-2104R: a fibrin-specific gadolinium-Based MRI contrast agent for detection of thrombus," J. Am. Chem. Soc., May 2008, 130: 6025-39.
Shazeeb et al., "A novel paramagnetic substrate for detecting myeloperoxidase activity in vivo," Mol. Imaging, 2012, 11: 433-443.
Tamura et al., "Synthesis and superoxide dismutase activity of novel iron complexes," Journal of Organometallic Chemistry, Oct. 2000, 611(1-2):586-592.
Zhou et al., "MRI detection of breast cancermicrometastases with a fibronectin-targeting contrast agent," Nat. Commun, 2015, 6: 7984-7994.
CN Office Action in Chinese Appln. No. 201680054836.7, dated Mar. 16, 2021, 19 pages (with English translation).
EP Office Action in European Appln. No. 16835998.2, dated Mar. 17, 2021, 5 pages.
IN Office Action in Indian Appln. No. 202048031267, dated Feb. 16, 2021, 6 pages.
Barnett et al., "Tumour localization using monoclonal antibodies H. Biodistribution of A5B7/111 indium chelates," Int. J. Cancer, Jan. 1988, 41(3):34-37.
Di Giovanni et al., "Dinuclear Cobalt Complexes with a Decdentate Ligand Scaffold: Hydrogen Evolution and Oxygen Reduction Catalysis," Chemistry, Jan. 2016, 22(1):361-369.
Office Action in European Appln. No. 16835998.2, dated Feb. 10, 2022, 6 pages.
Tomer et al., "Zinc Complexes of Sequential Tetradentate Monoanionic Ligands in the Isoselective Polymerization of rac-Lactide," Chemistiy, Aug. 2016, 22(33):11533-11536.
CN Office Action in Chinese Appln. No. 201680054836.7, dated Aug. 20, 2021, 14 pages (with English translation).

* cited by examiner

SEQUENCE LISTING

```
<160> NUMBER OF SEQ ID NOS: 18

<210> SEQ ID NO 1
<211> LENGTH: 6
<212> TYPE: PRT
<213> ORGANISM: Artificial
<220> FEATURE:
<223> OTHER INFORMATION: Fibrin-binding peptide
<220> FEATURE:
<221> NAME/KEY: VARIANT
<222> LOCATION: (2)..(2)
<223> OTHER INFORMATION: Xaa = proline or its derivative
      4-hydroxyproline
<220> FEATURE:
<221> NAME/KEY: VARIANT
<222> LOCATION: (3)..(3)
<223> OTHER INFORMATION: Xaa = tyrosine or its non-natural derivative
      substituted at the 3-position with a moiety from the group of F,
      Cl, Br, I, or NO2
<220> FEATURE:
<221> NAME/KEY: VARIANT
<222> LOCATION: (4)..(4)
<223> OTHER INFORMATION: Xaa = glycine or D- or L-aspartic acid

<400> SEQUENCE: 1

Cys Xaa Xaa Xaa Leu Cys
1               5
```

```
<210> SEQ ID NO 2
<211> LENGTH: 11
<212> TYPE: PRT
<213> ORGANISM: Artificial
<220> FEATURE:
<223> OTHER INFORMATION: Fibrin-binding peptide
<220> FEATURE:
<221> NAME/KEY: VARIANT
<222> LOCATION: (1)..(1)
<223> OTHER INFORMATION: Xaa = selected from W, S, F, Y, or substituted
      Y or substituted F
<220> FEATURE:
<221> NAME/KEY: VARIANT
<222> LOCATION: (2)..(2)
<223> OTHER INFORMATION: Xaa = selected from E, H, dH, S
<220> FEATURE:
<221> NAME/KEY: VARIANT
<222> LOCATION: (4)..(4)
<223> OTHER INFORMATION: Xaa = proline or its derivative
      4-hydroxyproline
<220> FEATURE:
<221> NAME/KEY: VARIANT
<222> LOCATION: (5)..(5)
<223> OTHER INFORMATION: Xaa = tyrosine or its non-natural derivative
      substituted at the 3-position with a moiety from the group of F,
      Cl, Br, I, or NO2
<220> FEATURE:
<221> NAME/KEY: VARIANT
<222> LOCATION: (6)..(6)
<223> OTHER INFORMATION: Xaa = selected from G, D, dD
<220> FEATURE:
<221> NAME/KEY: VARIANT
<222> LOCATION: (9)..(9)
<223> OTHER INFORMATION: Xaa = selected from H, F, Y, and W
<220> FEATURE:
<221> NAME/KEY: VARIANT
<222> LOCATION: (10)..(10)
<223> OTHER INFORMATION: Xaa = selected from I, L, V, and N
<220> FEATURE:
<221> NAME/KEY: VARIANT
<222> LOCATION: (11)..(11)
<223> OTHER INFORMATION: Xaa = selected from N, Q, I, L, V, or X6 is not
      present

<400> SEQUENCE: 2

Xaa Xaa Cys Xaa Xaa Xaa Leu Cys Xaa Xaa Xaa
1               5                   10

<210> SEQ ID NO 3
<211> LENGTH: 12
<212> TYPE: PRT
<213> ORGANISM: Artificial
<220> FEATURE:
<223> OTHER INFORMATION: Hyaluronic acid-binding peptide

<400> SEQUENCE: 3

Gly Ala His Trp Gln Phe Asn Ala Leu Thr Val Arg
1               5                   10

<210> SEQ ID NO 4
<211> LENGTH: 12
<212> TYPE: PRT
<213> ORGANISM: Artificial
<220> FEATURE:
<223> OTHER INFORMATION: Hyaluronic acid-binding peptide

<400> SEQUENCE: 4

Thr Ser Tyr Gly Arg Pro Ala Leu Leu Pro Ala Ala
1               5                   10

<210> SEQ ID NO 5
```

```
<211> LENGTH: 13
<212> TYPE: PRT
<213> ORGANISM: Artificial
<220> FEATURE:
<223> OTHER INFORMATION: Hyaluronic acid-binding peptide

<400> SEQUENCE: 5

Met Asp His Leu Ala Pro Thr Arg Phe Arg Pro Ala Ile
1               5                   10

<210> SEQ ID NO 6
<211> LENGTH: 12
<212> TYPE: PRT
<213> ORGANISM: Artificial
<220> FEATURE:
<223> OTHER INFORMATION: Hyaluronic acid-binding peptide

<400> SEQUENCE: 6

Thr Leu Arg Ala Ile Trp Pro Met Trp Met Ser Ser
1               5                   10

<210> SEQ ID NO 7
<211> LENGTH: 12
<212> TYPE: PRT
<213> ORGANISM: Artificial
<220> FEATURE:
<223> OTHER INFORMATION: Hyaluronic acid-binding peptide

<400> SEQUENCE: 7

Ile Pro Leu Thr Ala Asn Tyr Gln Gly Asp Phe Thr
1               5                   10

<210> SEQ ID NO 8
<211> LENGTH: 12
<212> TYPE: PRT
<213> ORGANISM: Artificial
<220> FEATURE:
<223> OTHER INFORMATION: Heparin-binding peptide

<400> SEQUENCE: 8

Ala Cys Gln Trp His Arg Val Ser Val Arg Trp Gly
1               5                   10

<210> SEQ ID NO 9
<211> LENGTH: 8
<212> TYPE: PRT
<213> ORGANISM: Artificial
<220> FEATURE:
<223> OTHER INFORMATION: Heparin sulfate/heparin interacting protein
      sequence motif
<220> FEATURE:
<221> NAME/KEY: VARIANT
<222> LOCATION: (1)..(1)
<223> OTHER INFORMATION: Xaa = non-acidic residue
<220> FEATURE:
<221> NAME/KEY: VARIANT
<222> LOCATION: (2)..(3)
<223> OTHER INFORMATION: Xaa = basic residue
<220> FEATURE:
<221> NAME/KEY: VARIANT
<222> LOCATION: (4)..(6)
<223> OTHER INFORMATION: Xaa = non-acidic residue
<220> FEATURE:
<221> NAME/KEY: VARIANT
<222> LOCATION: (7)..(7)
<223> OTHER INFORMATION: Xaa = basic residue
<220> FEATURE:
<221> NAME/KEY: VARIANT
<222> LOCATION: (8)..(8)
<223> OTHER INFORMATION: Xaa = non-acidic residue
```

```
<400> SEQUENCE: 9

Xaa Xaa Xaa Xaa Xaa Xaa Xaa Xaa
1               5

<210> SEQ ID NO 10
<211> LENGTH: 21
<212> TYPE: PRT
<213> ORGANISM: Artificial
<220> FEATURE:
<223> OTHER INFORMATION: Lesion-targeting peptide

<400> SEQUENCE: 10

Cys Gly Glu Gly Asp Asp Phe Asn Trp Glu Gln Val Asn Thr Leu Thr
1               5                   10                  15

Lys Pro Thr Ser Asp
            20

<210> SEQ ID NO 11
<211> LENGTH: 5
<212> TYPE: PRT
<213> ORGANISM: Artificial
<220> FEATURE:
<223> OTHER INFORMATION: Lesion-targeting peptide

<400> SEQUENCE: 11

Cys Arg Glu Lys Ala
1               5

<210> SEQ ID NO 12
<211> LENGTH: 10
<212> TYPE: PRT
<213> ORGANISM: Artificial
<220> FEATURE:
<223> OTHER INFORMATION: Collagen-targeting peptide
<220> FEATURE:
<221> NAME/KEY: VARIANT
<222> LOCATION: (1)..(1)
<223> OTHER INFORMATION: Xaa = can be W, C, or A
<220> FEATURE:
<221> NAME/KEY: VARIANT
<222> LOCATION: (2)..(2)
<223> OTHER INFORMATION: Xaa = can be R, C, or A
<220> FEATURE:
<221> NAME/KEY: VARIANT
<222> LOCATION: (3)..(3)
<223> OTHER INFORMATION: Xaa = can be E, C, A, K, or T
<220> FEATURE:
<221> NAME/KEY: VARIANT
<222> LOCATION: (4)..(4)
<223> OTHER INFORMATION: Xaa = can be P, C, or A
<220> FEATURE:
<221> NAME/KEY: VARIANT
<222> LOCATION: (5)..(5)
<223> OTHER INFORMATION: Xaa = can be D, G, S, C, or A
<220> FEATURE:
<221> NAME/KEY: VARIANT
<222> LOCATION: (6)..(6)
<223> OTHER INFORMATION: Xaa = can be F, R, C, or A
<220> FEATURE:
<221> NAME/KEY: VARIANT
<222> LOCATION: (7)..(7)
<223> OTHER INFORMATION: Xaa = can be C, M, or A
<220> FEATURE:
<221> NAME/KEY: VARIANT
<222> LOCATION: (8)..(8)
<223> OTHER INFORMATION: Xaa = can be A, E, or C
<220> FEATURE:
<221> NAME/KEY: VARIANT
<222> LOCATION: (9)..(9)
<223> OTHER INFORMATION: Xaa = can be L, M, R, C, or A
<220> FEATURE:
<221> NAME/KEY: VARIANT
```

<222> LOCATION: (10)..(10)
<223> OTHER INFORMATION: Xaa = can be S, N, G, L, C, or A

<400> SEQUENCE: 12

Xaa Xaa Xaa Xaa Xaa Xaa Xaa Xaa Xaa Xaa
1               5                   10

<210> SEQ ID NO 13
<211> LENGTH: 10
<212> TYPE: PRT
<213> ORGANISM: Artificial
<220> FEATURE:
<223> OTHER INFORMATION: Collagen-targeting peptide

<400> SEQUENCE: 13

Trp Arg Glu Pro Ser Phe Cys Ala Leu Ser
1               5                   10

<210> SEQ ID NO 14
<211> LENGTH: 10
<212> TYPE: PRT
<213> ORGANISM: Artificial
<220> FEATURE:
<223> OTHER INFORMATION: Collagen-targeting peptide

<400> SEQUENCE: 14

Trp Arg Glu Pro Ser Phe Met Ala Leu Ser
1               5                   10

<210> SEQ ID NO 15
<211> LENGTH: 10
<212> TYPE: PRT
<213> ORGANISM: Artificial
<220> FEATURE:
<223> OTHER INFORMATION: Collagen-targeting peptide

<400> SEQUENCE: 15

Trp Arg Glu Pro Gly Phe Cys Ala Leu Ser
1               5                   10

<210> SEQ ID NO 16
<211> LENGTH: 13
<212> TYPE: PRT
<213> ORGANISM: Artificial
<220> FEATURE:
<223> OTHER INFORMATION: Collagen-targeting peptide
<220> FEATURE:
<221> NAME/KEY: VARIANT
<222> LOCATION: (1)..(1)
<223> OTHER INFORMATION: Xaa = can be W, C, or A
<220> FEATURE:
<221> NAME/KEY: VARIANT
<222> LOCATION: (2)..(2)
<223> OTHER INFORMATION: Xaa = can be R, C, or A
<220> FEATURE:
<221> NAME/KEY: VARIANT
<222> LOCATION: (3)..(3)
<223> OTHER INFORMATION: Xaa = can be E, C, A, K, or T
<220> FEATURE:
<221> NAME/KEY: VARIANT
<222> LOCATION: (4)..(4)
<223> OTHER INFORMATION: Xaa = can be P, C, or A
<220> FEATURE:
<221> NAME/KEY: VARIANT
<222> LOCATION: (5)..(5)
<223> OTHER INFORMATION: Xaa = can be D, G, S, C, or A
<220> FEATURE:
<221> NAME/KEY: VARIANT
<222> LOCATION: (6)..(6)
<223> OTHER INFORMATION: Xaa = can be F, R, C, or A
<220> FEATURE:

```
<221> NAME/KEY: VARIANT
<222> LOCATION: (7)..(7)
<223> OTHER INFORMATION: Xaa = can be C, M, or A
<220> FEATURE:
<221> NAME/KEY: VARIANT
<222> LOCATION: (8)..(8)
<223> OTHER INFORMATION: Xaa = can be A, E, or C
<220> FEATURE:
<221> NAME/KEY: VARIANT
<222> LOCATION: (9)..(9)
<223> OTHER INFORMATION: Xaa = can be L, M, R, C, or A
<220> FEATURE:
<221> NAME/KEY: VARIANT
<222> LOCATION: (10)..(10)
<223> OTHER INFORMATION: Xaa = can be S, N, G, L, C, or A
<220> FEATURE:
<221> NAME/KEY: VARIANT
<222> LOCATION: (11)..(11)
<223> OTHER INFORMATION: Xaa = can be C, M, or A
<220> FEATURE:
<221> NAME/KEY: VARIANT
<222> LOCATION: (12)..(12)
<223> OTHER INFORMATION: Xaa = can be P, A, or C
<220> FEATURE:
<221> NAME/KEY: VARIANT
<222> LOCATION: (13)..(13)
<223> OTHER INFORMATION: Xaa = can be K, Q, P, H, G, C, or A

<400> SEQUENCE: 16

Xaa Xaa Xaa Xaa Xaa Xaa Xaa Xaa Xaa Xaa Xaa Xaa Xaa
1               5                   10

<210> SEQ ID NO 17
<211> LENGTH: 15
<212> TYPE: PRT
<213> ORGANISM: Artificial
<220> FEATURE:
<223> OTHER INFORMATION: Collagen-targeting peptide
<220> FEATURE:
<221> NAME/KEY: VARIANT
<222> LOCATION: (1)..(1)
<223> OTHER INFORMATION: Xaa = can be V, I, C, or A
<220> FEATURE:
<221> NAME/KEY: VARIANT
<222> LOCATION: (2)..(2)
<223> OTHER INFORMATION: Xaa = can be A, G, R, D, or C
<220> FEATURE:
<221> NAME/KEY: VARIANT
<222> LOCATION: (3)..(3)
<223> OTHER INFORMATION: Xaa = can be W, C, or A
<220> FEATURE:
<221> NAME/KEY: VARIANT
<222> LOCATION: (4)..(4)
<223> OTHER INFORMATION: Xaa = can be R, C, or A
<220> FEATURE:
<221> NAME/KEY: VARIANT
<222> LOCATION: (5)..(5)
<223> OTHER INFORMATION: Xaa = can be E, C, A, K, or T
<220> FEATURE:
<221> NAME/KEY: VARIANT
<222> LOCATION: (6)..(6)
<223> OTHER INFORMATION: Xaa = can be P, C, or A
<220> FEATURE:
<221> NAME/KEY: VARIAN
<222> LOCATION: (7)..(7)
<223> OTHER INFORMATION: Xaa = can be D, G, S, C, or A
<220> FEATURE:
<221> NAME/KEY: VARIANT
<222> LOCATION: (8)..(8)
<223> OTHER INFORMATION: Xaa = can be F, R, C, or A
<220> FEATURE:
<221> NAME/KEY: VARIANT
<222> LOCATION: (9)..(9)
<223> OTHER INFORMATION: Xaa = can be C, M, or A
<220> FEATURE:
<221> NAME/KEY: VARIANT
<222> LOCATION: (10)..(10)
```

```
<223> OTHER INFORMATION: Xaa = can be E, A, or C
<220> FEATURE:
<221> NAME/KEY: VARIANT
<222> LOCATION: (11)..(11)
<223> OTHER INFORMATION: Xaa = can be L, C, A, M, or R
<220> FEATURE:
<221> NAME/KEY: VARIANT
<222> LOCATION: (12)..(12)
<223> OTHER INFORMATION: Xaa = can be S, C, A, N, G, or L
<220> FEATURE:
<221> NAME/KEY: VARIANT
<222> LOCATION: (13)..(13)
<223> OTHER INFORMATION: Xaa = can be C, M, or A
<220> FEATURE:
<221> NAME/KEY: VARIANT
<222> LOCATION: (14)..(14)
<223> OTHER INFORMATION: Xaa = can be P, A, or C
<220> FEATURE:
<221> NAME/KEY: VARIANT
<222> LOCATION: (15)..(15)
<223> OTHER INFORMATION: Xaa = can be K, Q, P, H, G, C, or A

<400> SEQUENCE: 17

Xaa Xaa Xaa Xaa Xaa Xaa Xaa Xaa Xaa Xaa Xaa Xaa Xaa Xaa Xaa
1               5                   10                  15

<210> SEQ ID NO 18
<211> LENGTH: 12
<212> TYPE: PRT
<213> ORGANISM: Artificial
<220> FEATURE:
<223> OTHER INFORMATION: Collagen-targeting peptide
<220> FEATURE:
<221> NAME/KEY: VARIANT
<222> LOCATION: (4)..(4)
<223> OTHER INFORMATION: Xaa = selected from Y, T, or S
<220> FEATURE:
<221> NAME/KEY: VARIANT
<222> LOCATION: (6)..(6)
<223> OTHER INFORMATION: Xaa = can be any amino acid

<400> SEQUENCE: 18

Trp His Cys Xaa Thr Xaa Phe Pro His His Tyr Cys
1               5                   10
```

MANGANESE-BASED CHELATE CONJUGATES FOR MOLECULAR MR IMAGING

CROSS-REFERENCE TO RELATED APPLICATIONS

This application is a continuation of U.S. application Ser. No. 15/751,617, filed on Feb. 9, 2018, which is a § 371 National Stage Application of PCT/US2016/046874, filed Aug. 12, 2016, which claims priority to U.S. Provisional Application Ser. No. 62/204,519, filed on Aug. 13, 2015, and U.S. Provisional Application Ser. No. 62/356,732, filed on Jun. 30, 2016, the contents of each of which are herein incorporated by reference in their entireties.

FEDERALLY SPONSORED RESEARCH OR DEVELOPMENT

This invention was made with Government support under Grant No. R01 CA161221 awarded by the National Institutes of Health. The Government has certain rights in the invention.

TECHNICAL FIELD

This invention relates to metal chelating ligands, and more particularly to manganese chelate complexes of these ligands that can be used as contrast agents for magnetic resonance imaging.

BACKGROUND

Many the metal chelating ligands currently used in magnetic resonance (MR) are polyaminopolycarboxylate metal binding chelating ligands designed for chelation of lanthanide(III) ions like gadolinium(III). All commercially available MR contrast formulations contain metal-chelate compounds of gadolinium(III). However, the last decade has seen a rise in awareness of gadolinium(III) induced toxicity in patients receiving gadolinium(III) containing MR contrast formulations. This toxicity is manifested as nephrogenic systemic fibrosis (NSF). Patients experiencing chronic kidney disease are particularly susceptible to gadolinium(II) induced NSF, and MR contrast formulations are generally not administered to patients suffering severe chronic kidney disease. To avoid the potential for gadolinium(III) associated toxicity, it would therefore be useful to identify MR contrast agents that do not contain gadolinium(III).

An effective contrast agent must contain several features. It should have high relaxivity to generate image contrast. Relaxivity is the ability of the metal chelate to relax water protons, and is defined as the change in the relaxation rate of water divided by the millimolar concentration of the chelate. Relaxivity depends on many molecular factors. For high relaxivity, it is advantageous to use a metal ion with a high spin quantum number; it is advantageous to have one or more water molecules directly bonded to the metal ion; and the bonded water molecule should undergo very fast chemical exchange with other water molecules in the solvent. Most metal ions are toxic at the concentrations required to provide MR contrast. Therefore the metal ion should be chelated by a multidentate ligand with sufficient stability to prevent the metal ion from being released in the body in significant amounts.

It would also be valuable to identify metal chelating ligands that form high-relaxivity compounds that either bind to, or change relaxivity, in the presence of biochemical targets. Compounds that bind to biochemical targets would enable detection of the targeted protein, enzyme, or cell at a delayed phase, after the compound in unbound form has been cleared via excretion. Compounds that change relaxivity in the presence of biochemical target will provide a change in MRI signal intensity at the locus of the target. The ability to detect change in biochemical processes with MRI would provide a non-invasive means to stage or monitor the progression of disease states such as cancer, inflammation, fibrosis, and thrombosis. Such compounds and imaging methods would also provide a non-invasive means to track therapeutic response.

SUMMARY

This disclosure is based on one or more modifications of a chelating ligand to either bind to a biochemical target, or enhance the relaxivity of a resultant metal chelate in the presence of a biochemical target, or to provide additional stability of a resultant metal chelate to prevent metal ion dissociation in the body. These modifications include changing the donor groups (functional groups that directly coordinate to the metal ion), introducing groups that organize water in the second coordination sphere (e.g., by hydrogen bonding), introducing groups that facilitate water exchange on and off the metal ion, introducing groups that slow down molecular tumbling either by increased molecular weight or by targeting the metal chelate to a macromolecule (e.g., a protein), and introducing groups that support or promote a change in metal oxidation state. The donor groups can include a number of functionalities to exploit high relaxivity mechanisms, including, by way of example, enhancing relaxivity via binding to a macromolecular target, or changing oxidation state in response to enzyme activity.

Metal chelates prepared with the chelating ligands can be examined with techniques including relaxivity measurements at different magnetic fields and temperatures, and variable temperature $^{17}O$ NMR measurements.

Finally, chelating ligands may be useful for preparing diagnostic and/or therapeutic compositions of radioactive metal ions.

Provided herein is a compound of Formula (I):

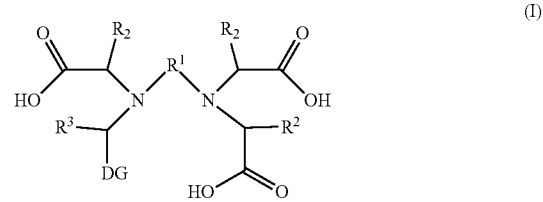

or a pharmaceutically acceptable salt thereof,
wherein:
$R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl)$(C_6$-$C_{10}$ aryl ene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;

each R² and R³ is independently selected from the group consisting of H, CO₂H, (C₁-C₆ alkyl)CO₂H, C₁-C₆ alkyl, C₂-C₆ alkenyl, C₂-C₆ alkynyl, C₄-C₆ cycloalkyl, aryl, 5-6 membered heterocyclyl, 5-6 membered heteroaryl, C(O)NR⁴R⁵, CH₂NHCOR⁴, C(O)N(OH)R⁴, C(O)NHSO₂R⁴, CH₂NHSO₂R⁴, N(OH)C(O)R⁴, P(R⁴)O₂R⁵, PO₃R⁴R⁵, and [L]-[TBM];

each R⁴ and R⁵ is independently selected from the group consisting of H, C₁-C₆ alkyl, and [L]-[TBM], wherein the alkyl is optionally substituted by 1, 2, 3, or 4 independently selected R$^X$ groups;

DG is selected from the group consisting of:

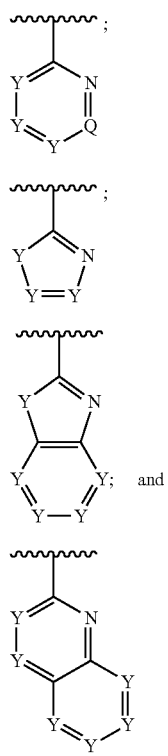

or any constitutional isomers of Formulas IV and V, wherein each Y is independently CH, CZ, N, O, S or NR⁴;
Q is CH, CZ, N, O, S or NR⁴;
each Z is independently selected from the group consisting of H, OH, OR⁴, CO₂R⁴, —(C₁₋₆ alkyl)CO₂H, C₁-C₆ alkyl, C₂-C₆ alkenyl, C₂-C₆ alkynyl, C₄-C₆ cycloalkyl, C₆-C₁₀ aryl, 5-6 membered heterocyclyl, 5-6 membered heteroaryl, C(O)NR⁴R⁵, CH₂NHCOR⁴, C(O)N(OH)R⁴, C(O)NHSO₂R⁴, CH₂NHSO₂R⁴, N(OH)C(O)R⁴, P(R⁴)O₂R⁵, PO₃R⁴R⁵, and -[L]-[TBM], wherein the alkyl, alkenyl, alkynyl, cycloalkyl, heterocycloalkyl, aryl, and heteroaryl are each optionally substituted by 1, 2, 3, or 4 independently selected R$^X$ groups;
L is a linker;
TBM is a target binding moiety; and
each R$^X$ is independently selected from the group consisting of OH, SH, CN, NO₂, halo, pseudohalo, amino, thionyl, sulfinyl, sulfonyl, sulfa, C₁-C₄ alkyl, C₂-C₄ alkenyl, C₂-C₄ alkynyl, C₁-C₄ haloalkyl, C₁-C₄ cyanoalkyl, C₁-C₄ hydroxyalkyl, alkoxy, C₁-C₄ aminoalkyl, di(C₁-C₄ alkyl) amino, C₁-C₄ alkylamine, phosphinate, phosphinate ester, phosphonate, phosphonate ester, phosphodiester, C₁₋₄ alkylphosphodiester, C₃-C₆ cycloalkyl, phenyl, 5-6 membered heteroaryl, 5-6 membered heterocycloalkyl, (C₁-C₄ alkyl)phenyl, and -[L]-[TBM];

wherein if Q is CH or CCOOH and all Y are CH, than at least one of R² or R³ is not H.

In some embodiments, DG is:

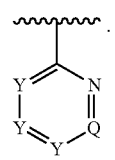

In some embodiments, Q is CH. In some embodiments, Y is CH. In some embodiments, at least one Y is CZ, wherein Z is selected from the group consisting of CO₂R⁴, C₁-C₆ alkyl, and OR⁴. In some embodiments, one Y is CZ, wherein Z is selected from the group consisting of CO₂R⁴, C₁-C₆ alkyl, and OR⁴, and all other Y are CH. In some embodiments, each R⁴ is H or C₁-C₆ alkyl, wherein the alkyl is optionally substituted by 1, 2, 3, or 4 OH groups.

In some embodiments, R² and R³ is H.

In some embodiments, DG is selected from the group consisting of:

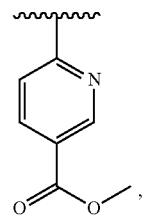 [SMILES: *c1ccc(C(=O)OC)cn1]

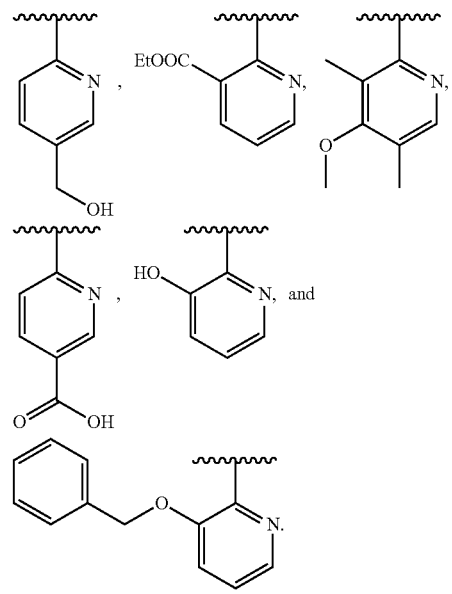

In some embodiments, DG is

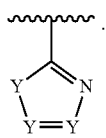  (III)

For example, wherein at least one Y is N, O, S or NR⁴. In some embodiments, one Y is NR⁴ and the remaining Y are CH. For example, DG is selected from the group consisting of:

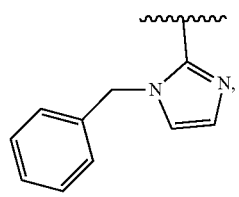

In some embodiments, DG is:

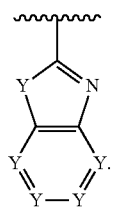  (IV)

In some embodiments, at least one Y is N, O, S or NR⁴. For example, one Y is NR⁴ and the remaining Y are CH. In some embodiments, DG is:

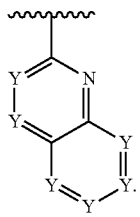  (V)

In some embodiments, DG is:

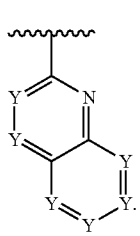  (V)

For example, DG is:

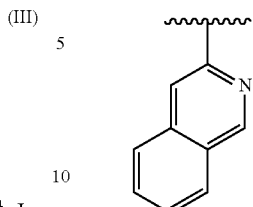

In some embodiments, $R^1$ is $C_3$-$C_{10}$ cycloalkylene. For example, $R^1$ is a $C_6$ cycloalkylene. In some embodiments, $R^1$ is:

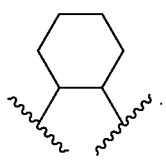 [SMILES: *C1CCCCC1*]

In some embodiments, $R^1$ is a $C_1$-$C_6$ alkylene. For example, $R^1$ is a $C_2$ alkylene. In some embodiments, $R^1$ is:

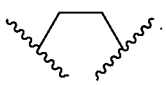

In some embodiments, $R^2$ is H.

In some embodiments, $R^3$ is H.

In some embodiments, the compound of Formula (I) is selected from the group consisting of:

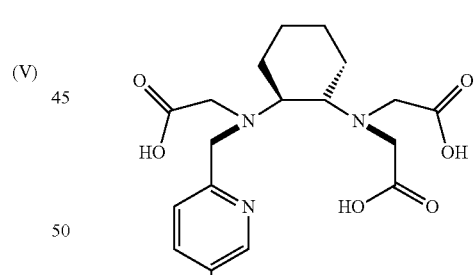

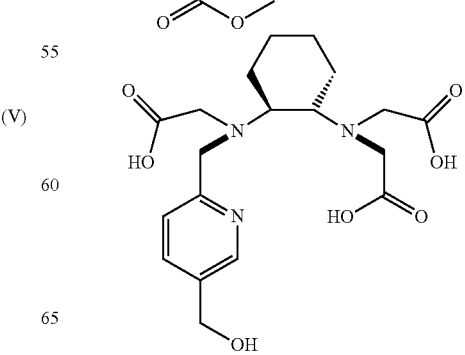

-continued

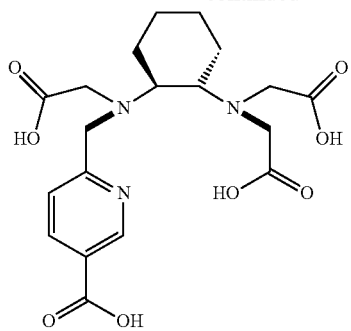

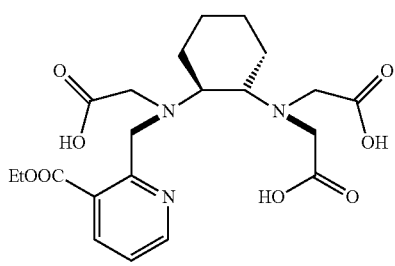

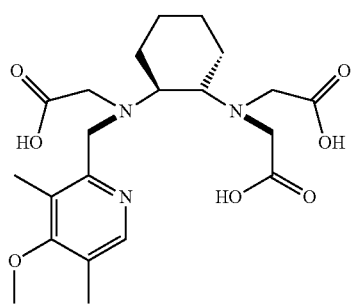

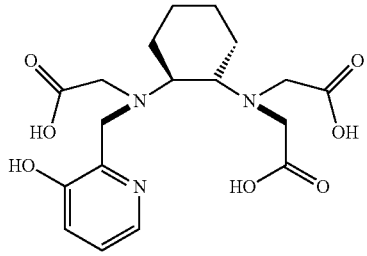

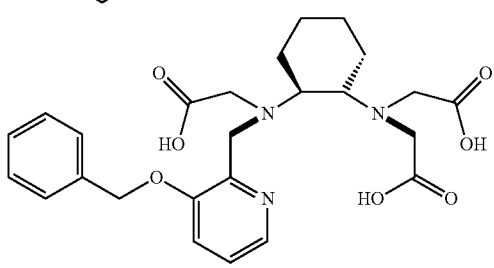

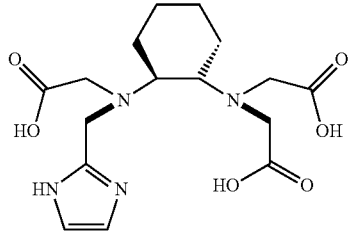

-continued

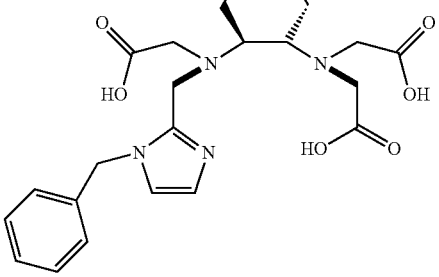

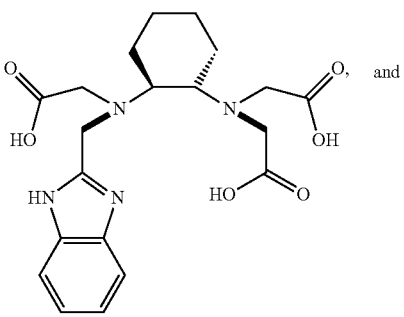

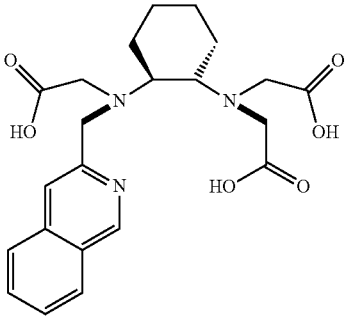

or a pharmaceutically acceptable salt thereof.

Also provided herein are compounds of Formula (VI):

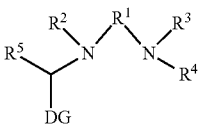

(VI)

or a pharmaceutically acceptable salt thereof;
wherein:
$R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl)$(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^x$ groups, and wherein $R^1$ is bound to the adjacent nitrogens via the 1,2 or 1,3 positions on $R^1$;

$R^2$, $R^3$, and $R^4$ are independently selected from the group of compounds of formula:

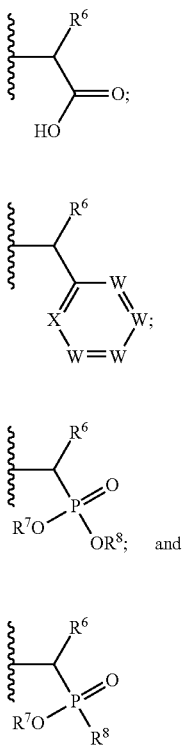

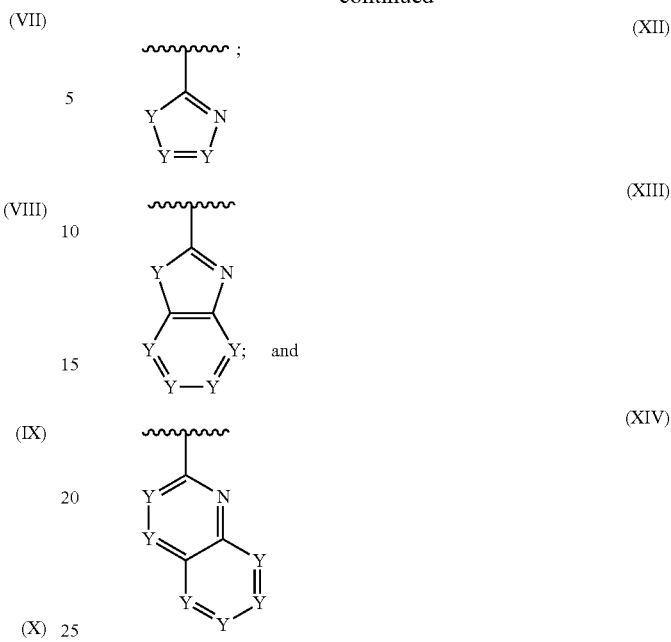

or any constitutional isomers of Formulas XIII-XIV, wherein each Y is independently CH, $CZ^1$, N, O, S, or $NR^7$;

Q is independently CH, $CZ^1$, N, O, S, or $NR^7$;

each $Z^1$ is independently selected from H, OH, $OR^4$, $CO_2H$, —($C_{1-6}$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, $PO_3R^4R^5$, and -[L]-[TBM], wherein the alkyl, alkenyl, alkynyl cycloalkyl, heterocycloalkyl, aryl, and heteroaryl are each optionally substituted by 1, 2, or 4 independently selected $R^X$ groups;

L is a linker;

TBM is a target binding moiety; and each $R^X$ is independently selected from the group consisting of OH, SH, CN, $NO_2$, halo, pseudohalo, amino, thionyl, sulfinyl, sulfonyl, sulfo, $C_1$-$C_4$ alkyl, $C_2$-$C_4$ alkenyl, $C_2$-$C_4$ alkynyl, $C_1$-$C_4$ haloalkyl, $C_1$-$C_4$ cyanoalkyl, $C_1$-$C_4$ hydroxyalkyl, $C_1$-$C_4$ alkoxy, $C_1$-$C_4$ aminoalkyl, di($C_1$-$C_4$ alkyl)amino, $C_1$-$C_4$ alkylamine, phosphinate, phosphinate ester, phosphonate, phosphonate ester, phosphodiester, $C_{1-4}$ alkylphosphodiester, $C_3$-$C_6$ cycloalkyl, phenyl, 5-6 membered heteroaryl, 5-6 membered heterocycloalkyl, ($C_1$-$C_4$ alkyl)phenyl, and -[L]-[TBM];

wherein if Q is CH or CCOOH, all Y are CH, and all of $R^2$, R, and $R^4$ are formula VII, than at least one of $R^5$ or $R^6$ is not H; and if one of $R^2$, $R^3$, or $R^4$ is formula VIII, and all of $R^5$ and $R^6$ are H, than the aromatic ring component of formula VIII (i.e. the ring containing X and W) must be different than DG.

In some embodiments, $R^1$ is 1,2-cyclohexylene, $R^2$, $R^3$, and $R^4$ are formula VII, $R^5$ and $R^6$ are H, and DG is formula XI and one Y is [L]-[TBM], where [L] is —C(O)— and [TBM] is —$NHNH_2$.

$R^5$ and $R^6$ are independently selected from the group consisting of H, $CO_2H$, ($C_1$-$C_6$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NHSO_2R^7$, $CH_2NHSO_2R^7$, $N(OH)C(O)R^7$, $P(R^7)O_2R^8$, $PO_3R^7R^8$, and [L]-[TBM];

X is CZ, N, O, S or $NR^7$;

each W is independently CH, CZ, N, O, S or $NR^7$;

each Z is independently selected from H, OH, $OR^4$, $CO_2H$, —($C_{1-6}$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, $PO_3R^4R^5$, and -[L][TBM], wherein the alkyl, alkenyl, alkynyl, cycloalkyl, heterocycloalkyl, aryl, and heteroaryl are each optionally substituted by 1, 2, 3, or 4 independently selected $R^X$ groups;

each $R^7$ and $R^8$ are independently selected from the group consisting of H, $C_1$-$C_6$ alkyl, and -[L]-[TBM], wherein the alkyl is optionally substituted by 1, 2 or 4 independently selected $R^X$ groups;

DG is selected from the group consisting of:

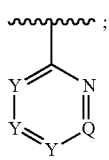

In some embodiments, the compound of Formula (VI) is:

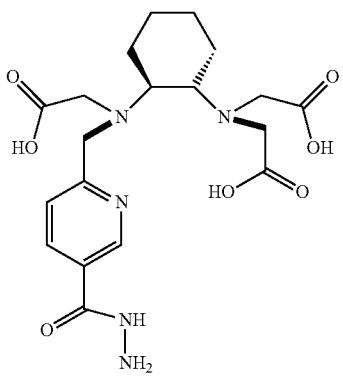

or a pharmaceutically acceptable salt thereof.

Further provided herein is a compound of Formula (XV):

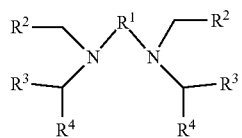

(XV)

or a pharmaceutically acceptable salt thereof, wherein:

$R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl)$(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;

each $R^2$, $R^3$, and $R^4$ are independently selected from the group consisting of COAL (C(O)NR$^5$R$^6$, CH$_2$NHCOR$^5$, C(O)N(OH)R$^5$, C(O)NHSO$_2$R$^5$, CH$_2$NHSO$_2$R$^5$, N(OH)C(O)R$^5$, P(R$^5$)O$_2$R$^6$, and PO$_3$R$^5$R$^6$, and compounds of formula:

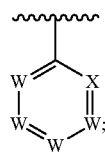

(XVI)

wherein X is CZ, N, O, S, or NR$^5$;
each W is independently CH, CZ, N, O, S, or NR$^5$;
each Z is independently selected from H, OH, OR$^4$, CO$_2$H, —(C$_{1-6}$ alkyl)CO$_2$H, C$_1$-C$_6$ alkyl, C$_2$-C$_6$ alkenyl, C$_2$-C$_6$ alkynyl, C$_4$-C$_6$ cycloalkyl, C$_6$-C$_{10}$ aryl, 5-6 membered heterocyclyl, 5-6 membered heteroaryl, C(O)NR$^5$R$^6$, CH$_2$NHCOR$^5$, C(O)N(OH)R$^5$, C(O)NHSO$_2$R$^5$, CH$_2$NHSO$_2$R$^5$, N(OH)C(O)R$^5$, P(R$^5$)O$_2$R$^6$, PO$_3$R$^5$R$^6$, and -[L]-[TBM], wherein the alkyl, alkenyl, alkynyl, cycloalkyl, heterocycloalkyl, aryl, and heteroaryl are each optionally substituted by 1, 2, 3, or 4 independently selected $R^X$ groups;

each $R^5$ and $R^6$ are independently selected from the group consisting of H, $C_1$-$C_6$ alkyl, and -[L]-[TBM], wherein the alkyl is optionally substituted by 1, 3, or 4 independently selected $R^X$ groups;

L is a linker;

TBM is a target binding moiety; and each $R^X$ is independently selected from the group consisting of OH, SH, CN, NO$_2$, halo, pseudohalo, amino, thionyl, sulfinyl, sulfonyl, sulfo, $C_1$-$C_4$ alkyl, $C_2$-$C_4$ alkenyl, alkynyl, $C_1$-$C_4$ haloalkyl, cyanoalkyl, $C_1$-$C_4$ hydroxyalkyl, $C_1$-$C_4$ alkoxy, $C_1$-$C_4$ aminoalkyl di($C_1$-$C_4$ alkyl)amino, $C_1$-$C_4$ alkylamine, phosphinate, phosphinate ester, phosphonate, phosphonate ester, phosphodiester, $C_{1-4}$ alkylphosphodiester, $C_3$-$C_6$ cycloalkyl, phenyl, 5-6 membered heteroaryl, 5-6 membered heterocycloalkyl, ($C_1$-$C_4$ alkyl)phenyl, and -[L]-[TBM].

In some embodiments, $R^1$ is 1,2-ethylene, $R^2$ is COON, $R^3$ is Formula XVI wherein X is N and all W are CH, and $R^4$ is selected from a compound Formula XVI. For example, $R^4$ is:

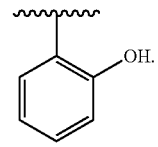

In some embodiments, $R^4$ is:

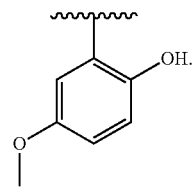 [SMILES: *c1cc(OC)ccc1O]

In some embodiments, $R^4$ is:

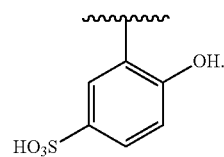

In some embodiments, $R^4$ is:

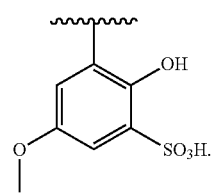 [SMILES: *c1cc(OC)cc(S(=O)(=O)O)c1O]

In some embodiments, $R^1$ is 1,2-ethylene, $R^2$ is COOH, $R^3$ is COOH, and $R^4$ is selected from compound Formula XVI. For example, $R^4$ is:
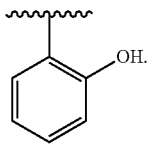
In some embodiments, $R^4$ is:
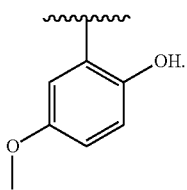
In some embodiments, $R^4$ is:
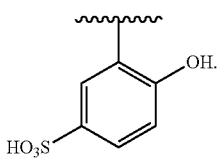
In some embodiments, $R^4$ is:
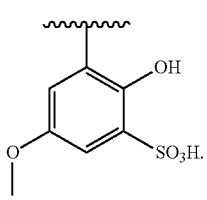
In some embodiments, the compound of Formula (XV) is selected from the group consisting of:
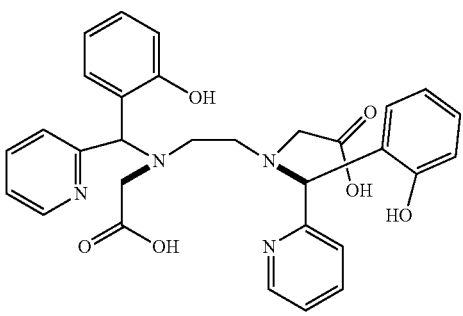
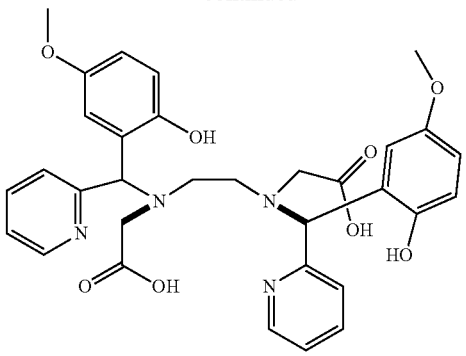
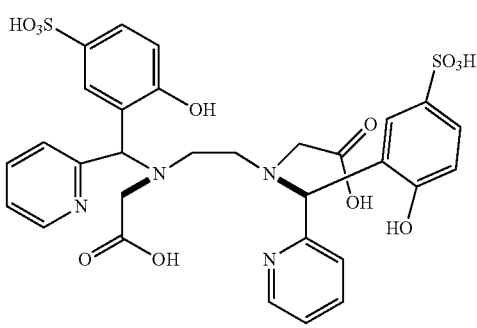
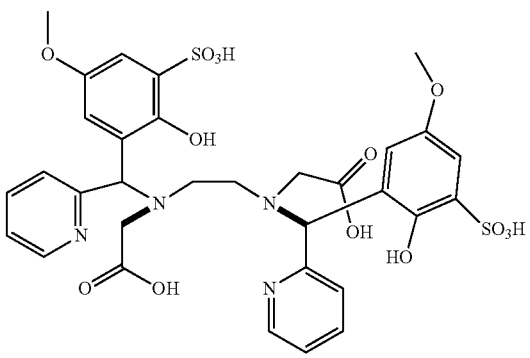
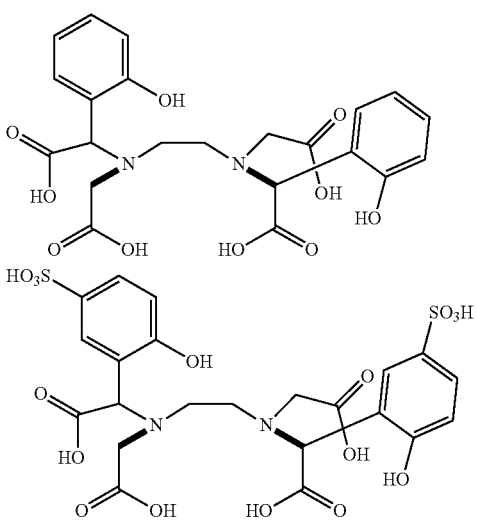

-continued

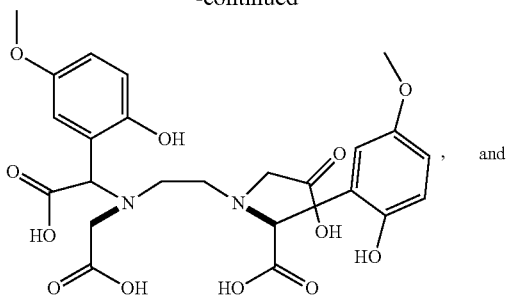

, and

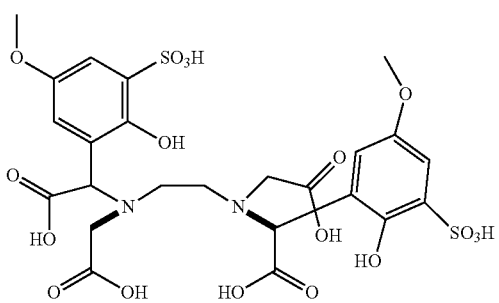

or a pharmaceutically acceptable salt thereof.

Also provided herein are compounds of Formula (XVII):

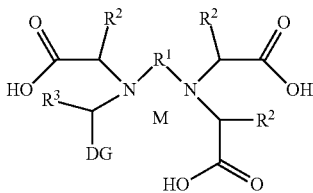

or a pharmaceutically acceptable salt thereof,
wherein:

$R^1$ is selected from the group consisting of a $C_2$-$C_6$ alkylene, a $C_3$-$C_{10}$ cycloalkylene, 4-10 membered heterocycloalkylene, arylene, 5-10 membered heteroarylene, ($C_1$-$C_6$) dialkyl)($C_6$-$C_{10}$ arylene), and ($C_1$-$C_6$)dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;

each $R^2$ and $R^3$ are independently selected from the group consisting of H, $CO_2H$, ($C_1$-$C_6$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, C(O)NR$^4$R$^5$, CH$_2$NHCOR$^4$, C(O)N(OH)R$^4$, C(O)NHSO$_2$R$^4$, CH$_2$NHSO$_2$R$^4$, IN(OH)C(O)R$^4$, P(R$^4$)O$_2$R$^5$, PO$_3$R$^4$R$^5$, and [L]-[TBM];

each and $R^5$ is independently selected from the group consisting of H, $C_1$-$C_6$ alkyl, and [L]-[TBM], wherein the alkyl is optionally substituted by 1, 3, or 4 independently selected $R^X$ groups;

DG is selected from the group consisting of:

(II)

(III)

(IV)

(V)

or any constitutional isomers of Formulas IV and V, wherein
each Y is independently CH, CZ, N, O, S, or NR$^4$;
Q is CH, CZ, N, O, S, or NR$^4$;
each Z is independently selected from the group consisting of H, OH, OR$^4$, $CO_2H$, —($C_{1-6}$)-alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, C(O)NR$^4$R$^5$, CH$_2$NHCOR$^4$, C(O)N(OH)R$^4$, C(O)NHSO$_2$R$^4$, CH$_2$NHSO$_2$R$^4$, N(OH)C(O)R$^4$, P(R$^4$)O$_2$R$^5$, PO$_3$R$^5$, and -[L]-[TBM], wherein the alkyl, alkenyl, alkynyl, cycloalkyl, heterocycloalkyl, aryl, and heteroaryl are each optionally substituted by 1, 2, 3, or 4 independently selected $R^X$ groups;
L is a linker;
TBM is a target binding moiety;
each $R^X$ is independently selected from the group consisting of OH, SH, CN, NO$_2$, halo, pseudohalo, amino, thionyl, sulfinyl, sulfonyl, sulfo, $C_1$-$C_4$ alkyl, $C_2$-$C_4$ alkenyl, $C_2$-$C_4$ alkynyl, $C_1$-$C_4$ haloalkyl, $C_1$-$C_4$ cyanoalkyl, $C_1$-$C_4$ hydroxyalkyl, $C_1$-$C_4$ alkoxy, $C_1$-$C_4$ aminoalkyl, di($C_1$-$C_4$ alkyl)amino, $C_1$-$C_4$ alkylamine, phosphinate, phosphinate ester, phosphonate, phosphonate ester, phosphodiester, $C_{1-4}$ alkylphosphodiester, $C_3$-$C_6$ cycloalkyl, phenyl, 5-6 membered heteroaryl, 5-6 membered heterocycloalkyl, ($C_1$-$C_4$ alkyl)phenyl, and -[L]-[TBM]; and
M is selected from the group consisting of Gd(III), Fe(III), Mn(II), Mn(III), Cr(III), Cu(II), Cu(III), Dy(III), Ho(III), Er(III), Pr(III), Eu(III), Nd(III), Lu(III), Sm(III), Tb(III), Tb(III), Tm(III), Y(III), In(III), Ga(III), Tc(III), Tc(IV), Tc(V), Re(III), Re(IV), Re(V), Bi(III), and Yb(III);
wherein, if Q is CH or CCOOH and all Y are CH, than at least one of $R^2$ or $R^3$ is not H.

In some embodiments, the compound of Formula (XVII) is selected from the group consisting of:

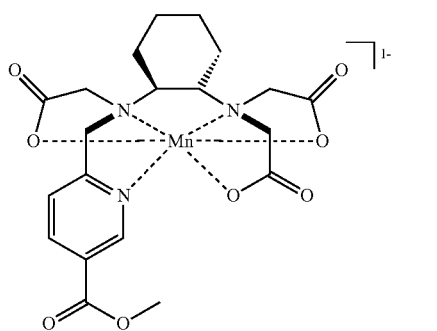
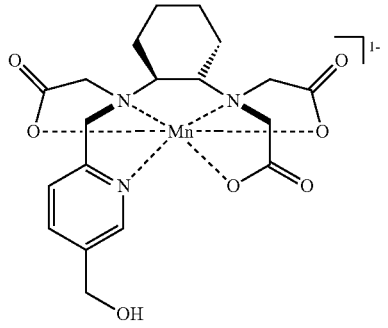
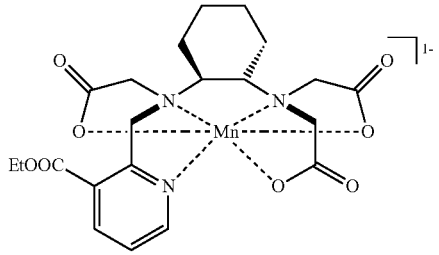
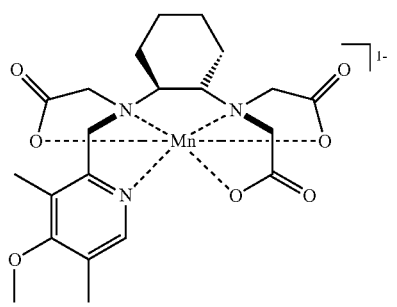
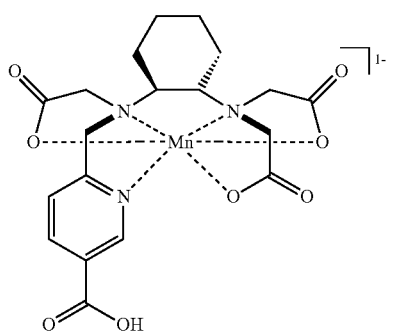
-continued
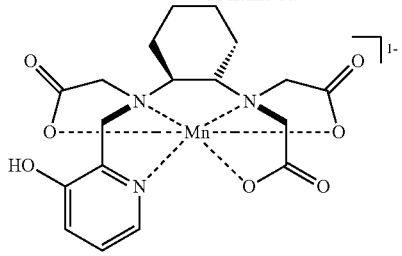
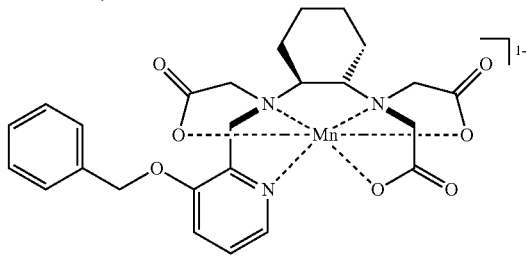
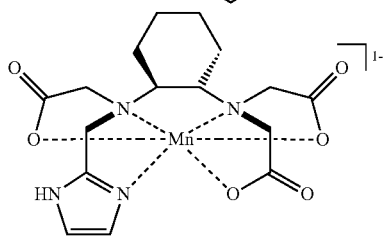
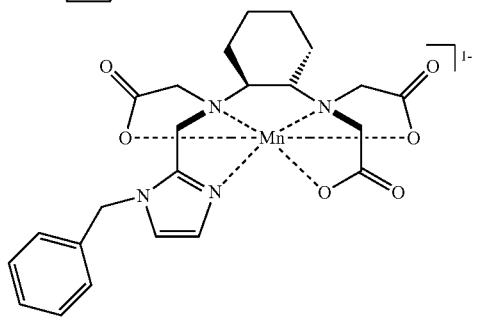
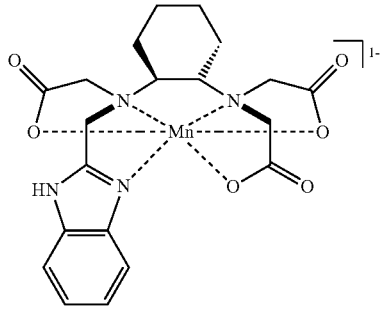
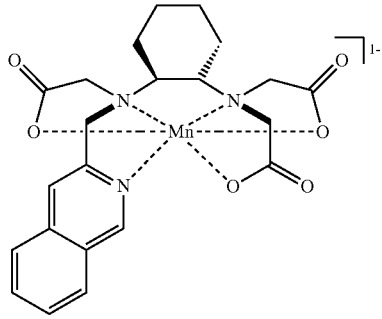
, and
or a pharmaceutically acceptable salt thereof.

Further provided herein are compounds of Formula (XVIII):

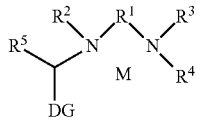 (XVIII)

or a pharmaceutically acceptable salt thereof, wherein:

$R^1$ is selected from the group consisting of a $C_2$-$C_6$ alkylene, a $C_3$-$C_{10}$; cycloalkylene, 4-10 membered heterocycloalkylene, $C_6$-$C_{10}$ arylene, 5-10 membered heteroarylene, $(C_1$-$C_6)$dialkyl$(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;

$R^2$, $R^3$, and $R^4$ are independently selected from the group of compounds of formula:

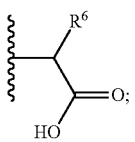 (VII)

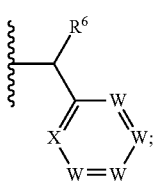 (VIII)

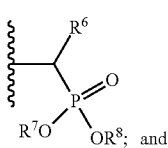 (IX)

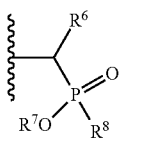 (X)

$R^5$ and $R^6$ are independently selected from the group consisting of H, $CO_2H$, $(C_1$-$C_6$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NHSO_2R^7$, $CH_2NHSO_2R^7$, $N(OH)C(O)R^7$, $P(R^7)O_2R^8$, $PO_3R^7R^8$, and $[L]$-$[TBM]$;

X is CZ, N, O, or S, or $NR^7$;

each is independently CH, CZ, N, O, S, or $NR^7$;

each Z is independently selected from H, OH, $OR^4$, $CO_2H$, $C_{1-6}CO_2H$, —$(C_{1-6}$ alkyl)$CO_2H$, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NRSO_2R^7$, $CH_2NHSO_2R^7$, $N(OH)C(O)R^7$, $P(R^7)O_2R^8$, $PO_3R^7R^8$, and -$[L]$-$[TBM]$, wherein the alkyl, alkenyl, alkynyl, cycloalkyl, heterocycloalkyl, aryl, and heteroaryl are each optionally substituted by 1, 2, 3, or 4 independently selected $R^X$ groups;

each $R^7$ and $R^8$ are independently selected from the group consisting of H, $C_1$-$C_6$ alkyl, and -$[L]$-$[TBM]$, wherein the alkyl is optionally substituted by 1, 2, 3, or 4 independently selected $R^X$ groups;

DG is selected from the group consisting of:

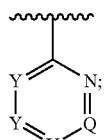 (XI)

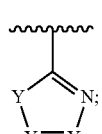 (XII)

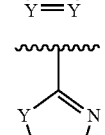 (XIII)

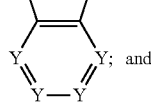 (XIV)

or any constitutional isomers of Formulas wherein each Y is independently CH, $CZ^1$, N, O, S, or $NR^7$;

Q is independently CH, $CZ^1$, N, O, S, or $NR^7$;

each $Z^1$ is independently selected from H, OH, $OR^7$, $CO_2H$, —$(C_{1-6}$ alkyl)$CO_2H$, $C_1$-$C_6$ alkyl, $C_2$-$C_6$ alkenyl, $C_2$-$C_6$ alkynyl, $(C_4$-$C_6$ cycloalkyl, $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NHSO_2R^7$, $CH_2NRSO_2R^7$, $N(OH)C(O)R^7$, $P(R^7)O_2R^8$, $PO_3R^7R^8$, and -$[L]$-$[TBM]$, wherein the alkyl, alkenyl, alkynyl, cycloalkyl, heterocycloalkyl, aryl, and heteroaryl are each optionally substituted by 1, 2, 3, or 4 independently selected $R^X$ groups;

L is a linker;

TBM is a target binding moiety;

each $R^X$ is independently selected from the group consisting of OH, SH, CN, $NO_2$, halo, pseudohalo, amino, thionyl, sulfonyl, sulfonyl, sulfa, $C_1$-$C_4$ alkyl, $C_2$-$C_4$ alkenyl, $C_2$-$C_4$ alkynyl, $C_1$-$C_4$ haloalkyl, $C_1$-$C_4$ cyanoalkyl, $C_1$-$C_4$ hydroxylalkyl, $C_1$-$C_4$ alkoxy, $C_1$-$C_4$ aminoalkyl, di$(C_1$-$C_4$ alkyl)amino, $C_1$-$C_4$ alkylamine, phosphinate, phosphinate ester, phosphonate, phosphonate ester, phosphodiester, $C_{1-4}$ alkylphosphodiester, $C_3$-$C_6$ cycloalkyl, phenyl; 5-6 membered heteroaryl, 5-6 membered heterocycloalkyl, $(C_1$-$C_4$ alkyl)phenyl, and -$[L]$-$[TBM]$; and M is selected from the group consisting of Gd(III), Mn(II), Cr(III), Cu(II), Cu(III), Dy(III), Ho(III), Er(III), Pr(III), Eu(II), Eu(III), Nd(III), La(III), Lu(III), Sm(III), Tb(III), Tb(IV), Tm(III), Y(III), In(III), Ga(III), Tc(III), TC(IV), Tc(V), Re(III), Re(IV), Re(V), Bi(III), and Yb(III); and wherein if Q is CH or CCOOH, all Y are CH, and all of $R^2$, $R^3$, and $R^4$ are formula VII, than at least one of $R^5$ or $R^6$ is not H; and if one of $R^2$, $R^3$, or $R^4$ is formula VIII, and all of $R^5$ and $R^6$ are H, than the aromatic ring component of formula VIII (i.e. the ring containing X and W) must be different than DG.

Also provided herein are compounds of Formula (XIX):

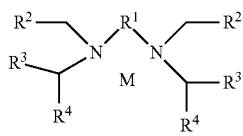

(XIX)

or a pharmaceutically acceptable salt thereof;
wherein:

$R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl$(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;

each $R^2$, $R^3$, and $R^4$ are independently selected from the group consisting of $CO_2H$, $C(O)NR^5R^6$, $CH_2NHCOR^5$, $C(O)N(OH)R^5$, $C(O)NHSO_2R^5$, $CH_2NHSO_2R^5$, $N(OH)C(O)R^5$, $P(R^5)O_2R^6$, and $PO_3R^5R^6$, and compounds of formula:

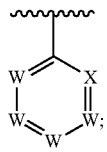

(XVI)

wherein X is CZ, N, O, or S, or $NR^4$;
each W is independently CH, CZ, N, O, S, or $NR^4$;
each Z is independently selected from H, OH, $OR^4$, $CO_2H$, —$(C_{1-6}$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^5R^6$, $CH_2NHCOR^5$, $C(O)N(OH)R^5$, $C(O)NHSO_2R^5$, $CH_2NHSO_2R^5$, —$N(OH)C(O)R^5$, $P(R^5)O_2R^6$, $PO_3R^5R^6$, and -[L]-[TBM], wherein the alkyl, alkenyl, alkynyl, cycloalkyl, heterocycloalkyl, aryl, and heteroaryl are each optionally substituted by 1, 2, 3, or 4 independently selected $R^X$ groups;

each $R^5$ and $R^6$ are independently selected from the group consisting of H, $C_1$-$C_6$ alkyl, and -[L]-[TBM], wherein the alkyl is optionally substituted by 1, 2, 3, or 4 independently selected $R^X$ groups;

L is a linker;
TBM is a target binding moiety;
each $R^X$ is independently selected from the group consisting of OH, SH, CN, $NO_2$, halo, pseudohalo, amino, thionyl, sulfonyl, sulfonyl, sulfa, $C_1$-$C_4$ alkyl, $C_2$-$C_4$ alkenyl, $C_2$-$C_4$ alkynyl, $C_1$-$C_4$ haloalkyl, $C_1$-$C_4$ cyanoalkyl, $C_1$-$C_4$ hydroxyalkyl, $C_1$-$C_4$ alkoxy, $C_1$-$C_4$ aminoalkyl, di($C_1$-$C_4$ alkyl)amino, $C_1$-$C_4$ alkylamine, phosphinate phosphinate ester, phosphonate, phosphonate ester, phosphodiester, $C_{1-4}$ alkylphosphodiester, $C_3$-$C_6$ cycloalkyl, phenyl, 5-6 membered heteroaryl, 5-6 membered heterocycloalkyl, ($C_1$-$C_4$ alkyl)phenyl, and -[L]-[TBM]; and M is selected from the group consisting of Gd(III), Mn(II), Mn(III), Cr(III), Cu(II), Cu(III), Dy(III), Ho(III), Er(III), Pr(III), Eu(II), Eu(III), Nd(III), La(III), Lu(III), Sm(III), Tb(III), Tb(IV), Tm(III), Y(III), In(III), Ga(III), Tc(III), Tc(IV), Tc(V), Re(III), Re(IV), Re(V), Bi(III), and Yb(III).

In some embodiments, the compound of Formula (XVIII) is selected from the group consisting of:

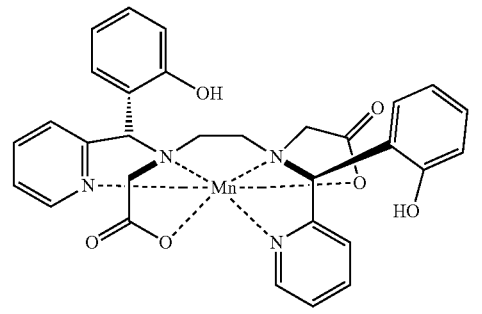

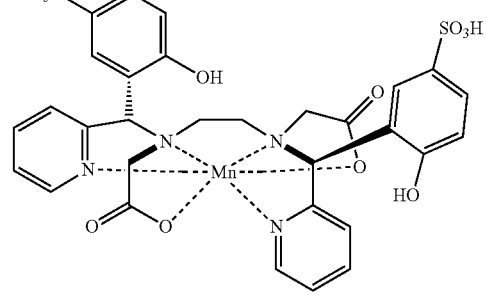

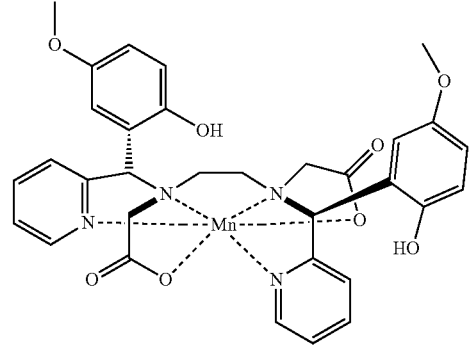

23
-continued
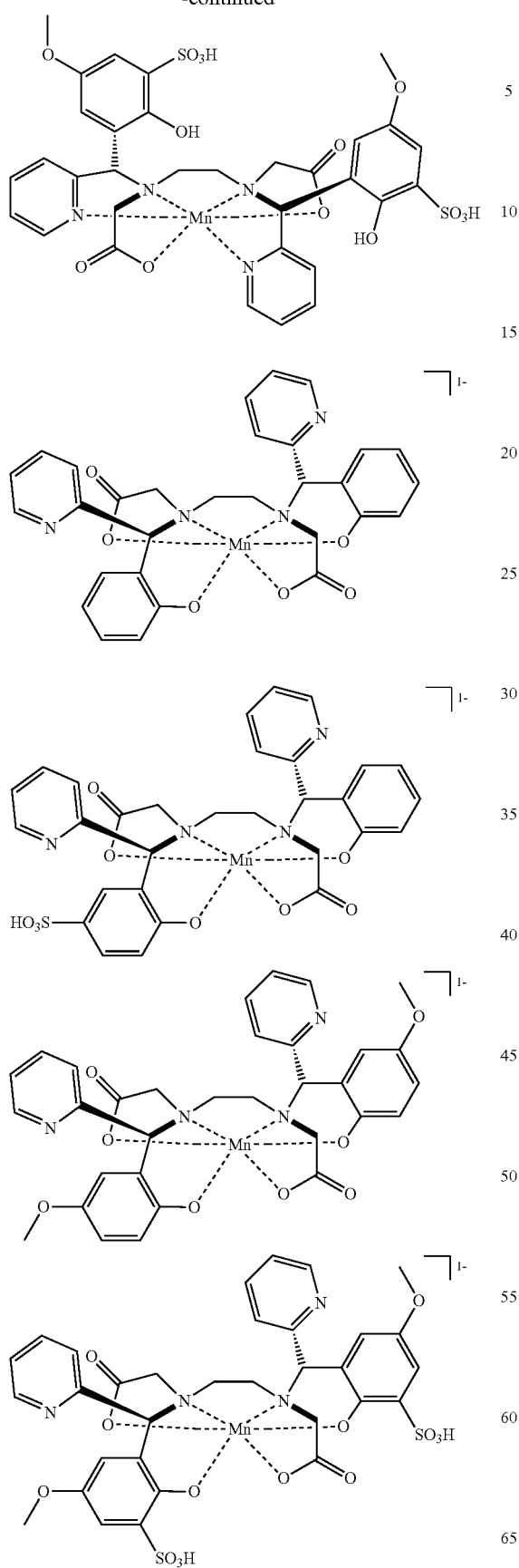
24
-continued
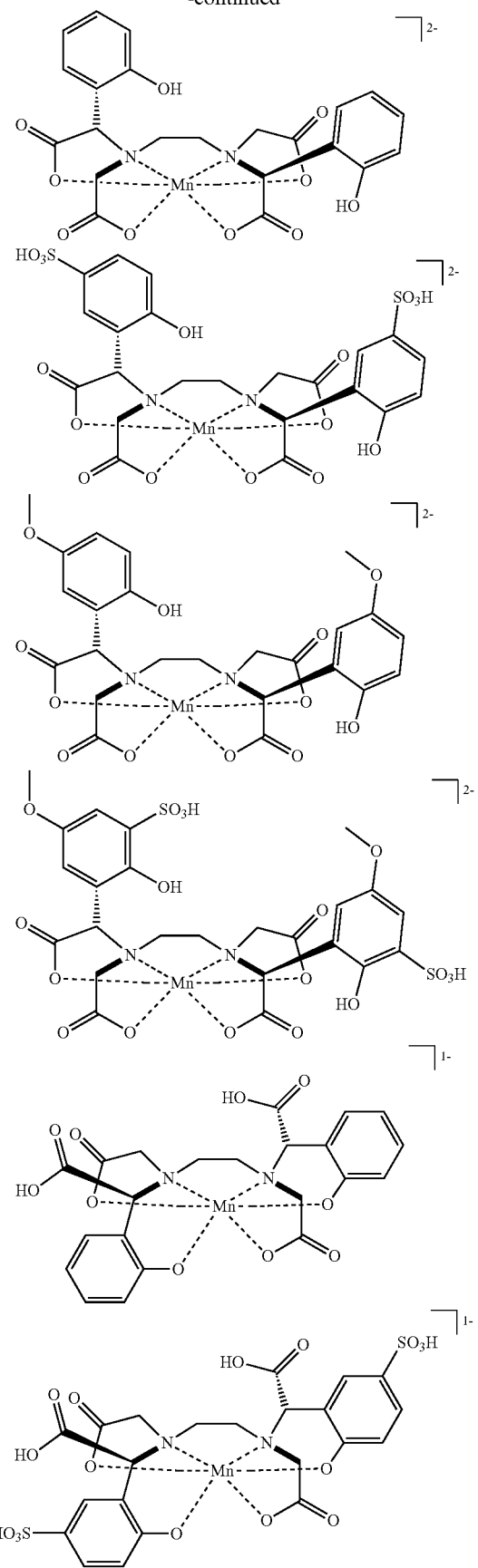

-continued

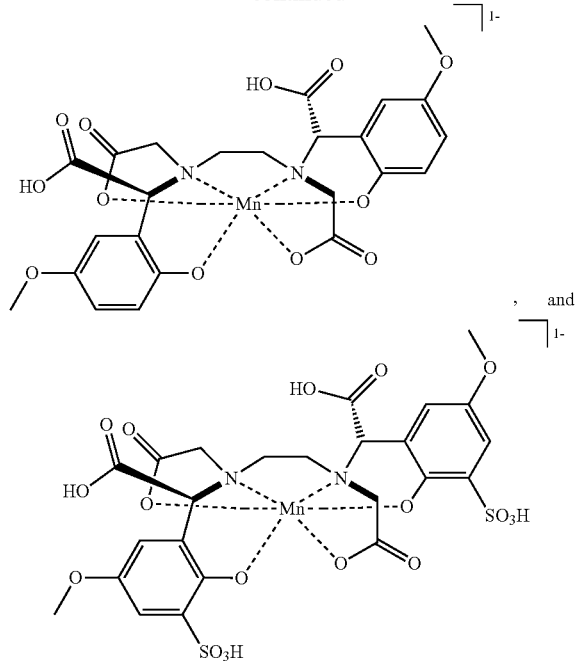

or a pharmaceutically acceptable salt or any corresponding stereoisomer thereof.

This disclosure further provides a compound of Formula (A):

$$(D^1)_a\text{-}(L^1)_b\text{-TBM-}(L^2)_c\text{-}(D^2)_d \qquad (A)$$

or a pharmaceutically acceptable salt thereof,
wherein:
TBM is a target binding moiety;
each $D^1$ is independently a metal chelate selected from a compound of
Formula (XVII), a compound of Formula (XVIII), and a compound of Formula (XIX);
each $D^2$ is independently a metal chelate selected from a compound of
Formula (XVII), a compound of Formula (XVIII), and a compound of Formula (XIX);
$L^1$ is a linker;
$L^2$ is a linker;
a is an integer from 0 to 4;
b is 0 or 1;
wherein if a is 0, b is 0;
c is 0 or 1;
d is an integer from 0 to 4;
wherein if d is 0, c is 0;
wherein at least one of a and d is an integer from 1 to 4.

In some embodiments, the [TBM] is:

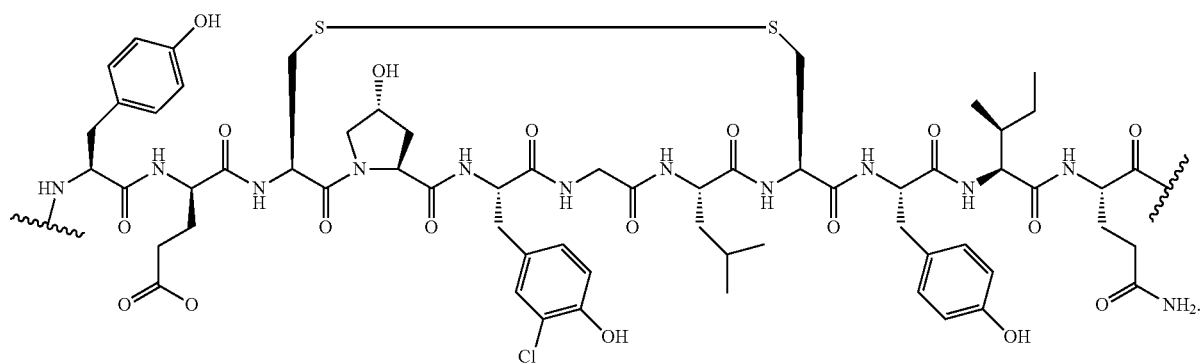 [SMILES: *N[C@@H](Cc1ccc(O)cc1)C(=O)N[C@H](CCC(=O)O)C(=O)N[C@H]1CSSC[C@@H](C(=O)N[C@@H](Cc2ccc(O)cc2)C(=O)N[C@H](C(=O)N[C@@H](CCC(N)=O)C(*)=O)[C@@H](C)CC)NC(=O)[C@H](CC(C)C)NC(=O)CNC(=O)[C@H](Cc2ccc(O)c(Cl)c2)NC(=O)[C@@H]2C[C@@H](O)CN2C1=O]

In some embodiments, the [TBM] is:

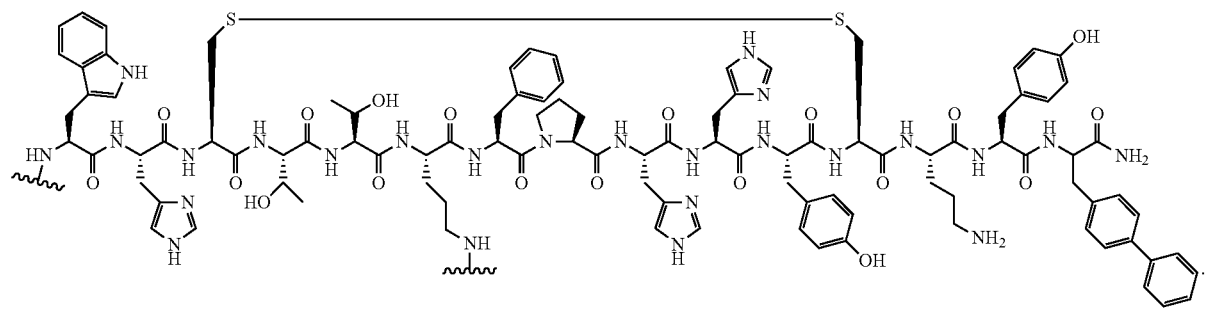 [SMILES: *NCCC[C@@H]1NC(=O)[C@H](C(C)O)NC(=O)[C@H](C(C)O)NC(=O)[C@@H](NC(=O)[C@H](Cc2c[nH]cn2)NC(=O)[C@H](Cc2c[nH]c3ccccc23)N*)CSSC[C@@H](C(=O)N[C@@H](CCCN)C(=O)N[C@@H](Cc2ccc(O)cc2)C(=O)NC(Cc2ccc(-c3ccccc3)cc2)C(N)=O)NC(=O)[C@H](Cc2ccc(O)cc2)NC(=O)[C@H](Cc2c[nH]cn2)NC(=O)[C@H](Cc2c[nH]cn2)NC(=O)[C@@H]2CCCN2C(=O)[C@H](Cc2ccccc2)NC1=O]

In some embodiments, $D^1$ and $D^2$ are a compound according to claim 1, wherein $R^1$ is 1,2-cyclohexylene, $R^2$ is H, $R^3$ is H, DG is Formula II, Q is CH, the Y positioned α- to Q is C-[L]-TBM, and all other Y are CH, and L is —C(O)—.

In some embodiments, the compound is selected from the group consisting of:

Also provided herein is a method of magnetic resonance (MR) imaging a patient, the method comprising: a) administering to the patient an effective amount of a compound comprising a metal chelate as provided herein; and b) acquiring an MR image of the patient. For example, a method for imaging a tumor in a patient is provided herein, the method comprising: a) administering to the patient an

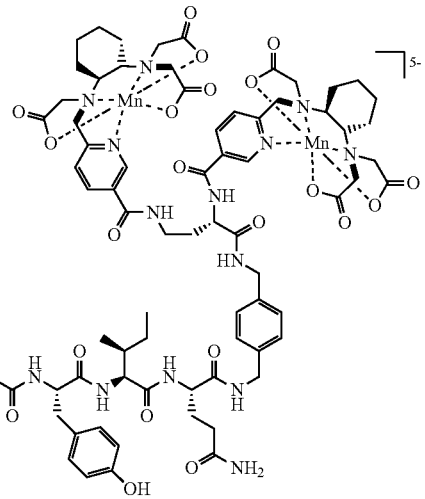

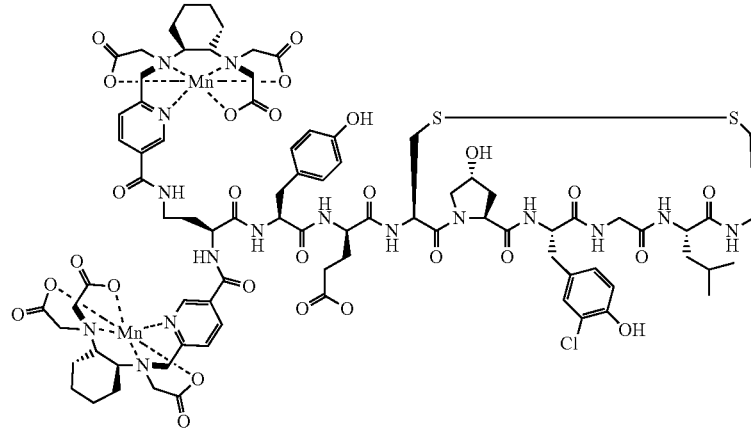

and

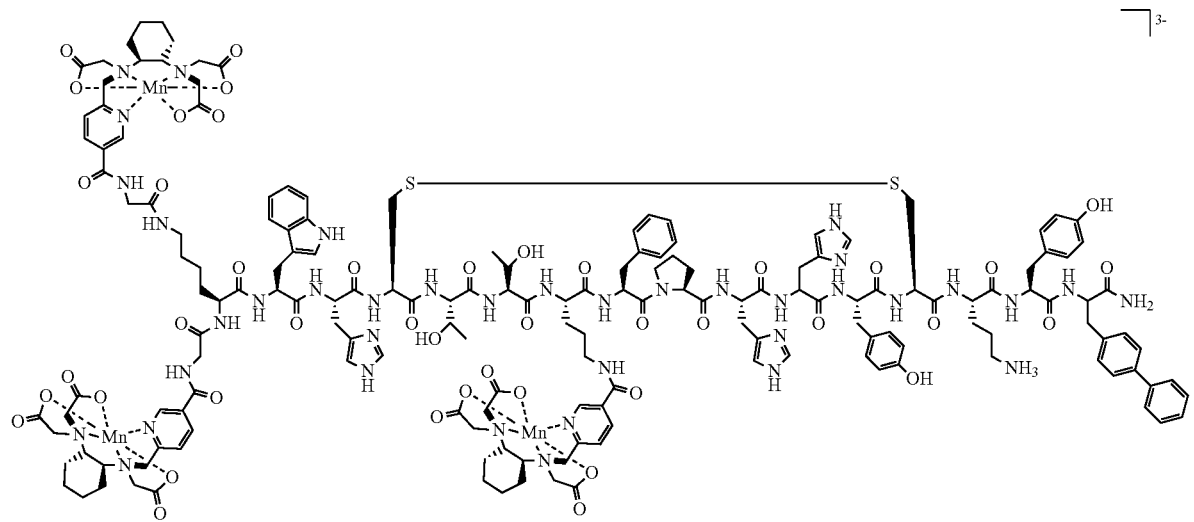

effective amount of a compound comprising a metal chelate as provided herein; and b) acquiring an MR image of the tumor. In some embodiments, the method can include a method for imaging a blood clot in a patient, the method comprising: a) administering to the patient an effective amount of a compound comprising a metal chelate as provided herein; and b) acquiring an MR image of the blood clot. In some embodiments, the method can include a method for imaging a brain lesion in a patient, the method comprising: a) administering to the patient an effective amount of a compound comprising a metal chelate as provided herein; and b) acquiring an MR image of the brain lesion.

Further provided herein is a method for detecting the presence or absence of disrupted blood-brain-barrier in a patient, the method comprising: a) administering to the patient an effective amount of a compound comprising a metal chelate as provided herein, wherein M is Mn(II); b) acquiring a first MR image of the brain of the patient; c) acquiring a second MR image of the brain of the patient; and comparing the images. In some embodiments, a method for detecting the presence or absence of arterial stenosis in a patient is provided, the method comprising: a) administering to the patient an effective amount of a compound comprising a metal chelate as provided herein, wherein M is Mn(II); b) acquiring a first MR image of the arteries of a patient; c) acquiring a second MR image of the arteries of patient immediately after injection of the compound; and d) comparing the images.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications; patent applications, patents, and other references mentioned herein are incorporated by reference in their entirety. In case of conflict, the present specification, including definitions, will control. In addition, the methods, materials, and examples are illustrative only and not intended to be limiting.

The details of one or more embodiments of the invention are set forth in the accompanying drawings and the description below. Other features, objects, and advantages of the invention will be apparent from the description and drawings, and from the claims.

SEQUENCE LISTING

The instant application contains a Sequence Listing which has been submitted electronically in ASCII format and is hereby incorporated by reference in its entirety. Said ASCII copy, created on Jul. 14, 2020, is named 40978-0032US1_ST25 and is 12.00 KB in size.

DETAILED DESCRIPTION

1. Definitions

Figure 1:
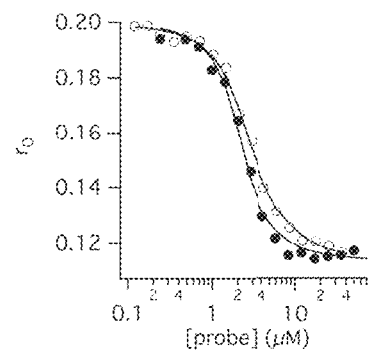
FIG. 1 shows that fibrin targeting compound 20 possesses high affinity for the soluble fibrin degradation product comprising the complex of a D-dimer domain and a E domain of the protein that is termed DD(E). Fluorescence polarization anisotropy of fluorescein labeled fibrin binding peptide in DD(E) solution as a function of added Mn-FBP (filled circles) or a known fibrin binding molecule EP2104R (open circles) to determine Ki to DD(E) is shown.

Commonly used chemical abbreviations that are not explicitly defined in this disclosure may be found in The American Chemical Society Style Guide, Second Edition; American Chemical Society, Washington, D.C. (1997), "2001 Guidelines for Authors" *J. Org, Chem.* 66(1), 24A (2001), and "A Short Guide to Abbreviations and Their Use in Peptide Science" *J. Peptide. Sci.* 5, 465-471 (1999).

The terms "chelating ligand," "chelating moiety," and "chelate moiety" are used interchangeably and refer to any polydentate ligand that is capable of coordinating a metal ion, either directly or after removal of protecting groups, or is a reagent, with or without suitable protecting groups, that is used in the synthesis of a MR contrast agent and comprises substantially all of the atoms that ultimately will coordinate the metal ion of the final metal complex. The terms "chelate" or "metal chelate" refer to the actual metal-ligand complex. It is understood that the polydentate ligand can eventually be coordinated to a medically useful or diagnostic metal ion.

The term "specific binding affinity" as used herein, refers to the capacity of a contrast agent to be taken up by, retained by, or bound to a particular or target biological component to a greater degree as compared to other non-targeted biological components. Contrast agents that have this property are said to be "targeted" to the "target" component. Contrast agents that lack this property are said to be "non-specific" or "non-targeted" agents. The binding affinity of a binding group for a target is expressed in terms of the equilibrium dissociation constant "IQ."

The term "relaxivity" as used herein, refers to the increase in either of the MR quantities $1/T_1$ or $1/T_2$ per millimolar (mM) concentration of paramagnetic ion or contrast agent, which quantities may be different if the contrast agent contains a multiplicity of paramagnetic ions, wherein $T_1$ is the longitudinal or spin-lattice relaxation time, and $T_2$ is the transverse or spin-spin relaxation time of water protons or other imaging or spectroscopic nuclei, including protons found in molecules other than water. Relaxivity is expressed in units of $mM^{-1}s^{-1}$.

The terms "target binding" and "binding" for purposes herein refer to non-covalent interactions of a contrast agent with a target. These non-covalent interactions are independent from one another and may be, inter cilia, hydrophobic, hydrophilic, dipole-dipole, pi-stacking, hydrogen bonding, electrostatic associations, or Lewis add-base interactions.

Coordination of metal ions by water and other ligands is often regarded in terms of coordination spheres (see e.g., D. T. Richens, The Chemistry of Aqua Ions, John Wiley and Sons, New York, 1997, Chapter 1). The first or primary coordination sphere represents all the ligands directly bonded to the metal ion and is defined by the ligands. There is a second coordination sphere where water molecules and counterions bond to the groups in the first coordination sphere via hydrogen bonding and electrostatic interactions. Tertiary and subsequent coordination spheres are typically termed "bulk water" or "bulk solvent". The distinctions between these spheres are both spatial and temporal. The first coordination sphere is typically well-defined and the time that a water or other ligand spends in the first coordination sphere is longer than in other coordination spheres. The second sphere is less well-defined, but the waters here have a longer lifetime than the typical diffusion time of water. Beyond the second sphere water diffuses freely.

As used herein, all references to "Mn(II)" or "manganese (II)" mean the Mn(II) paramagnetic metal ion; all references to "Mn(III)" or "manganese(III)" mean the Mn(III) paramagnetic metal ion. As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "cycloalkyl" or "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "cycloalkylene" means a bivalent cyclic ring system containing only carbon atoms in the ring system backbone, such as cyclopropylene, cyclobutylene, cyclopentylene, cyclohexylene, and cyclohexenylene. Cycloalkylenes may include multiple fused rings. Cycloalkylenes may have any degree of saturation provided that at least one ring in the ring system is not aromatic. Cycloalkylene groups can either be unsubstituted or substituted with one or more substituents. In some embodiments, cycloalkylene groups include 3 to 10 carbon atoms, for example, 3 to 6 carbon atoms.

As used herein, "aryl" means a mono-, bi-, tri- or poly-cyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include fluorenyl, phenyl, naphthyl, tetrahydronaphthyl, 2,3-dihydro-1H-indenyl, and others. In some embodiments, the aryl is phenyl.

As used herein, "arylene" means a bivalent mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic, Arylene groups can either be unsubstituted or substituted with one or more substituents. Examples of arylene include fluorenylene, phenylene, naphthylene, tetrahydronaphthyl, 2,3-dihydro-1H-indenylene, and others. In some embodiments, the aryl is phenylene.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl; triazinyl, thiazolyl benzothienyl, benzoxadiazolyl, benzofuranyl, benzimidazolyl; benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl; quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, and others. In some embodiments, the heteroaryl is selected from thienyl, pyridinyl, furyl, pyrazolyl, imidazolyl, pyranyl, pyrazinyl, and pyrimidinyl.

As used herein, the term "heteroarylene" means a bivalent mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroarylene groups can either be unsubstituted or substituted with one or more substituents.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrothryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; alkoxyl) optionally substituted with one or more of halide, hydroxyl, —$NH_2$, —NH($C_{1-3}$ alkyl), and N($C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —OSO$_2$(OR); a sulfonate [such as —SO$_2$(OH) and —SO$_2$(OR)]; —SO$_2$NR'R"; and —SO$_2$R; in which each occurrence of R, R' and R" are independently selected from H; alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from ($C_{1-6}$ alkyl); haloalkyl), a halide (e.g., F), a hydroxyl, —C(O)OR, —C(O)R, —(C$_{1-6}$ alkoxyl), —NRR', —C(O)NRR', isothiocyanyl, and a cyano, in which each occurrence of R and R' is independently selected from H and (C$_{1-6}$ alkyl). In some embodiments, the substituent is selected from (C$_{1-6}$ alkyl), —(C$_{1-6}$ haloalkyl), a halide (e.g.; F), a hydroxyl, —C(O)OR, —C(O)R, —(C$_{1-6}$ alkoxyl), —NRR', —C(O)NRR', and a cyano, in which each occurrence of R and R' is independently selected from H and (C$_{1-6}$ alkyl).

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "sulfinyl" or "thionyl" refers to —S(O)—. As used herein, "sulfonyl" or "sulfuryl" refers to —S(O)$_2$—. As used herein, "sulfo" refers to —S(O)$_2$O—. As used herein, "phosphinate" refers to —P(R)O$_2$H, and "phosphinate ester" refers to —P(R)O$_2$R'. As used herein, "phosphonate" refers to —PO$_3$H$_2$, and "phosphonate ester" refers to —PO$_3$RR'. As used herein, "phosphodiester" refers to —OPO$_3$R—, and "alkylphosphodiester" refers to OPO$_3$RR'. In the above groups, R is H or alkyl, and R' is alkyl.

The term "mammal" is used in its usual biological sense. Thus, it specifically includes humans, cattle, horses, monkeys, dogs, cats, mice, rats, cows, sheep, pigs, goats, and non-human primates, but also includes many other species.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

Design of Chelating Ligand

Provided herein are chelating ligands useful for preparing metal chelates having high relaxivity. In some embodiments, chelating ligands can be used to prepare non-specific metal chelates having high relaxivity. In some embodiments, the chelating ligands can be modified to incorporate one or more target binding moieties (TBMs). Chelating ligands having one or more target binding moieties can allow the chelating ligands (and metal chelates) to be targeted to one or more sites in vivo. Chelating ligands and metal chelates can be modified to incorporate self-assembling moieties (SAM), which are groups that promote the self-assembly of the chelates into micelles, liposomes, emulsions, etc. In some embodiments, chelating ligands and metal chelates are also useful as luminescent probes for use in high-throughput, multiplex, and/or real-time detection and analysis of biological molecules (e.g., immunoassays or real-time PCR applications).

Chelating ligands described herein are based on derivatives of diamine functionalized backbones. Derivatives are prepared by modifying the amine moieties of the scaffold with from one to three R groups and one or more heterocycle based donor groups ("DG"). The carbon that links the backbone amine and DG can be functionalized with an additional "R" group. Typically, R groups and DGs are able to coordinate a metal ion. R groups and DGs can be selected for their ability to enhance the relaxivity of the chelating ligand when in a metal chelate form and/or to promote a specific oxidation state of the metal ion. Relaxivity may be enhanced, for example, by a DG's effect on the water exchange rate of a metal chelate; its ability to decrease the electronic relaxation rate of the metal ion; its ability to prevent anion coordination e.g., by electrostatic repulsion; or its ability to trap a biochemically generated oxidation state. In some embodiments, a DG can also incorporate a second sphere moiety (SSM), a group that increases relaxivity by its ability to coordinate a second sphere of water (e.g., by hydrogen bonding). In some embodiments, a DG can also incorporate a TBM, optionally through a linker (L) as discussed below. Relaxivity can be further enhanced by binding to the target of the TBM or by forming self-assembled systems such as liposomes.

A variety of chelating ligands can be prepared.

In some embodiments, the chelating ligand is a compound of Formula

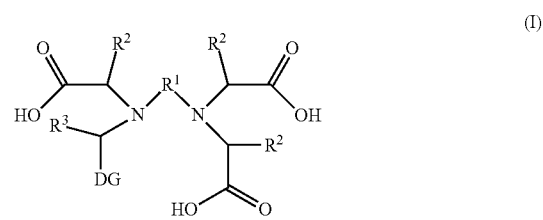

(I)

or a pharmaceutically acceptable salt thereof,

R$^1$ is selected from the group consisting of a C$_2$-C$_6$ alkylene, a C$_1$-C$_{10}$ cycloalkylene, 4-10 membered heterocycloalkylene, C$_6$-C$_{10}$ arylene, 5-10 membered heteroarylene, (C$_1$-C$_6$)dialkyl)(C$_6$-C$_{10}$ arylene), and (C$_1$-C$_6$)dialkyl(5-10 membered heteroarylene), wherein the alkylene, cycloalkylene, heterocycloalkylene, arylene, and heteroarylene are each optionally substituted by 1, 2, 3, or 4 independently selected R$^x$ groups. In some embodiments, the R$^1$ moiety is bound to the adjacent nitrogens through adjacent atoms, such as adjacent carbon atoms (e.g., binding through the 1 and 2 carbons on ethylene) or through atoms separated by a single methylene (e.g., binding through the 1 and 3 carbons on propylene). Similar binding may be observed with the cyclic moieties of R$^1$, for example, binding through adjacent carbon atoms (e.g., binding through the 1 and 2 carbons on cyclohexylene).

In some embodiments, R$^1$ is selected from the group consisting of a substituted or unsubstituted alkylene, such as 1,3-propylene or 1,2-ethylene, as shown below:

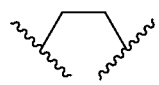

or 2,3-propylene-1-carboxylate, as shown below,

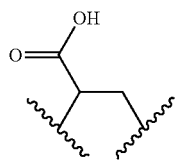 [SMILES: *CC(*)C(=O)O]

or 3,4-butylene-1-carboxylic acid, as shown below,

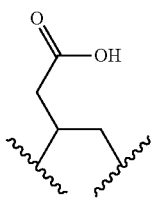 [SMILES: *CC(*)CC(=O)O]

or 1-hydroxy-3,4-butylene, as shown below,

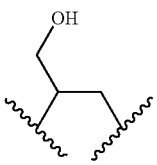 [SMILES: *CC(*)CO]

or 1-amino-5,6-hexylene, as shown below,

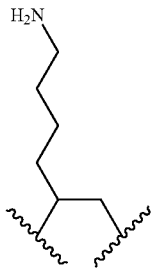 [SMILES: *CC(*)CCCCN]

substituted or unsubstituted cycloalkylene, such as those shown below, for example, cis- or trans-1,2-cyclohexylene, as shown below,

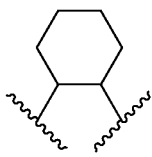 [SMILES: *C1CCCCC1*]

or trans-1,2-cyclohexylene, as shown below,

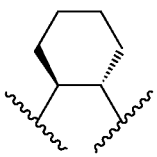 [SMILES: *[C@H]1CCCC[C@@H]1*]

or cis- or trans-1,2-cyclopentylene, as shown below,

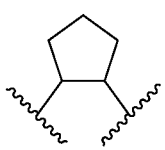 [SMILES: *C1CCCC1*]

substituted or unsubstituted monocyclic heterocyclyl, such as 2,5-dihydro-lit-pyrrolene, as shown below

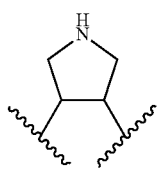 [SMILES: *C1CNCC1*]

1,2,3,6-tetrahydropyridinene, as shown below,

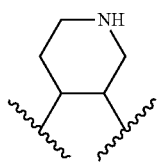 [SMILES: *C1CCNCC1*]

2,3,6,7-tetrahydro-1H-azepinene, as shown below,

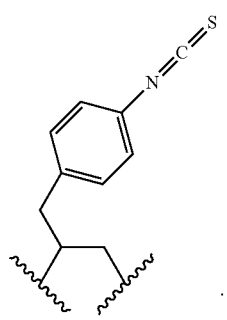 [SMILES: *CC(*)Cc1ccc(N=C=S)cc1]

and any corresponding isomers of the substituted or unsubstituted monocyclic heterocyclyl compounds, substituted or unsubstituted aryl, substituted or unsubstituted heteroaryl, and substituted or unsubstituted arylalkylene, such as 1-propylene-4-isothiocyanatobenzene, as shown below, In some embodiments, $R^1$ can be substituted with [L]-[TBM], such as 1-propylene-benzene functionalized with a thiourea (NH—C(S)—NH-)[L] and the albumin targeting substituted arylalkylene TBM, 2,2',4,4',5,6'-hexamethyl-1,1'-biphenyl, as shown below,

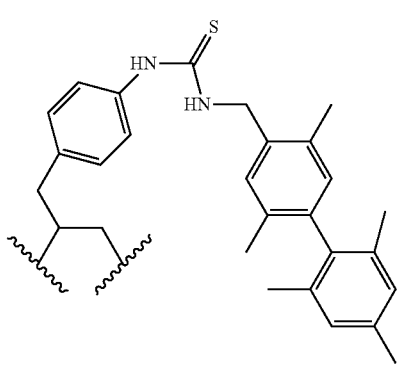 [SMILES: *CC(*)Cc1ccc(NC(=S)NCc2cc(C)c(-c3c(C)cc(C)cc3C)cc2C)cc1]

each $R^2$ and $R^3$ is independently selected from the group consisting of H, $CO_2H$, $(C_1-C_6\text{alkyl})CO_2H$, $C_1-C_6$ alkyl, $C_2-C_6$ alkenyl, $C_2-C_6$ alkynyl, $C_4-C_6$ cycloalkyl, $C_6-C_{10}$ aryl, 5-6 membered heteroaryl, 5-6 membered heterocyclyl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, $PO_3R^4R^5$, and [L]-[TBM];

each $R^4$ and $R^5$ are independently selected from the group consisting of H, substituted or unsubstituted $C_1-C_6$ alkyl, and [L]-[TBM]; and DG is selected from the group consisting of:

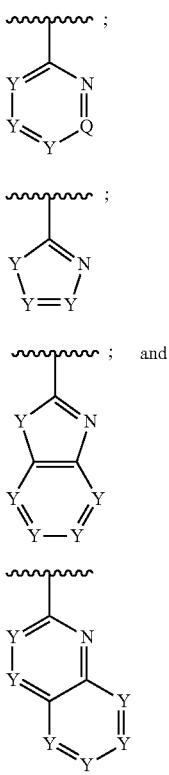

or any constitutional isomers of Formulas IV and V, wherein
Y is CH, CZ, N, O, S or $NR^4$;
each Q is independently CH, CZ, N, O, S, or $NR^4$; and
Z is selected from the group consisting of H, OH, $OR^4$, $CO_2R^4$, $-(C_{1-6}\text{ alkyl})CO_2H$, $C_1-C_6$ alkyl, $C_2-C_6$ alkenyl, $C_2-C_6$ alkynyl, $C_4-C_6$ cycloalkyl, $C_6-C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, $PO_3R^4R^5$, and -[L]-[TBM], wherein the alkyl, alkenyl, alkynyl, cycloalkyl, heterocycloalkyl, aryl, and heteroaryl are each optionally substituted by 1, 2, 3, or 4 independently selected $R^X$ groups;

L is a linker;
TIM is a target binding moiety; and
each $R^X$ is independently selected from the group consisting of OH, SH, CN, $NO_2$, halo, pseudohalo, amino, thionyl, sulfinyl, sulfonyl, sun, isothiocyanyl, $C_1-C_4$ alkyl, $C_2-C_4$ alkenyl, $C_2-C_4$ alkynyl, $C_1-C_4$ haloalkyl, $C_1-C_4$ cyanoalkyl, $C_1-C_4$ hydroxyalkyl, $C_1-C_4$ alkoxy, $C_1-C_4$ aminoalkyl, di($C_1-C_4$ alkyl)amino, $C_1-C_4$ alkylamine, phosphinate, phosphinate ester, phosphonate, phosphonate ester, phosphodiester, $C_{1-4}$ alkylphosphodiester, $C_3-C_6$ cycloalkyl, phenyl, 5-6 membered heteroaryl, 5-6 membered heterocycloalkyl, ($C_1-C_4$ alkyl)phenyl, wherein the phenyl may be substituted or unsubstituted, and -[L]-[TBM];

In some embodiments, if Q is CH, CCOOH, or $CCH_2$-(4-nitrobenzyl sulfonamide) and all Y are CH, than at least one of $R^2$ or $R^3$ is not H.

In some embodiments, a compound of Formula (I) is a compound of Formula (IA):

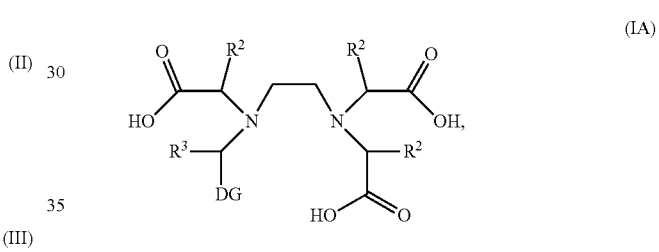

(IA)

or a pharmaceutically acceptable salt thereof, wherein $R^2$, $R^3$, and DG are as defined for Formula (I).

In some embodiments, a compound of Formula (I) is a compound of Formula (IB):

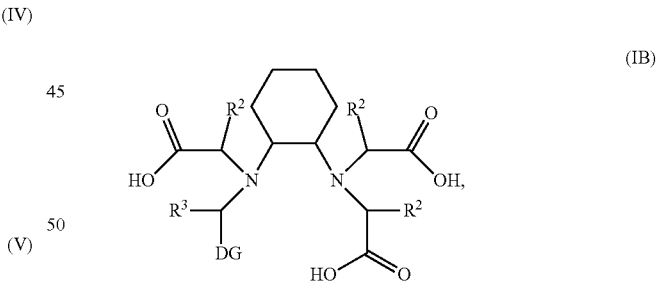

(IB)

or a pharmaceutically acceptable salt thereof, wherein $R^2$, $R^3$, and DG are as defined for Formula (I).

In some embodiments, the chelating ligand is a compound of Formula (VI):

(VI)

or a pharmaceutically acceptable salt thereof;

R¹ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, ($C_1$-$C_6$)dialkyl($C_6$-$C_{10}$ arylene); and ($C_1$-$C_6$)dialkyl(5-10 membered heteroarylene), wherein the alkylene, cycloalkylene, heterocycloalkylene, arylene, and heteroarylene are each optionally substituted by 1, 2, 3, or 4 independently selected $R^x$ groups.

In some embodiments, the R¹ moiety is bound to the adjacent nitrogens through adjacent carbon atoms (e.g., binding through the 1 and 2 carbons on ethylene) or through carbons separated by a single methylene (e.g., binding through the 1 and 3 carbons on propylene). Similar binding may be observed with the cyclic moieties of R¹, for example, binding through adjacent carbon atoms (e.g., binding through the 1 and 2 carbons on cyclohexylene).

In some embodiments, R¹ is selected from the group consisting of a substituted or unsubstituted alkylene, such as 1,3-propylene or 1,2-ethylene, as shown below:

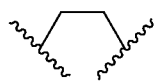 [SMILES: *CC*]

or 2,3-propylene-1-carboxylate, as shown below,

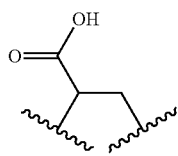 [SMILES: *CC(*)C(=O)O]

or 3,4-butylene-1-carboxylic acid, as shown below,

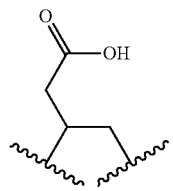 [SMILES: *CC(*)CC(=O)O]

or 1-hydroxy-3,4-butylene, as shown below,

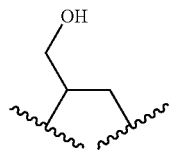 [SMILES: *CC(*)CO]

or 1-amino-5,6-hexylene, as shown below,

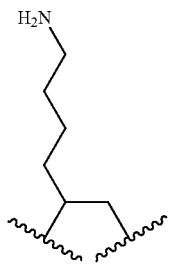 [SMILES: *CC(*)CCCCN]

such as cis- or trans-1,2-cyclohexylene, as shown below,

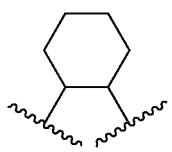 [SMILES: *C1CCCCC1*]

or cis- or trans-1,2-cyclopentylene, as shown below,

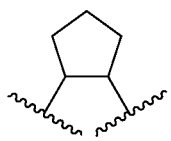 [SMILES: *C1CCCC1*]

substituted or unsubstituted monocyclic heterocyclyl, such as 2,5-dihydro-1H-pyrrolene, as shown below

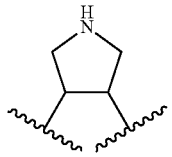 [SMILES: *C1CNCC1*]

1,2,3,6-tetrahydropyridinene; as shown below;

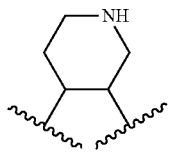 [SMILES: *C1CCNCC1*]

2,3,6,7-tetrahydro-1H-azepinene, as shown below,

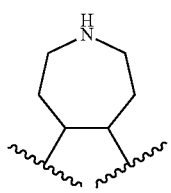 [SMILES: *C1CCNCCC1*]

and any corresponding isomers of the substituted or unsubstituted monocyclic heterocyclyl compounds, substituted or unsubstituted aryl, substituted or unsubstituted heteroaryl, and substituted or unsubstituted arylalkylene, such as I-propylene-4-isothiocyanatobenzene, as shown below,

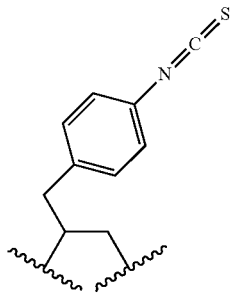 [SMILES: *CC(*)Cc1ccc(N=C=S)cc1]

In some embodiments, $R^1$ can be substituted with [L]-[TBM], such as 1-propylene-benzene functionalized with a thiourea (—NH—C(S)—NH—)[L] and the albumin targeting substituted arylalkylene TBM, 2,2',4,4',5,6-hexamethyl-1,1'-biphenyl, as shown below,

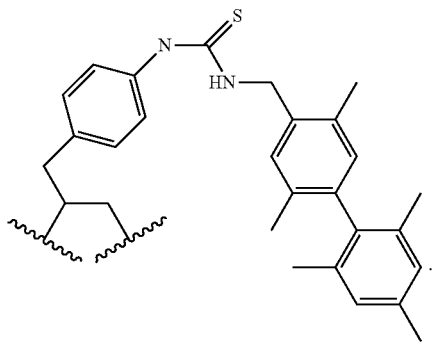 [SMILES: *CC(*)Cc1ccc(NC(=S)NCc2cc(C)c(-c3c(C)cc(C)cc3C)cc2C)cc1]

$R^2$, $R^3$, and $R^4$ are independently selected from the group of compounds of formula:

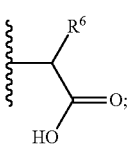

(VII)

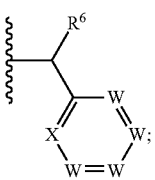

(VIII)

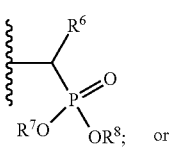

(IX)

or

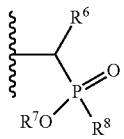

(X)

wherein each $R^5$ and $R^6$ are independently selected from the group consisting of is independently selected from the group consisting of H, $CO_2H$, $(C_1$-$C_6$ alkyl)$CO_2H$, $C_1$-$C_6$ alkyl, $C_2$-$C_6$ alkenyl, $C_2$-$C_6$ alkynyl, $C_4$-$C_6$ cycloalkyl $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NHSO_2R^7$, $CH_2NHSO_2R^7$, $N(OH)C(O)R^7$, $P(R^7)O_2R^8$, $PO_3R^7R^8$, and [L]-[TBM];

X is CZ, N, O, S or $NR^4$;

W is CH, CZ, N, O, S, or $NR^4$; and each Z is independently selected from H, OH, $OR^7$, $CO_2R^7$, —$(C_{1-6}$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NHSO_2R^7$, $CH_2NHSO_2R^7$, $N(OH)C(O)R^7$, $P(R^7)O_2R^8$, $PO_3R^7R^8$, and -[L]-[TBM], wherein the alkyl, alkenyl, alkynyl, cycloalkyl, heterocycloalkyl, aryl, and heteroaryl are each optionally substituted by 2, or 4 independently selected $R^X$ groups;

L is a linker;

TBM is a target binding moiety; and each $R^X$ is independently selected from the group consisting of OH, SH, CN, $NO_2$, halo, pseudohalo; amino, thionyl, sulfonyl, sulfonyl, sulfo; $C_1$-$C_4$ alkyl, $C_2$-$C_4$ alkenyl, $C_2$-$C_4$ alkynyl, $C_1$-$C_4$, haloalkyl, $C_1$-$C_4$ cyanoalkyl, $C_1$-$C_4$ hydroxyalkyl, $C_1$-$C_4$ alkoxy; $C_1$-$C_4$ aminoalkyl, di($C_1$-$C_4$ alkyl)amino, $C_1$-$C_4$ alkylamine, phosphinate, phosphinate ester, phosphonate, phosphonate ester, phosphodiester, $C_{1-4}$ alkylphosphodiester, $C_3$-$C_6$ cycloalkyl phenyl, 5-6 membered heteroaryl, 5-6 membered heterocycloalkyl; ($C_1$-$C_1$ alkyl)phenyl, and -[L]-[TBM];

each $R^7$ and $R^8$ are independently selected from the group consisting of H, substituted or unsubstituted $C_1$-$C_6$ alkyl, and [L]-[TBM]; and DG is selected from the group consisting of:

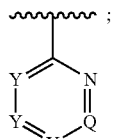

(XI)

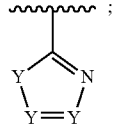

(XII)

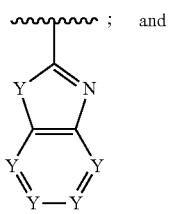 (XIII)

and

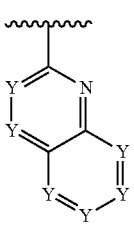 (XIV)

or any constitutional isomers of Formulas XIII-XIV, wherein each Y is independently CH, $CZ^1$, N, O, S, or $NR^4$ each Q is independently CH, $CZ^1$, N, O, S, or $NR^4$; and each $Z^1$ is independently selected from the group consisting of H, OH, $OR^7$, $CO_2R^7$, —$(C_{1-6}$ alkyl$)CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^7R^8$, $CH_2NHCOR^7$, $C(O)N(OH)R^7$, $C(O)NHSO_2R^7$, $CH_2NHSO_2R^7$, $N(OH)C(O)R^7$, $P(R^7)O_2R^8$, $PO_3R^7R^8$, and -[L]-[TBM], wherein the alkyl, alkenyl, alkynyl, cycloalkyl, heterocycloalkyl, aryl, and heteroaryl are each optionally substituted by 1, 2, 3, or 4 independently selected $R^X$ groups.

In some embodiments, if Q is CH, CCOOH, or $CCH_2$-(4-nitrobenzylsulfonamide), all Y are CH, and all of $R^2$, $R^3$, and $R^4$ are formula Vii, than at least one of $R^5$ or $R^6$ is not H.

In some embodiments, if one of $R^2$, $R^3$, or $R^4$ is formula VIII, and all of $R^5$ and $R^6$ are H, than the aromatic ring component of formula VIII (i.e. the ring containing X and WI must be different than DG.

In some embodiments, a compound of Formula (VI) is a compound of Formula (XVa):

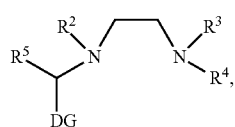 (VIa)

or a pharmaceutically acceptable salt thereof, wherein $R^2$, $R^3$, $R^4$, $R^5$ and $DG^4$ are as defined for Formula (VI).

In some embodiments, a compound of Formula (VI) is a compound of Formula (XVb):

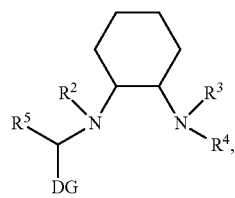 (VIb)

or a pharmaceutically acceptable salt thereof, wherein $R^2$, $R^3$, $R^4$, $R^5$ and DG are as defined for Formula (VI).

In some embodiments, the chelating ligand is a compound of Formula XV

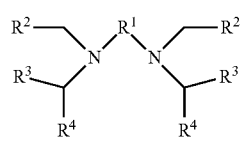 (XV)

or a pharmaceutically acceptable salt thereof, $R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl$)(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 3, or 4 independently selected $R^X$ groups.

In some embodiments, the $R^1$ moiety is bound to the adjacent nitrogens through adjacent carbon atoms (e.g., binding through the 1 and 2 carbons on ethylene) or through carbons separated by a single methylene (e.g., binding through the 1 and 3 carbons on propylene). Similar binding may be observed with the cyclic moieties of $R^1$, for example, binding through adjacent carbon atoms (e.g., binding through the 1 and 2 carbons on cyclohexylene).

In some embodiments, $R^1$ is selected from the group consisting of a substituted or unsubstituted alkylene, such as 1,3-propylene or 1,2-ethylene, as shown below:

or 2,3-propylene-1-carboxylate, as shown below,

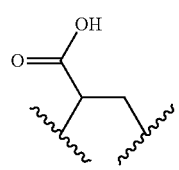 [SMILES: *CC(*)C(=O)O]

or 3,4-butyl ene-1-carboxylic acid, as shown below,

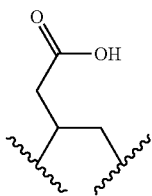 [SMILES: *CC(*)CC(=O)O]

or 1-hydroxy-3,4-butylene, as shown below,

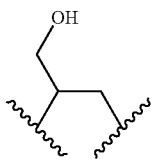 [SMILES: *CC(*)CO]

or 1-amino-5,6-hexylene, as shown below,

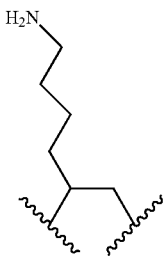

such as cis- or trans-1,2-cyclohexylene, as shown below,

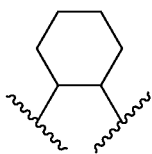 [SMILES: *C1CCCCC1*]

or cis- or trans-1,2-cyclopentylene, as shown below,

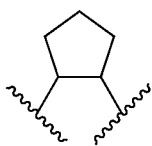 [SMILES: *C1CCCC1*]

substituted or unsubstituted monocyclic heterocyclyl, such as 2,5-dihydro-1H-pyrrolene, as shown below

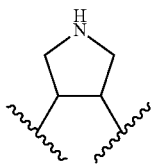 [SMILES: *C1CNCC1*]

1,2,3,6-tetrahydropyridinene, as shown below,

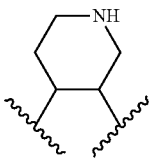

2,3,6,7-tetrahydro-1H-azepinene, as shown below,

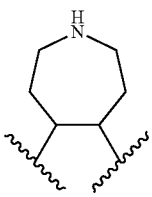 [SMILES: *C1CCNCCC1*]

and any corresponding isomers of the substituted or unsubstituted monocyclic heterocyclyl compounds, substituted or unsubstituted aryl, substituted or unsubstituted heteroaryl, and substituted or unsubstituted arylalkylene, such as I-propylene-4-isothiocyanatobenzene, as shown below,

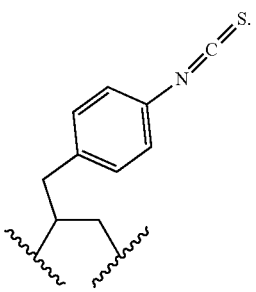 [SMILES: *CC(*)Cc1ccc(N=C=S)cc1]

In some embodiments, $R^1$ can be substituted with [L]-[TBM], such as 1-propylene-benzene functionalized with a thiourea (—NH—C(S)—NH-)[L] and the albumin targeting substituted arylalkylene TBM, 2',4,4',5,6'-hexamethyl-1,1'-biphenyl, as shown below,

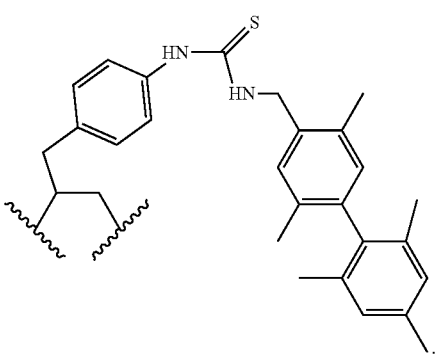 [SMILES: *CC(*)Cc1ccc(NC(=S)NCc2cc(C)c(-c3c(C)cc(C)cc3C)cc2C)cc1]

each $R^2$, $R^3$, and $R^4$ are independently selected from the group consisting of $CO_2H$, $C(O)NR^5R^6$, $CH_2NHCOR^5$, $C(O)N(OH)R^5$, $C(O)NHSO_2R^5$, $CH_2NHSO_2R^5$, $N(OH)C(O)R^5$, $P(R^5)O_2R^6$, and $PO_3R^5R^6$, and compounds of formula.

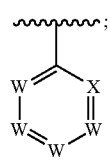

wherein X is a CZ, N, O, S, or NR⁴;
each W is independently CH, CZ, N, O, S, or NR⁴; and
each Z is independently selected from H, OH, OR⁵, CO₂R⁵, —(C$_{1-6}$ alkyl)CO₂H, C₁-C₆ alkyl, C₂-C₆ alkenyl, C₂-C₆ alkynyl, C₄-C₆ cycloalkyl, C₆-C₁₀ aryl, 5-6 membered heterocyclyl, 5-6 membered heteroaryl, C(O)NR⁵R⁶, CH₂NHCOR⁵, C(O)N(OH)R⁵, C(O)NHSO₂R⁵, CH₂NHSO₂R⁵, N(OH)C(O)R⁵, P(R⁵)O₂R⁶, PO₃R⁵R⁶, and -[L]-[TBM], wherein the alkyl, alkenyl, alkynyl, cycloalkyl, heterocycloalkyl, aryl, and heteroaryl are each optionally substituted by 1; 2, or 4 independently selected $R^X$ groups;

L is a linker;

TBM is a target binding moiety; and each $R^X$ is independently selected from the group consisting of OH, SH, CN, NO₂, halo, pseudohalo, amino, thionyl, sulfinyl, sulfonyl, sulfo, C₁-C₄ alkyl, C₂-C₄ alkenyl, C₂-C₄ alkynyl, haloalkyl, C₁-C₄ cyanoalkyl, C₁-C₄ hydroxyalkyl, C₁-C₄ alkoxy, C₁-C₄ aminoalkyl, di(C₁-C₄ alkyl)amino, C₁-C₄ alkylamine, phosphinate, phosphinate ester, phosphonate, phosphonate ester, phosphodiester, C$_{1-4}$ alkylphosphodiester, C₃-C₆ cycloalkyl phenyl, 5-6 membered heteroaryl, 5-6 membered heterocycloalkyl, (C₁-C₄ alkyl)phenyl, and -[L]-[TBM]; and each R⁵ and R⁶ are independently selected from the group consisting of H, substituted or unsubstituted C₁-C₆ alkyl; and [L]-[TBM].

In some embodiments, a compound of Formula (XV) is a compound of Formula (XVa):

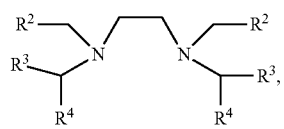

or a pharmaceutically acceptable salt thereof, wherein R², R³, and R⁴ are as defined for Formula (XV).

In some embodiments, a compound of Formula (XV) is a compound of Formula (XVb):

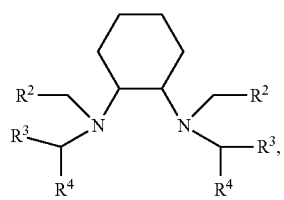

or a pharmaceutically acceptable salt thereof, wherein R², R³, and R⁴ are as defined for Formula (XV).

In some embodiments, the DG has been modified to target blood plasma proteins such as serum albumin.

Non-limiting examples of chelating ligands as provided herein include:

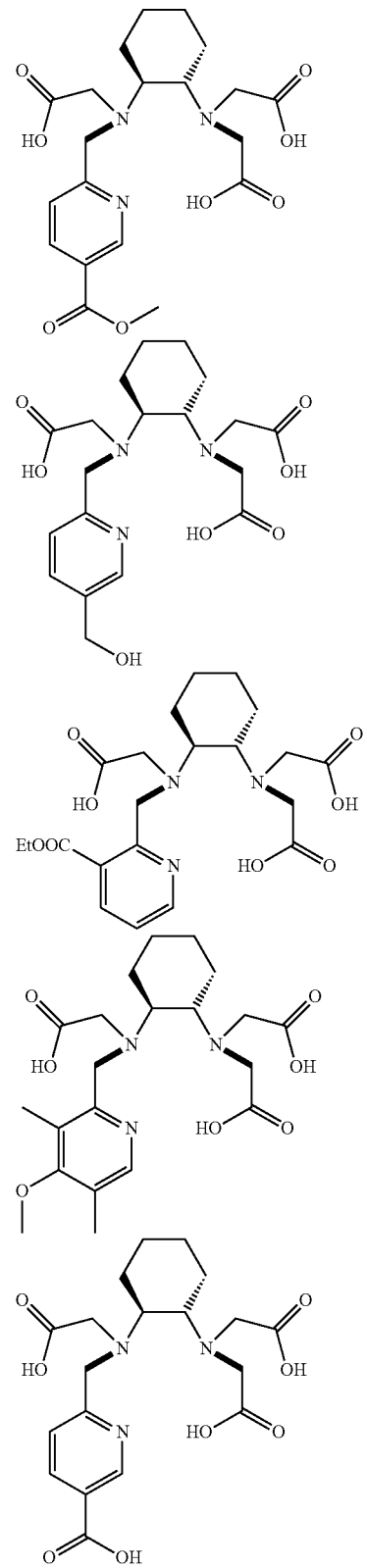

51
-continued
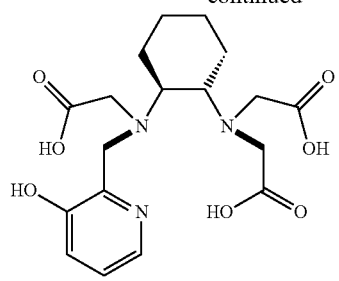
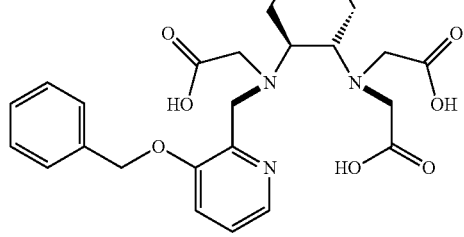
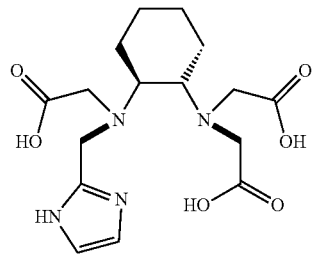
52
-continued
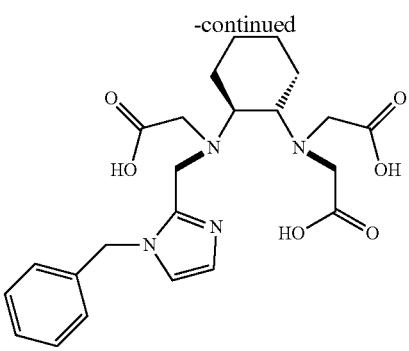
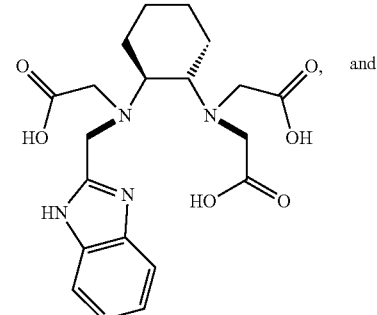
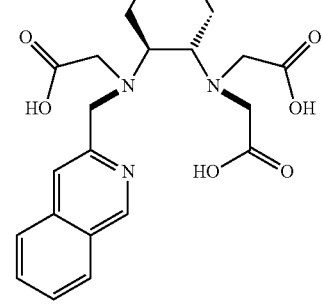
In another example embodiment, one or more (e.g., 2, 3, 4, 5, or 6) chelating ligands are linked to a TBM that has high affinity for fibrin. For example, such a compound can have the formula shown below:
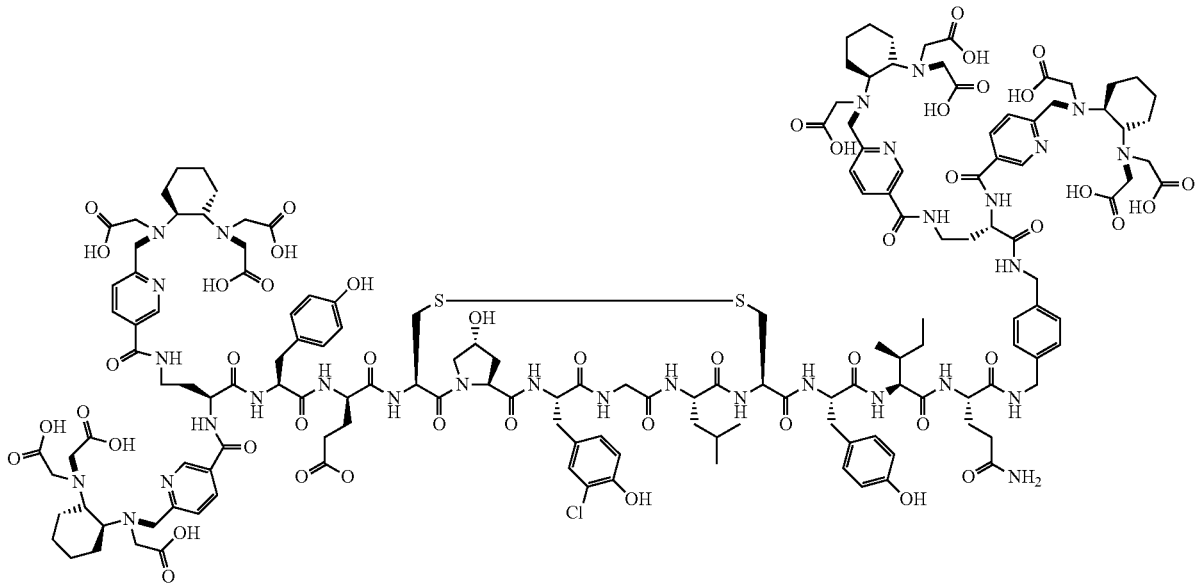
or a pharmaceutically acceptable salt thereof.

In another embodiment, one or more (e.g., 2, 3, 4, 5, or 6) chelating ligands are linked to a TBM that has high affinity for collagen. For example, one such compound can have the formula shown below:

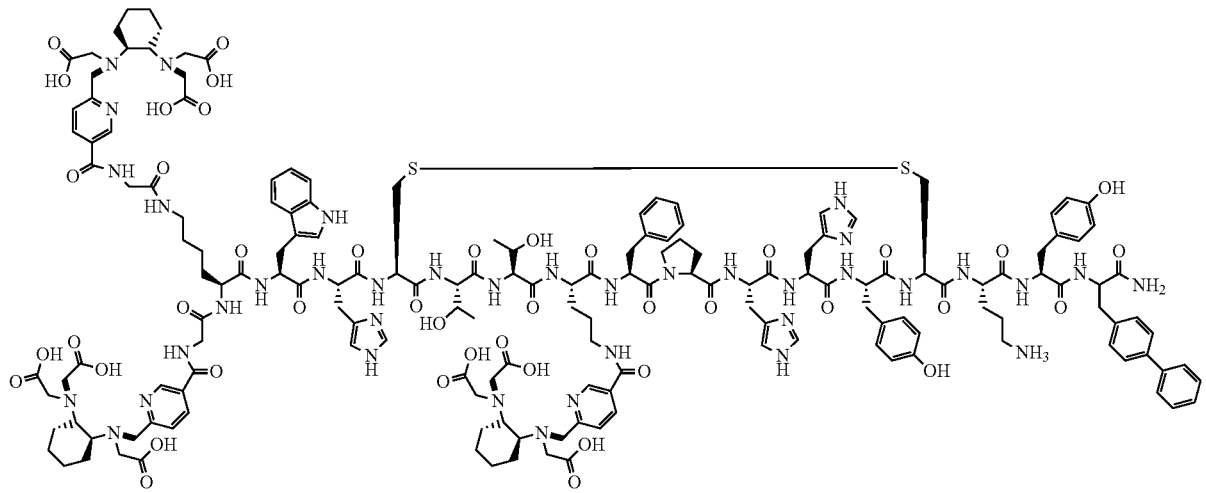

or a pharmaceutically acceptable salt thereof.

In another embodiment, the chelating ligand linked to a TBM that has high affinity for protein carbonyls, such as hydrazides. For example, one chelating ligand has the formula shown below

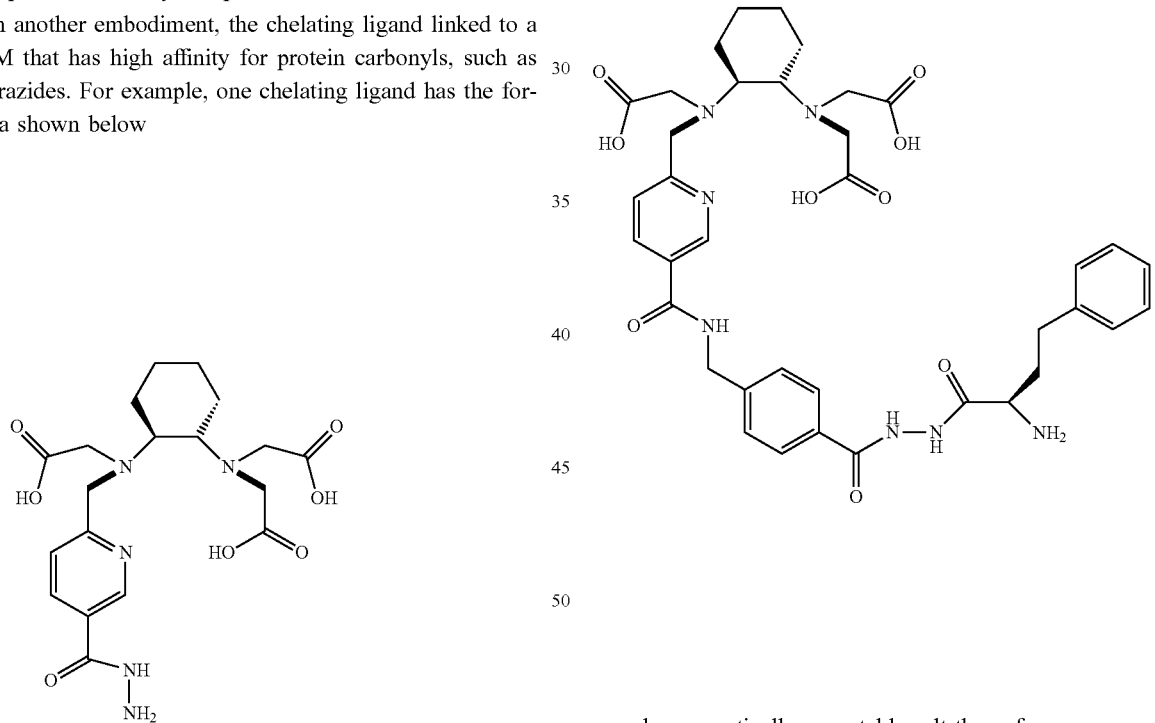

or a pharmaceutically acceptable salt thereof.

In another embodiment, the chelating ligand linked to a TBM that has high affinity for elastin. For example, one chelating ligand has the formula shown below or a pharmaceutically acceptable salt thereof.

In another embodiment, the chelating ligand has DG and R that favor binding of Mn(II), but also ancillary R that favor binding of Mn(III), wherein the R groups favoring Mn(II) in each chelate or chelating ligand are different from those that favor Mn(III). For example, when M=Mn, $R^3$ groups that favor Mn(II) can be independently selected from COOH, $PO_3H_2$, or formula XVI where x=N, while $R^4$ groups that favor Mn(III) can be independently selected from COOH, $PO_3H_2$, or formula XVI where X=C(OH). Non-limiting examples of such compounds include:

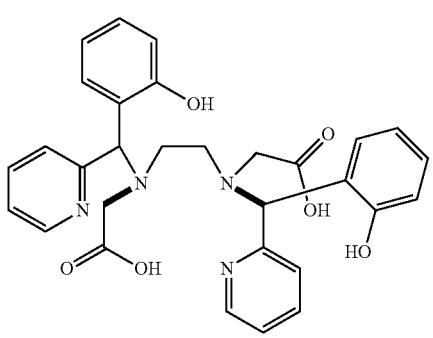
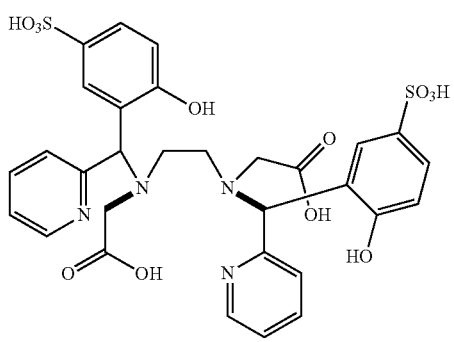
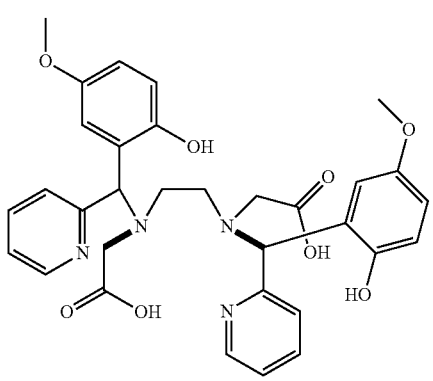
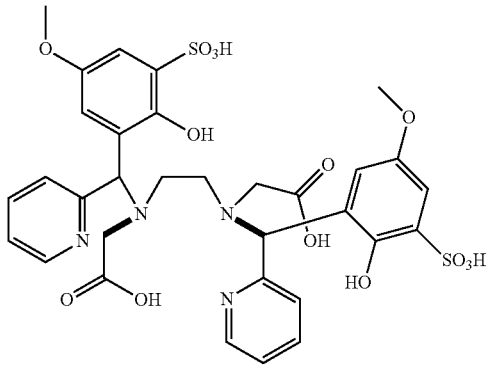
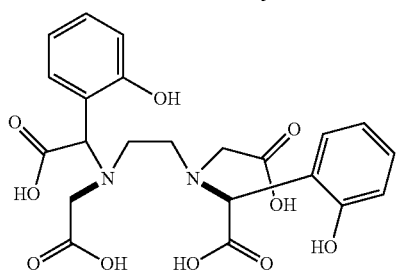
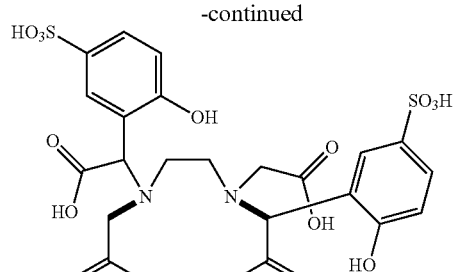
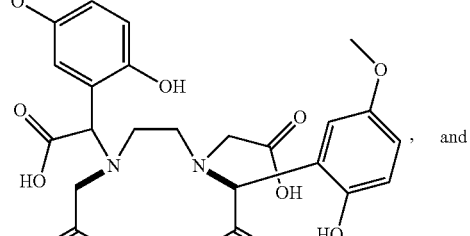
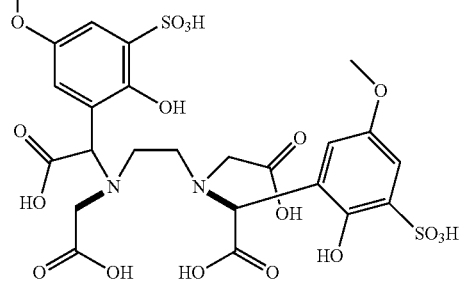
or a pharmaceutically acceptable salt thereof.
The synthetic protocols used to the prepare chelating ligands are general and can be broadly extended to include additional embodiments.
In some embodiments, the chelating ligand is coordinated to a metal to form a compound of general formula as follows:
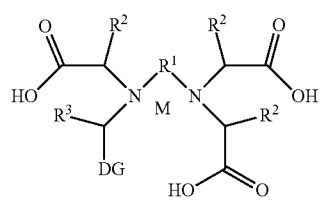
(XVII)
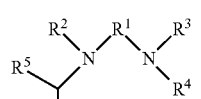
(XVIII)
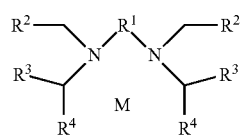
(XIX)

or a pharmaceutically acceptable salt thereof, wherein all moieties are as defined above. For example, the chelating ligand coordinated to a metal can form a compound of general formula:

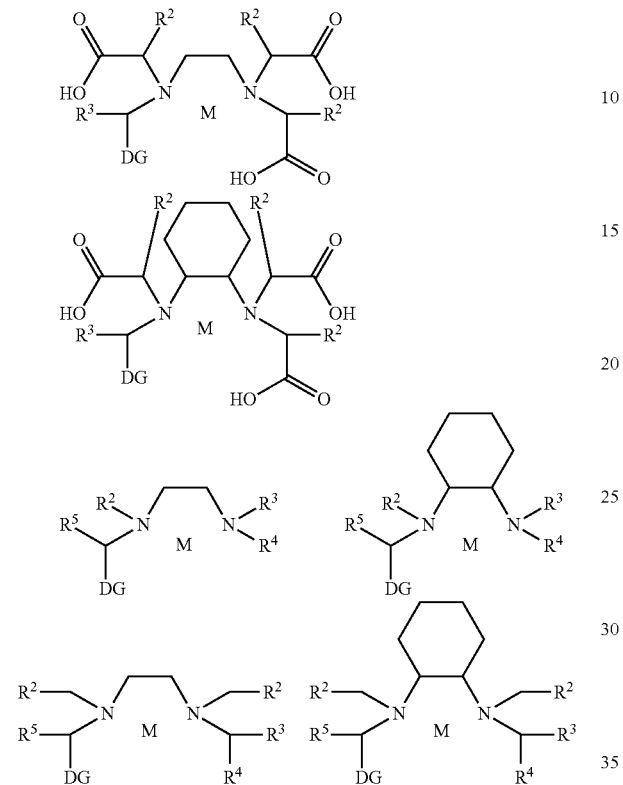

or a pharmaceutically acceptable salt thereof.

In such embodiments, M can be a stable or unstable isotope selected from Gd(III), Fe(III), Mn(II), Mn(III), Cr(III), Cu(II), Cu(III), Dy(III), Ho(III), Er(III), Pr(III), Eu(II), Eu(III), Nd(III), La(III), Lu(III), Sm(III), Tb(III), Tb(IV), Tm(III), Y(III), In(III), Ga(III), Tc(III), Tc(IV), Tc(V), Re(III), Re(IV), Re(V), Bi(III), and Yb(III). In some embodiments, M is Mn(II) or Mn(III).

In some embodiments, the DG of the chelate-metal complex has been modified to target blood plasma proteins such as serum albumin.

Non-limiting examples of metal chelates as provided herein include:

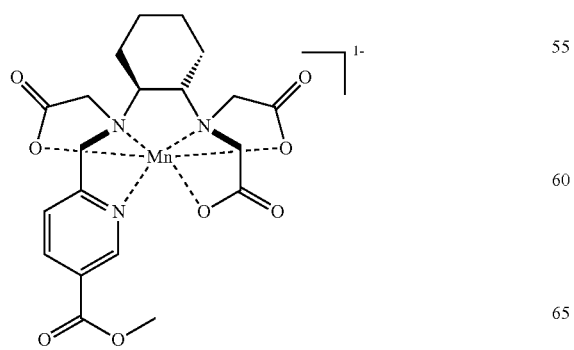

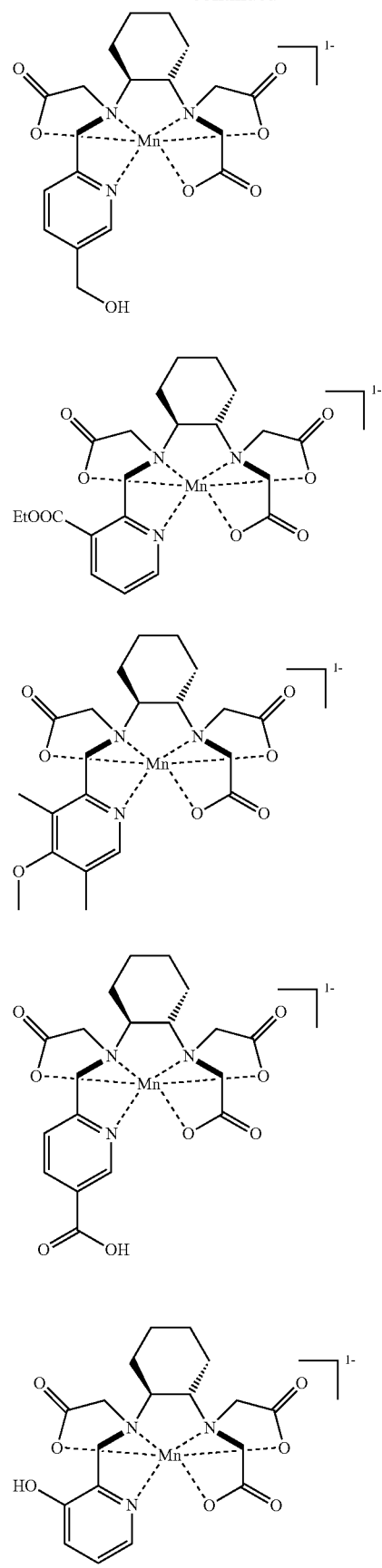

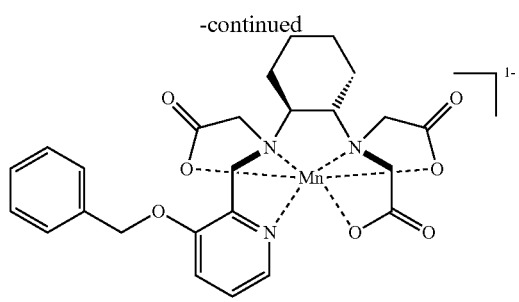
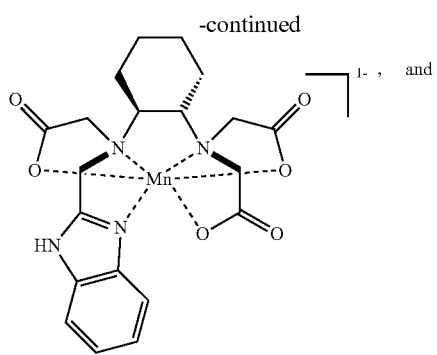
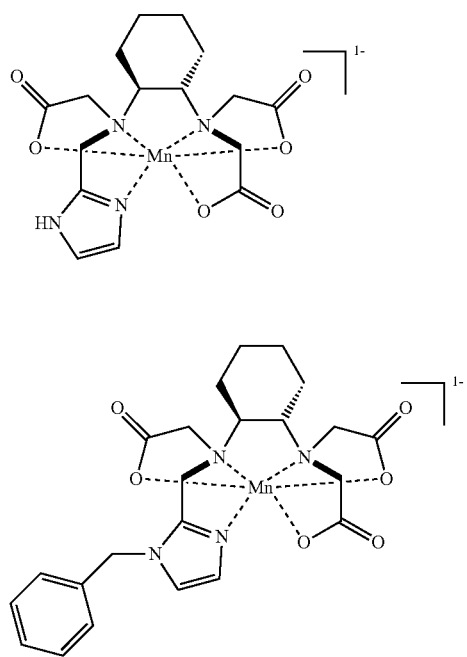
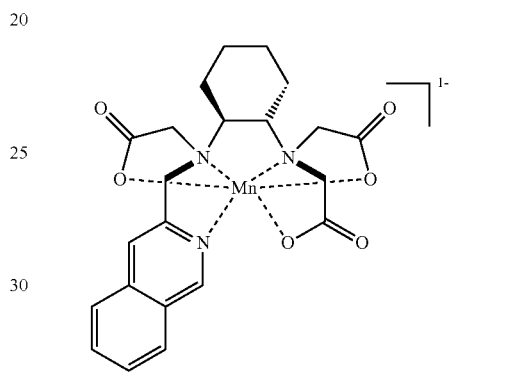
or a pharmaceutically acceptable salt thereof.
In another example embodiment, one or more (e.g., 2, 3, 4, 5, or 6) chelate-metal complexes are linked to a TBM that has high affinity for fibrin. For example, one such chelate-metal complex has the formula shown below
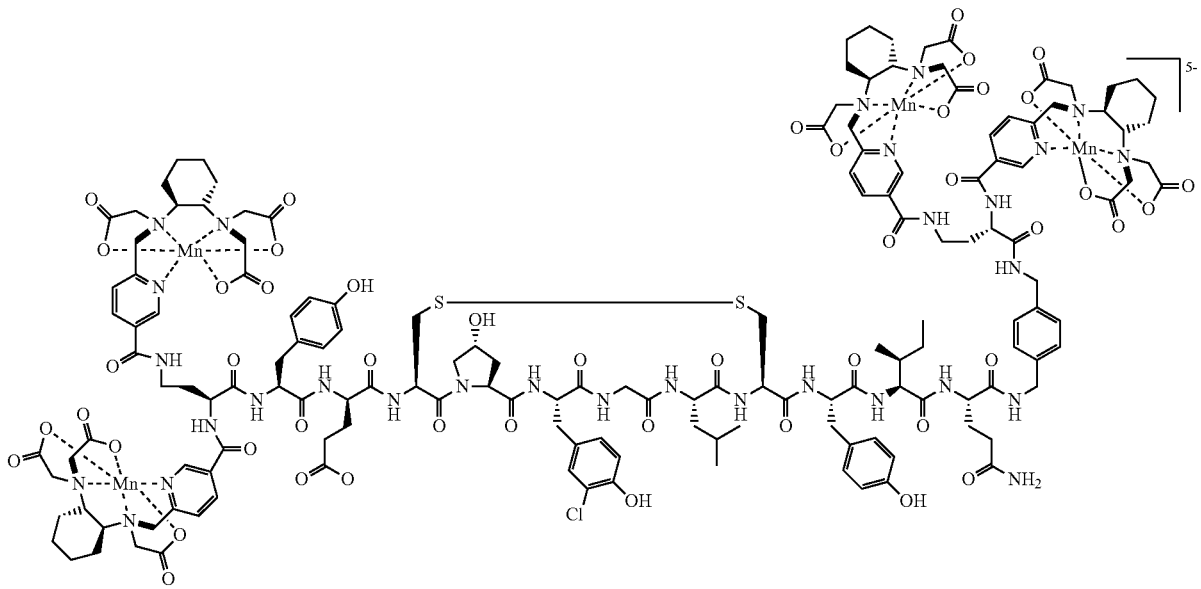
or a pharmaceutically acceptable salt thereof.

In another embodiment, one or more (e.g., 2, 3, 4, 5, or 6) chelate-metal complexes are linked to a TBM that has high affinity for collagen. For example, one chelate-metal complex has the formula shown below:

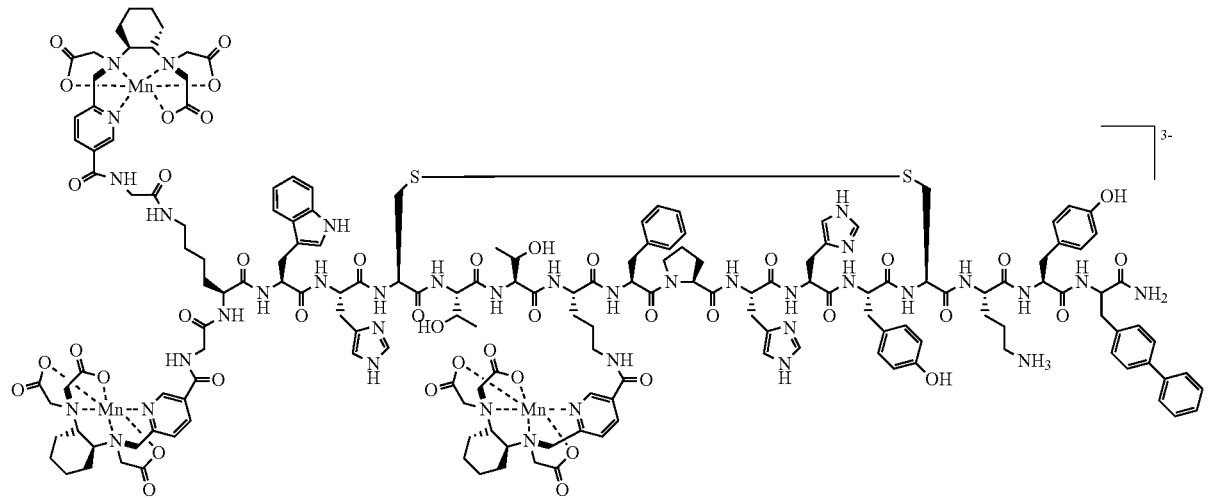

or a pharmaceutically acceptable salt thereof.

In another embodiment, the chelating ligand linked to a TBM that has high affinity for protein carbonyls, such as hydrazides. For example, one chelating ligand has the formula shown below

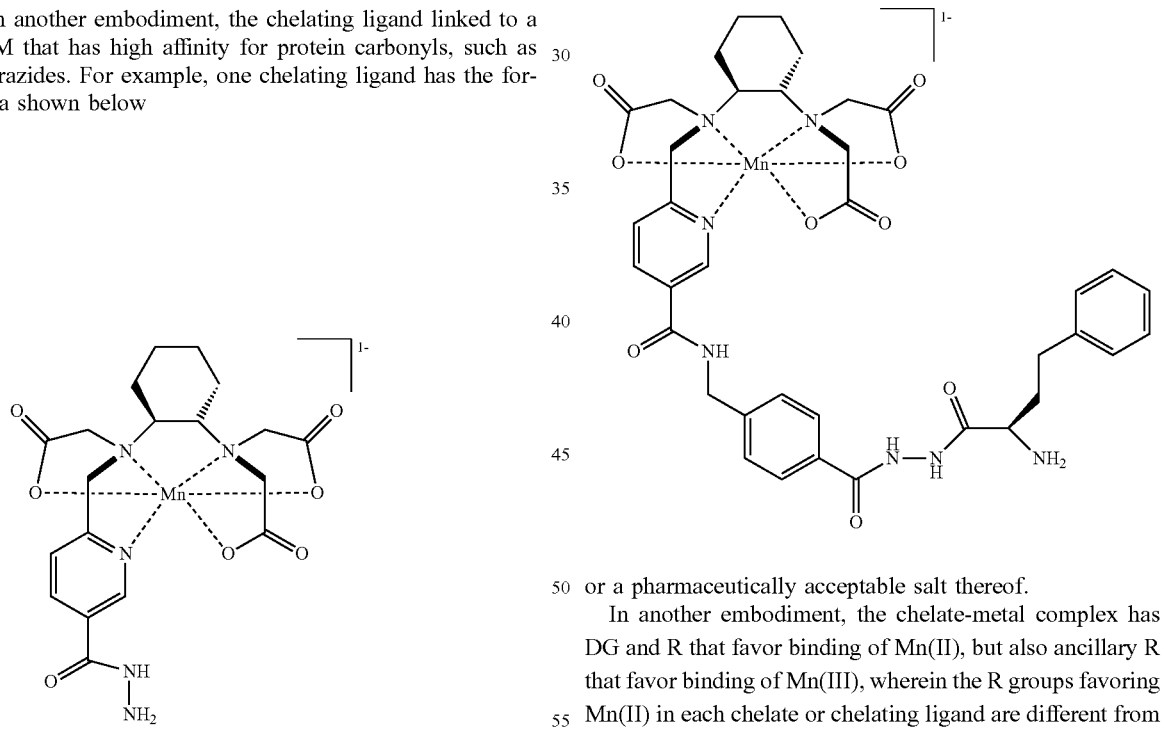

or a pharmaceutically acceptable salt thereof.

In another embodiment, the chelating ligand linked to a TBM that has high affinity for elastin. For example, one chelating ligand has the formula shown below or a pharmaceutically acceptable salt thereof.

In another embodiment, the chelate-metal complex has DG and R that favor binding of Mn(II), but also ancillary R that favor binding of Mn(III), wherein the R groups favoring Mn(II) in each chelate or chelating ligand are different from those that favor Mn(III), For example in formula XIX, when M=Mn, R groups that favor Mn(II) can be independently selected from COOH, $PO_3H_2$, or formula XVI where X=N, while those that favor Mn(III) can be independently selected from formula XVI where X=C(OH). Upon oxidation of MOW to the R groups that favor Mn(III) bind to the oxidized Mn(III) ion. Switching from Mn(II) to Mn(III) results in decreased relaxivity.

In one example embodiment, the chelate-metal complex has the formula shown below

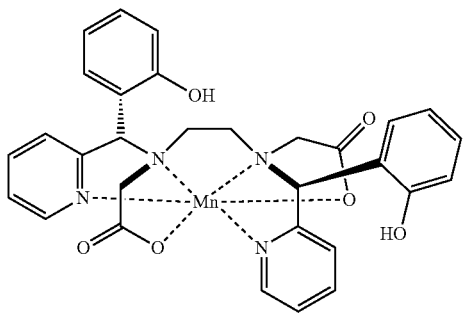

or a pharmaceutically acceptable salt thereof.

In another example embodiment, the chelate-metal complex has the formula shown below

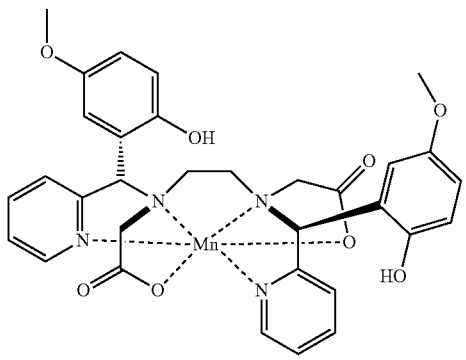

or a pharmaceutically acceptable salt thereof.

In another example embodiment, the chelate-metal complex has the formula shown below

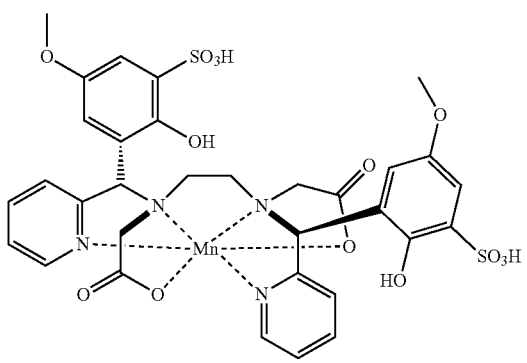

or a pharmaceutically acceptable salt thereof

In another example embodiment, the chelate-metal complex has the formula shown below

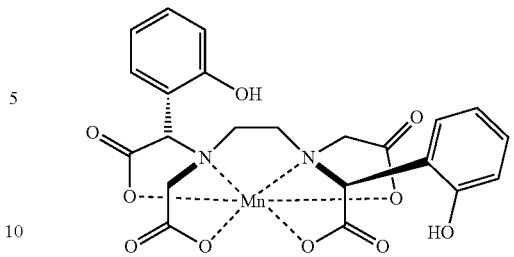

or a pharmaceutically acceptable salt thereof

In another example embodiment, the chelate-metal complex has the formula shown below

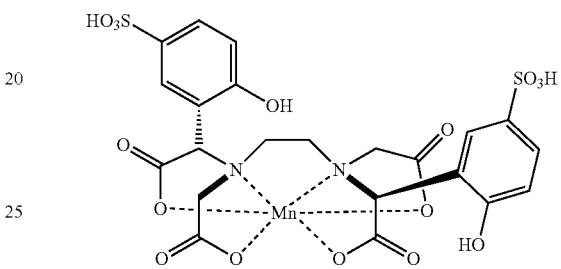

or a pharmaceutically acceptable salt thereof

In another example embodiment, the chelate-metal complex has the formula shown below

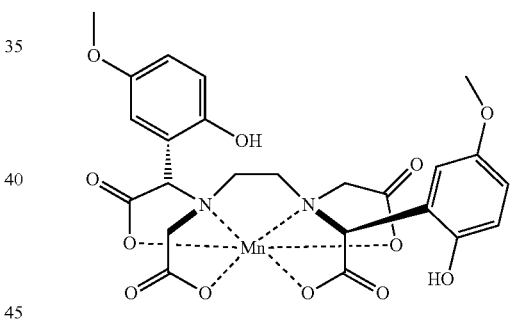

or a pharmaceutically acceptable salt thereof.

In another example embodiment, the chelate-metal complex has the formula shown below

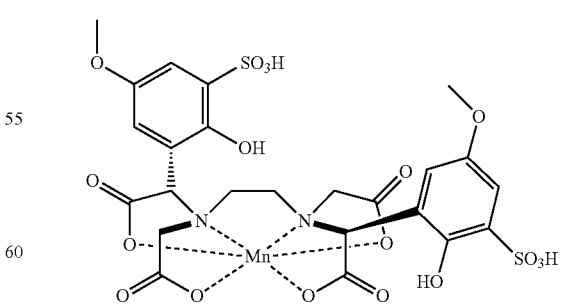

or a pharmaceutically acceptable salt thereof

In a related fashion, the chelate-metal complex has DG and R that favor binding of Mn(III), but also ancillary R that favor binding of Mn(II), wherein the R groups favoring Mn(III) in each chelate or chelating ligand are different from those that favor Mn(II). For example, when M=Mn, $R^4$ groups that favor Mn(III) can be independently selected from formula XVI where X=((OH), while $R^3$ groups that favor Mn(II) can be independently selected from COOH, $PO_3H_2$, or formula XVI where X=N. Upon reduction of Mn(III) to Mn(II), the R groups that favor Mn(II) bind to the reduced Mn(II) ion. Switching from Mn(III) to Mn(II) results in increased relaxivity.

In one example embodiment, the chelate-metal complex has the formula shown below

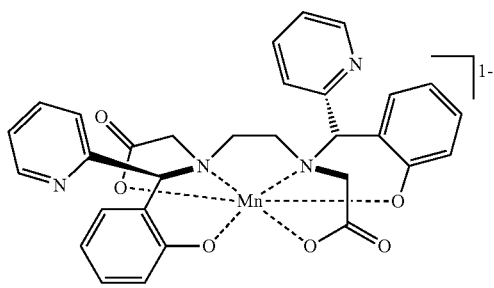

or a pharmaceutically acceptable salt thereof.

In another example embodiment, the chelate-metal complex has the formula shown below

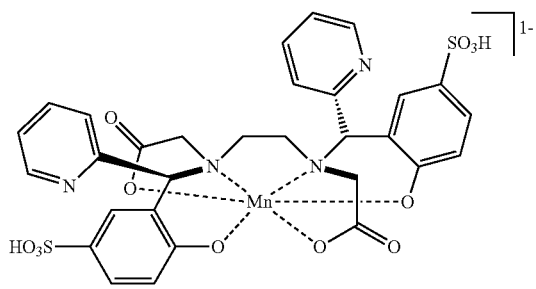

or a pharmaceutically acceptable salt thereof

In another example embodiment, the chelate-metal complex has the formula shown below

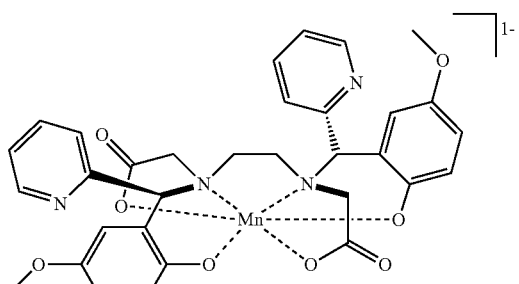

or a pharmaceutically acceptable salt thereof

In another example embodiment, the chelate-metal complex has the formula shown below

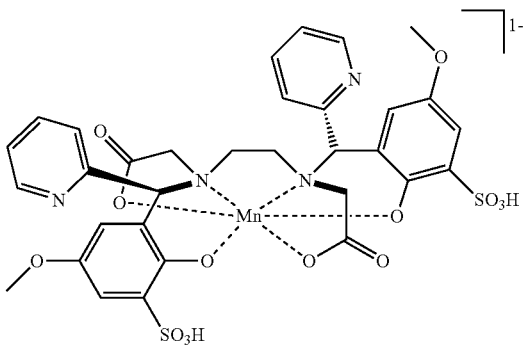

or a pharmaceutically acceptable salt thereof

In another example embodiment, the chelate-metal complex has the formula shown below

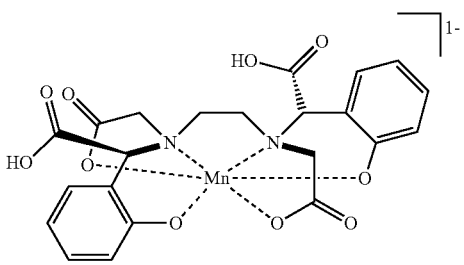

or a pharmaceutically acceptable salt thereof

In another example embodiment, the chelate-metal complex has the formula shown below

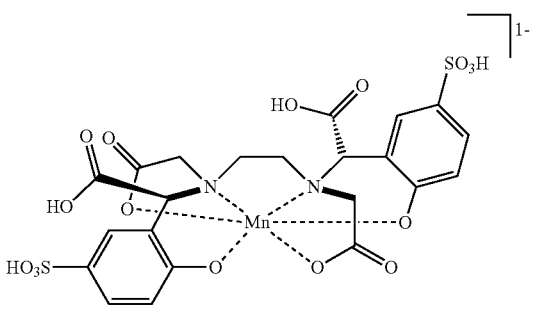

or a pharmaceutically acceptable salt thereof

In another example embodiment, the chelate-metal complex has the formula shown below

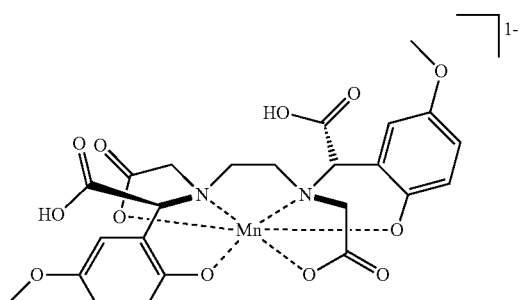

or a pharmaceutically acceptable salt thereof

In another example embodiment, the chelate-metal complex has the formula shown below

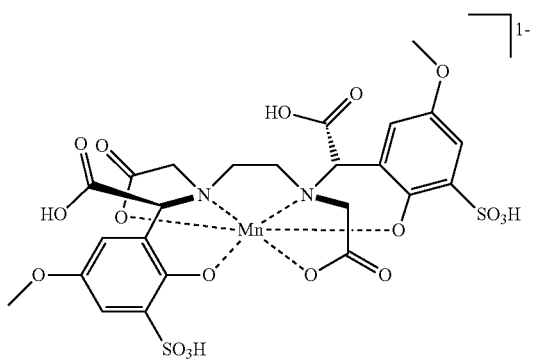

or a pharmaceutically acceptable salt thereof.

Chelate-metal complexes that can toggle between the Mn(II) and Mn(III) oxidation states can be turned "on" and "off" in response to biochemical stimuli. For example, the compound can be a compound in which the Mn ion is in the Mn(II) oxidation state, as shown in the formula below

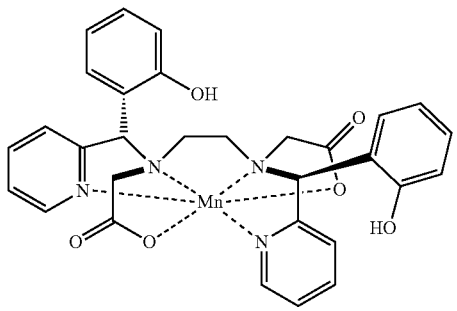

or a pharmaceutically acceptable salt thereof.

The compound Mn(II) complex, upon reduction, can be a compound in which the Mn ion is in the Mn(III) oxidation state:

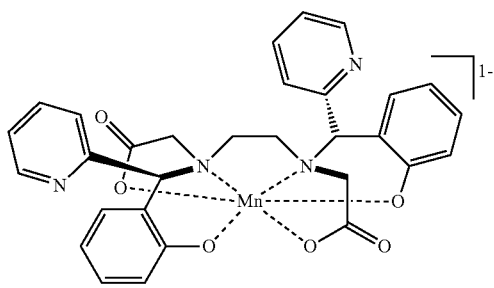

or a pharmaceutically acceptable salt thereof. Such contrast agents that can change their relaxivity and signal generating properties in response to an oxidizing or reducing stimulus can be used to detect regions of oxidative stress occurring in the body, for instance due to myocardial ischemia in the context of acute coronary syndrome or myocardial infarction; or in stroke; or in inflammation; or in nonalcoholic steatohepatitis; or in inflammatory bowel disease; or in multiple sclerosis; or in high risk atherosclerotic plaque; or in other diseases characterized by tissue or organ ischemia; or in diseases of chronic inflammation such as rheumatoid arthritis or lupus. Proliferating cancer cells require a more reducing environment than normal cells and thus these contrast agents may be useful in distinguishing cancerous tissue from normal tissue, or be used to stage the aggressiveness of a specific cancer.

The synthetic protocols used to the prepare chelating ligands are general and can be broadly extended to include additional embodiments Targeting Groups Chelating ligands may be modified to incorporate one or more Target Binding Moieties (TBM), as indicated above. TBMs can include peptides, nucleic acids, or small organic molecules, examples of which are provided below. TBMs allow chelating ligands and metal chelates to be bound to targets in vivo. Typically, a TBM has an affinity for a target. For example, the TBM can bind its target with a dissociation constant of less than 10 µM, or less than 5 µM, or less than 1 µM, or less than 100 nM. In some embodiments, the TBM has a specific binding affinity for a specific target relative to other physiologic targets. For example, the TBM may exhibit a smaller dissociation constant for fibrin relative to its dissociation constant for collagen. Some TBMs do not necessarily adhere to a target, but promote a change in relaxivity of the contrast agent in the presence of a specific target. For example, a TBM may promote a change in relaxivity in the presence of reactive oxygen species (ROS) generated by peroxidase enzymes.

TBMs can be synthesized and conjugated to the chelating ligands by methods well-known in the art, including standard peptide and nucleic acid synthesis methods. (see, e.g., WO 01/09188, WO 01/08712, and U.S. Pat. Nos. 6,406,297 and 6,515,113, all of which are incorporated by reference in their entireties). In some embodiments, a TBM is covalently bound to the chelating ligand. For example, the TBM can be covalently bound to the chelating ligand through an optional Linker (L). As indicated in the structures above, a TBM can be anywhere on a chelating ligand. For example, the TBM can be bound, optionally via an L, to any Rs or DG. In some embodiments, incorporating multiple TBMs onto the chelating ligand can result in higher affinity and avidity for the target. Chelating ligands will typically contain 1-4 (L-TBM) units, for example a chelating ligand can be bound to one L-TBM, or a chelating ligand can be bound to two L-TBM units, or a chelating ligand can be bound to three L-TBM units, or a chelating ligand can be bound to four L-TBM units. In other embodiments it may be preferable to bind multiple chelating ligands to one or more L-TBM units in order to increase the MR signal generating capability of the contrast agent. In such embodiments a contrast agent will typically contain 1-4 (L-TBM) units bound to 2-8 chelating ligands, for example two chelating ligands can be bound to one L-TBM, or three chelating ligands can be bound to one L-TBM, or four chelating ligands can be bound to one L-TBM, or six chelating ligands can be bound to one L-TBM, or eight chelating ligands can be bound to one L-TBM.

Chelating ligands having a TBM can be assayed for relaxivity values (as the metal chelate) in the presence or absence of the target, e.g., when the TBM is bound or unbound to the target, respectively. Typically, a metal chelate having a TBM will exhibit a higher relaxivity when bound to a target because of the RIME effect (see, e.g., U.S. Pat. Nos. 4,899,755 and 4,880,008, both of which are incorporated by reference in their entireties).

Typical targets include human serum albumin (I-ISA), fibrin, an extracellular component of myocardium (e.g., collagen, elastin, and decorin), extracellular enzymes secreted in inflammation or cancer (e.g. peroxidase or protease enzymes), or an extracellular component of a lesion (e.g., hyaluronic acid, heparin, chondroitin sulfate, dermatan sulfate, heparan sulfate, keratin sulfate, versican, biglycan, dysregulated thiol/disulfide composition).

TBMs for binding to HSA are well known in the art, and can include a variety of hydrophobic or amphiphilic moieties. For example, a TBM for binding HSA can have one of the following formulas:

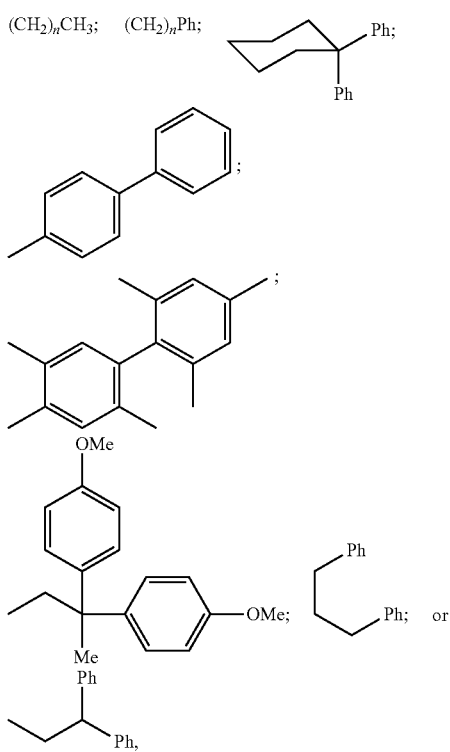

where n is 2 to 20 and Ph is phenyl (see, for example, WO 96/23526).

Useful TBMs for binding fibrin are described in U.S. patent application Ser. No. 10/209,183, entitled PEPTIDE-BASED MULTIMERIC TARGETED CONTRAST AGENTS, filed Jul. 30, 2002, which is incorporated by reference in its entirety. For example, fibrin binding peptides may be chosen from the cyclic, disulfide bridged peptide, C-P*-Y*-X-L-C (SEQ ID NO:1) where P* is proline or its derivative 4-hydroxyproline, Y* is tyrosine or its non-natural derivative substituted at the 3-position with a moiety from the group of F, Cl, Br, I, or $NO_2$, and X is either glycine or D- or L-aspartic acid. As another example peptides can be chosen from, $X_1$-$X_2$-C-P*-Y*-$X_3$-L-C-$X_4$-$X_5$-$X_6$ (SEQ ID NO:2) where $X_1$ is selected from W, S, F, Y, or substituted Y or substituted F; $X_2$ is selected from E, H, dH, S; $X_3$ is selected from G, D, dD; $X_4$ is selected from H, F, Y, and W; $X_5$ is selected from I, L, V, and N; and $X_6$ is selected from N, Q, I, L, V, or $X_6$ is not present.

TBMs for binding an extracellular component of a lesion include peptides having affinity for Hyaluronic Acid (HA). Peptides that have affinity for HA are known. For example, peptides that bind to HA from a random 12-mer phage peptide library have been isolated (see e.g., Mummert, M., Mohamedzadeh, M., Mummert, D., Mizumoto, N., and Takashima, A. J., Exp. Med. (2000) 769-779, which is incorporated by reference in its entirety). One of these peptides, GAHWQFNALTVR (SEQ ID NO:3), binds to HA with Kd~1 µM. As described herein, all peptides are written from their N to their C terminus. Other HA binding peptides include TSYGRPALLPAA (SEQ ID NO:4), MDHLAPTRFRPAI (SEQ ID NO:5), TLRAIWPMWMSS (SEQ ID NO:6), and IPLTANYQGDFT (SEQ ID NO:7).

In addition, peptides having affinity for HA can include a consensus binding motif found in many HA-binding peptides, including RHAMM, CD44, and the link protein. The consensus motif can be $B(X)_7$, where B is a basic residue (e.g., Lys, His or Arg) and X is a non-acidic residue.

In other embodiments, a lesion-targeting peptide can have affinity for heparin, and can include a heparin-binding motif found in heparin-binding proteins. Heparin-binding motifs for inclusion in the peptides include XBBXBX or XBBBXXBX, where B is a basic residue (e.g., Lys, His, or Arg) and X is a non-acidic residue. For example, the heparin-binding peptide ACQWHRVSVRWG (SEQ ID NO:8) conforms to the XBBXXXBX sequence (see e.g., Nielsen, P. K., Gho, Y. S., Hoffman, M. P., Watanabe, H., Makino, M., Nomizu, M., and Yamada, Y. J. Biol. Chem. (2000) 275, 14517-14523, which is incorporated by reference in its entirety). Finally, the heparin sulfate/heparin interacting protein sequence (HIP) motif can also be included in a peptide. One example of such a motif is CRPKAKAKAKAKDQTK (SEQ ID NO:9).

In other embodiments, a lesion-targeting peptide can have affinity for proteolyzed fragments of transmembrane proteins such as receptor protein tyrosine phosphatase (PTPµ) (see e.g., Burden-Gully, S. M., Zhou, Z., Craig, S. E. L., Lu, Z.-R., Brady-Kalnay, S. M. Transl. Oncol. (2013) 6, 329-337). One example of such a motif is CGEGDDFNWEQVNTLTKPTSD (SEQ ID NO:10).

In other embodiments, a lesion-targeting peptide can have affinity for fibronectin (see e.g. Zhou, Z., Qutaish, M. Han, Z. Schur, R. M., Liu, Y., Wilson, D. L., and Lu, Z.-R. Nat. Commun. (2015) 6, 7984-7994). One example of such a motif is CREKA (SEQ ID NO;

Useful TBMs for targeting fibrin include fibrin binding peptides to allow for specific imaging of fibrin (e.g., thrombi, solid tumors, and atherosclerotic plaques) within a mammal. Any peptide capable of binding fibrin may be used. For example, the peptides disclosed in WO 2008/071679, U.S. Pat. Nos. 6,984,373; 6,991,775; and 7,238,341 and U.S. Patent Application No. 2005/0261472 may be used, all of which are incorporated by reference in their entireties. A peptide can be from about 2 to about 25 amino acids in length (e.g., about 3 to about 20, about 5 to about 18, about 8 to about 15, and about 10 to about 14).

Useful TBMs for targeting enzymes secreted in inflammation and cancer include 5-hydroxytryptamine, shown below

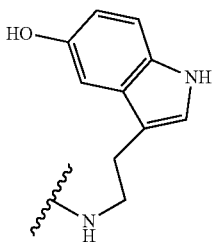 [SMILES: *NCCc1c[nH]c2ccc(O)cc12]

and 5-hydroxytryptophan, shown below,

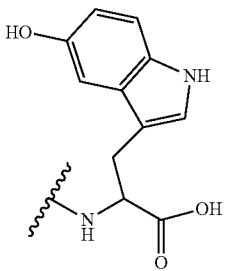 [SMILES: *NC(Cc1c[nH]c2ccc(O)cc12)C(=O)O]

which are oxidized and subsequently oligomerize in the presence of ROS generated by peroxidase enzymes such as myeloperoxidase (see e.g. Shazeeb, M. S., Xie, Y., Gupta, S., and Bogdanov, A. A. Jr., Mol. Imaging. (2012) H, 433-443, which is incorporated by reference in its entirety). The oligomerization results in larger, more slowly tumbling chelates that have higher relaxivity.

In other embodiments, ROS targeting moieties can include DGs or R groups that can be oxidized by biological oxidizing agents such as oxygen, hydrogen peroxide, superoxide, peroxidase enzymes, hypochlorous acid, or disulfides. In the absence of the oxidizing agent, the DG or R group favors the formation of a metal chelate with the metal ion in a high-valent oxidation state such as Mn(III). When the DG or R group is oxidized, then the oxidized DG or R group now favors the formation of a metal chelate with the metal ion in a low-valent oxidation state such as Mn(II). Switching from Mn(III) to Mn(II) results in increased relaxivity.

In other embodiments, metal-chelates that comprise R groups and DGs that favor, and are bound to, metal ions in low-valent oxidation states such as Mn(II) can include ancillary, non-coordinating R groups that favor binding to high-valent metal oxidation states such as Mn(III). Such ancillary R groups can bind to and trap Mn(III) generated from oxidation of Mn(II) by biological oxidizing agents such as oxygen, hydrogen peroxide, superoxide, peroxidase enzymes, hypochlorous acid, or disulfides. Switching from Mn(II) to Mn(III) results in decreased relaxivity.

In other embodiments, metal-chelates that comprise R groups and DGs that favor, and are bound to, metal ions in high-valent oxidation states such as Mn(III) can include ancillary, non-coordinating R groups that favor binding to low-valent metal oxidation states such as Mn(II). Such ancillary R groups can bind to and trap Mn(II) generated from reduction of Mn(II) by biological reducing agents such as thiols, ascorbic acid, mitochondria, superoxide, reductase enzymes, NADH, or NADPH. Switching from Mn(III) to Mn(II) results in increased relaxivity.

Useful TBMs for targeting enzymes secreted in inflammation and cancer can include peptidic substrates for protease enzymes (see Jastrzebska, B., Lebel, R., Therriault, H., McIntyre, J. O., Escher, E., Guerin, B., Paquette, B., Neugebauer, W. A., and Lepage, M. J. Med. Chem. (2009) 52, 1576-1581, which is incorporated by reference in its entirety). Activity of the protease enzyme on the peptidic substrate can effect a change in solubility of the chelate-metal complex. Decreased solubility results in in vivo retention at the site of the biochemical target.

Useful TBMs for targeting collagen include peptides derived from the propolypeptide of von Willebrand factor, which is known to bind collagen. As used herein, all peptides are written from the N to C terminus. Additionally, peptides containing two or more cysteine residues can form disulfide bonds under non-reducing conditions. A peptide for targeting collagen can include the following general formula: $X_1$-$X_2$-$X_3$-$X_4$-$X_5$-$X_6$-$X_7$-$X_8$-$X_9$-$X_{10}$ (SEQ ID NO:12) where $X_1$ can be W, C, or A; $X_2$ can be R, C, or A; $X_3$ can be E, C, A, K, or T; $X_4$ can be P, C, or A; $X_5$ can be D, G, S, C, or A; $X_6$ can be F, R, C, or A; $X_7$ can be C, M, or A; $X_8$ can be A, E, or C; $X_9$ can be L, M, R, C, or A; and $X_{10}$ can be S, N, G, L, C, or A; where no more than 3 of $X_1$-$X_{10}$ are C or A, independently, and where the total number of C and A residues in $X_1$-$X_{10}$ is a maximum of 4. For example, a peptide can have the following sequences: WREPSFCALS (SEQ ID NO:13); WREPSFMALS (SEQ ID NO:14); and WREPGFCALS (SEQ ID NO:15).

Another example of a peptide that binds collagen has the following general formula: $X_1$-$X_2$-$X_3$-$X_4$-$X_5$-$X_6$-$X_7$-$X_8$-$X_9$-$X_{10}$-$X_{11}$-$X_{12}$-$X_{13}$ (SEQ ID NO:16) where $X_1$ can be W, C, or A; $X_2$ can be R, C, or A; $X_3$ can be E, C, A, K, or T; $X_4$ can be P, C, or A; $X_5$ can be D, G, S, C, or A; $X_6$ can be F, R, C, or A; $X_7$ can be C, M, or A; $X_8$ can be A, E, or C; $X_9$ can be L, M, R, C, or A; $X_{10}$ can be 5, N, G, L, C, or A; $X_{11}$ can be C, M, or A; $X_{12}$ can be P, A, or C; and where $X_{13}$ can be K, Q, P, G, C, or A; where no more than 4 of $X_1$-$X_{13}$ are C or A, independently, and where the total number of C and A residues in $X_1$-$X_{13}$ is a maximum of 5.

A peptide for binding collagen can also have the following general formula: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ (SEQ ID NO:17) where $X_1$ can be V, I, C, or A; $X_2$ can be A, G, R, D, or C; $X_3$ can be W, C, or A; $X_4$ can be R, C, or A; can be E, C, A, K, or T; $X_6$ can be P, C, or A; $X_7$ can be D, G, S, C, or A; $X_8$ can be F, R, C, or A; $X_9$ can be C, M, or A; $X_{10}$ can be E, A, or C; $X_{11}$ can be L, C, A, M, or R; $X_{12}$ can be S, C, A, N, G, or L; $X_{13}$ can be C, M, or A; $X_{14}$ can be P, A, or C; and $X_{15}$ can be K, Q, P, H, G, C, or A; where no more than 4 of $X_1$-$X_{15}$ are C or A, independently, and where the total number of C and A residues in $X_1$-$X_{15}$ is a maximum of 6.

Further peptides for targeting collagen can be found in U.S. Pat. No. 8,034,898, entitled "Methods of Collagen Imaging", filed Dec. 29, 2006, which is incorporated by reference in its entirety. For example, collagen binding peptides can be selected from cyclic, disulfide bridged peptides W-H-C-$X_1$-T-$X_2$-F-P-H-H-Y-C (SEQ NO:18) where $X_1$ is selected from Y, T, or S, and $X_2$ can be any amino acid. Other peptides for targeting collagen can be identified by modifying (e.g., mutating, truncating, lengthening) the peptides described above.

Useful TBMs for binding folate receptors, vitronectins, alpha-v-beta-3 and alpha-v-beta-5 integrins, RGD peptides for MMP targets, porphyrins, and phosphonates are described in WO 2004/112839, filed Jun. 17, 2004, which is incorporated by reference in its entirety, and references therein.

Useful TBMs for binding elastin include the following formula:

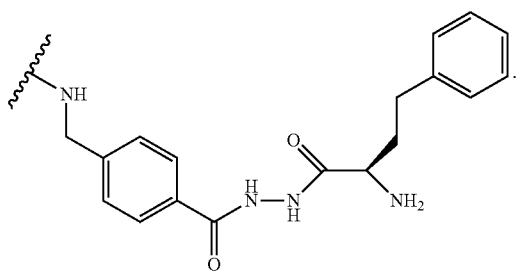 [SMILES: *NCc1ccc(C(=O)NNC(=O)[C@H](N)CCc2ccccc2)cc1]

Self-Assembling Moieties

Magnetic resonance imaging of low concentration targets can be limited by the relaxivity of the contrast agent. Different strategies have been employed to assemble many chelates together to improve the sensitivity of the contrast agent including covalent and non-covalent assembly of chelating ligands and metal chelates. The non-covalent approach involves using a group that can interact with itself or similar groups to form an assembly of molecules. Chelating ligands may be modified to incorporate one or more Self-Assembling Moieties (SAM), as indicated above. SAMs can include lipids, long chain alkyl or substituted alkyl groups, perfluorocarbons, peptides, nucleic acids, or small organic molecules. SAMs allow chelating ligands and metal chelates to associate with themselves to form larger aggregates, particles, or assemblies.

SAMs can be synthesized and conjugated to chelating ligands by methods well known in the art, including standard peptide and nucleic acid synthesis methods; see, e.g., WO 01/09188, WO 01/08712, and U.S. Pat. Nos. 6,406,297 and 6,515,113, all of which are incorporated by reference in their entirety. Typically, a SAM is covalently bound to a chelating ligand, and can be covalently bound to a chelating ligand through an optional Linker (L). As indicated in the structures above, a SAM may be anywhere on a chelating ligand. For example, the SAM may be bound, optionally via an L, to any Rs or DG.

Chelating ligands having a SAM can be assayed for relaxivity values (as the metal chelate) at or above a critical self-assembly concentration. At very low concentrations the chelate may exist in predominantly monomeric, unassembled form; above a critical self-assembly concentration the chelate may exist predominantly in the self-assembled form. Typically, a metal chelate having a SAM will exhibit a higher relaxivity when in the self-assembled form because of the RIME effect (see, e.g., U.S. Pat. Nos. 4,899,755 and 4,880,008, both of which are incorporated by reference in their entirety).

SAMs can include lipids and lipid-like groups capable of forming micelles (see e.g., Nicolle, G. M., Toth, E., Eisenwiener, K. P., Macke, H. R., and Merbach, A. E. *J Biol Inorg Chem.* 2002 7:757-69, which is incorporated by reference in its entirety) or liposomes (see e.g., Mulder, W. J., Strijkers, G. J., van Tilborg, G. A., Griffioen, A. W., and Nicolay, K., NMR *Biomed.* 2006 19:142-64, which is incorporated by reference in its entirety). SAMs can also facilitate incorporation into mixed liposomes or emulsions e.g., U.S. Pat. No. 6,869,591, which is incorporated by reference in its entirety)

SAMs can also be perfluoroalkyl groups that promote self-assembly (see e.g., U.S. Pat. No. 6,916,461 and WO 2003/0232012, both of which are incorporated by reference in their entirety). Alternatively, peptides can also form self-assemblies (see e.g., WO 2004/0204561, which is incorporated by reference in its entirety, and peptide sequences disclosed therein).

Linkers

In some embodiments, the TBM is covalently bound to the chelating ligand through a linker (L). L can include, for example, a linear, branched or cyclic peptide sequence. In one embodiment, an L can include the linear dipeptide sequence G-G (glycine-glycine). In embodiments where the TBM includes a peptide, the L can cap the N-terminus of the TBM peptide, the C-terminus, or both N- and C-termini, as an amide moiety. Other exemplary capping moieties include sulfonamides, ureas, thioureas and carbamates. Linkers can also include linear, branched, or cyclic alkanes, alkenes, or alkynes, and phosphodiester moieties. L may be substituted with one or more functional groups, including ketone, ester, amide, ether, carbonate, sulfonamide, or carbamate functionalities. Specific linkers contemplated include —(O—(CH$_2$)$_2$—O)n, where n=1-20,000, and more specifically where n=1-6; NH—CO—NH—; —CO—(CH$_2$)$_n$—NH—, where n=1 to 10; dpr; dab; —NH-Ph-; —NH—(CH$_2$)$_n$—, where n=1 to 10; —CO—NH—; where n=1 to 10; —CO—(CH$_2$)$_n$—NH—, where n=1 to 10; —CS—NH—, and

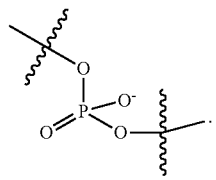 [SMILES: *OP(=O)([O-])O*]

In some embodiments, L is linked to the chelate via any R or DG. For example, a chelate may have the general formula:

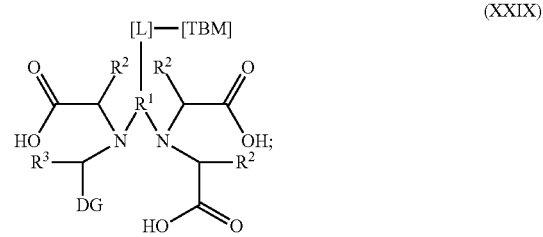

(XXIX)

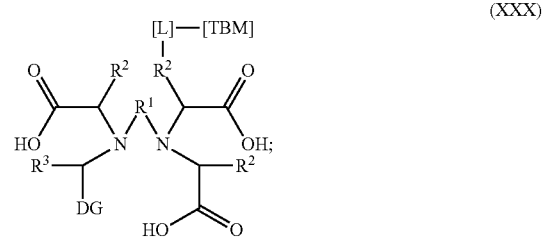

(XXX)

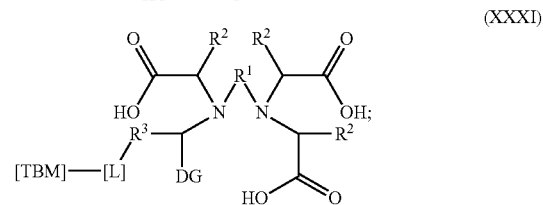

(XXXI)

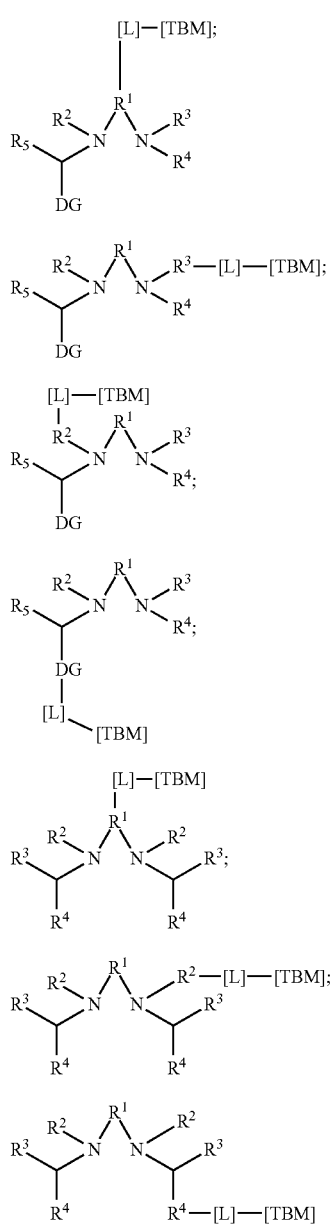

or a pharmaceutically acceptable salt thereof.

Additional examples of linkers and synthetic methodologies for incorporating them into chelating ligands, particularly chelating ligands comprising peptides, are set forth in WO 01/09188, WO 01/08712, WO 2004/112839, U.S. patent application Ser. No. 10/209,183, entitled "Peptide-Based Multimeric Targeted Contrast Agents," filed Jul. 30, 2002, and U.S. patent application Ser. No. 11/618,564, entitled "COLLAGEN BINDING PEPTIDES," filed Dec. 29, 2006, all of which are incorporated by reference in their entireties.

Properties of Chelating Ligands and Metal Chelates

Chelating ligands are capable of binding one or more metal ions to result in a metal chelate. Metal chelates can be prepared by methods well known in the art; see e.g., WO 96/23526, U.S. Pat. Nos. 6,406,297 and 6,515,113, all of which are incorporated by reference in their entireties, and Examples, below.

Metal chelates can include a metal ion with an atomic number of 21-29, 40, 42, or 57-83. For example, metal chelates can include a stable or unstable isotope selected from Gd(III), Fe(III), Mn(II), Mn(III), Cr(III), Cu(II), Cu(III), Dy(III), Ho(III), Er(III), Pr(III), Eu(II), Eu(III), Nd(III), La(III), Lu(III), Sm(III), Tb(III), Tb(IV), Tm(III), Y(III), In(III), Ga(III), Tc(III), Tc(IV), Tc(V), Re(III), Re(IV), Re(V), Bi(III), or Yb(III). The metal ion can be paramagnetic. Typically, because of the chemical nature and number of DGs on the chelating ligands, the metal ion is tightly bound by the chelating ligand, and physiologically compatible metal chelates can be made. The formation constant, $K_f$, of a chelating ligand for a metal ion is an indicator of binding affinity, and is typically discussed with reference to a log $K_f$ scale. Physiologically compatible metal chelates can have a log $K_f$ ranging from 10 to about 25, i.e. $K_f$ ranges from $10^{10}$ to $10^{25}$ $M^{-1}$. For Mn(II) metal chelates, the log $K_f$ should be greater than 12. Methods for measuring $K_f$ are well known in the art; see, e.g., Martell. A. E, and Motekaitis, R. J., *Determination and Use of Stability Constants,* 2d Ed., VCH Publishers, New York (1992), which is incorporated by reference in its entirety.

The relaxivity values of metal chelates can also be assessed. If the metal chelate incorporates a TBM, the relaxivity can be measured in the presence and absence of the target molecule. Methods for measuring relaxivity are well known in the art; see e.g., WO 96/23526, which is incorporated by reference in its entirety.

One challenge in identifying new high relaxivity chelates is the fact that for most metal chelates, the relaxivity observed is limited by the tumbling rate (rotational diffusion) of the chelate. This is well documented in reviews such as R. B. Lauffer, *Chem. Rev.* 1987, 87:901-27 and P. Caravan et al., *Chem. Rev.* 1999, 99:2293-2352, which is incorporated by reference in its entirety. The effect of many of the parameters listed above (e.g., water residency time and second sphere effect) are not pronounced for low (<1500 Da) molecular weight metal complexes. When metal chelates tumble slowly, either by binding to large molecules like proteins, linking to polymeric structures, or self-assembling into large aggregates, the effect of these other parameters can be observed. Therefore, one way to identify metal chelates capable of very high relaxivities is to screen the chelates for relaxivity under conditions where rotational diffusion is slow.

One way to do this is to incorporate into each chelate that is to be tested, a common TBM or SAM group. By comparing chelates that have a common TBM in the presence of the target protein (e.g., albumin), it is possible to rank the chelates in order of highest to lowest relaxivity and determine which donor groups and SSMs are the most favorable combination. The high relaxivity chelates identified in this way can be further modified to incorporate a different TBM.

Metal chelates can also be evaluated for the mean residence time of water molecule(s) in the first (or higher) coordination sphere(s). The mean residence time of water molecules is the inverse of the water exchange rate and is dependent on temperature. The mean residence time of water in the coordination sphere of the metal chelates at 37° C. can be between 1 and 100 ns. In some embodiments, the mean residence time of water in the coordination sphere of the metal chelates at 37° C. is between 3 and 30 ns. $^{17}O$ NMR can be used to evaluate the mean residence time of water molecules. See, e.g., Example 7, below.

Luminescence lifetime measurements can be used to evaluate the number of water molecules bound to a metal chelate. Methods for measuring luminescence lifetimes are known in the art, and typically include monitoring emissive transitions of the chelate at particular wavelengths for lifetime determination, followed by fitting of luminescence decay data. Luminescence lifetime measurements are also useful for evaluating the suitability of the metal chelates as luminescent probes. Alternatively $^{17}$C NMR can be used for Mn(II) chelates (see Gale E M, Zhu J, Caravan P. Direct Measurement of the Mn(II) Hydration State in Metal Complexes and Metalloproteins through $^{17}$C NMR. Line Widths. J Am Chem Soc 2013; 135:18600-18608, which is incorporated by reference in its entirety).

Use of Chelating Ligands and Metal Chelates

Chelating ligands can be used to prepare metal chelates, as described above, for diagnostic purposes. For example, metal chelates prepared with Mn(II) can be useful as contrast agents in MR imaging. Contrast agents incorporating a TBM can bind a target and therefore can be particularly useful in targeted MR applications, e.g., to image blood flow, clots, lesions, or the myocardium. In some embodiments, at least about 10% at least about 50%, about 80%, about 90%, about 92%, about 94%, or about 96%) of the contrast agent can be bound to the desired target at physiologically relevant concentrations of contrast agent and target. The extent of binding of a contrast agent to a target can be assessed by a variety of equilibrium binding methods, e.g., ultrafiltration methods; equilibrium dialysis; affinity chromatography; or competitive binding inhibition or displacement of probe compounds.

Contrast agents can exhibit high relaxivity as a result of target binding, which can lead to better MR image resolution. In some embodiments, the increase in relaxivity upon binding is at least about 1.5-fold (e.g., at least a 2, 3, 4, 5, 6, 7, 8, 9, or 10-fold increase in relaxivity) as compared to the chelate-metal complex not bound to the target or existing in a different oxidation state. For example, a targeted contrast agents can have a 7 to 8-fold, 9 to 10-fold, or even greater than 10-fold increase in relaxivity as compared to the chelate-metal complex not bound to the target or existing in a different oxidation state. In some embodiments, the relaxivity of an MRI contrast agent as provided herein at 60 MHz and 37° C. is at least 8 mM$^{-1}$s$^{-1}$ per paramagnetic metal ion (e.g., at least 10, 15, 20, 25, 30, 35, 40, or 60 mM$^{-1}$s$^{-1}$ per paramagnetic metal ion). For example, the contrast agents provided herein can have a relaxivity greater than 10 mM$^{-1}$s$^{-1}$ at 60 MHz and 37° C.

Metal chelates of lanthanides can also be useful as luminescent probes. Luminescent metal chelate probes can be useful in a variety of assays, e.g., to detect, separate, and/or quantify chemical and biological analytes in research and diagnostic applications, including high-throughput, real-time, and multiplex applications. For example, probes incorporating a TBM can bind to a target analyte of interest, and can have long luminescent lifetimes (e.g., greater than 0.1 μs, or 100 μs, or 1 ms), thereby improving sensitivity and applicability of various assay formats. See, generally, U.S. Pat. Nos. 6,406,297 and 6,511,113, for a description of assays suitable for inclusion of luminescent metal chelate probes, both of which are incorporated by reference in their entireties. Luminescent metal chelate probes are particularly useful in immunoassays and real-time PCR detection assays.

Use of MRI Contrast Agents

MRI contrast agents may be used in the same manner as conventional MRI contrast agents. For example, an effective amount of the contrast agent is administered to a patient (e.g., an animal, such as a human) and an NM image of the patient is acquired. In embodiments having a TBM, a contrast-enhancing imaging sequence that preferentially increases a contrast ratio of a magnetic resonance signal of the target having a contrast agent bound thereto relative to the magnetic resonance signal of background blood or tissue can be used. These techniques include, but are not limited to, black blood angiography sequences that seek to make blood dark, such as fast spin echo sequences; flow-spoiled gradient echo sequences; and out-of-volume suppression techniques to suppress in-flowing blood. These methods also include flow independent techniques that enhance the difference in contrast due to the $T_1$ difference between contrast-enhanced target and blood and tissue, such as inversion-recovery prepared or saturation-recovery prepared sequences that will increase the contrast between the target and background tissues. Methods of preparation for $T_2$ techniques may also prove useful. Finally, preparations for magnetization transfer techniques may also improve contrast with contrast agents.

Methods may be used that involve the acquisition and/or comparison of contrast-enhanced and non-contrast images and/or the use of one or more additional contrast agents. The additional contrast agents can exhibit affinity for a target. Exemplary methods as set forth in U.S. patent application Ser. No. 09/778,585, entitled MAGNETIC RESONANCE ANGIOGRAPHY DATA, filed Feb. 7, 2001 and U.S. patent application Ser. No. 10/209,416, entitled SYSTEMS AND METHODS FOR TARGETED MAGNETIC RESONANCE IMAGING OF THE VASCULAR SYSTEM, filed Jul. 30, 2002, both of which are incorporated by reference in their entireties.

Contrast agents can be formulated as a pharmaceutical composition in accordance with routine procedures. As used herein, the contrast agents can include pharmaceutically acceptable derivatives thereof. "Pharmaceutically acceptable" means that the agent can be administered to an animal without unacceptable adverse effects. A "pharmaceutically acceptable derivative" means any pharmaceutically acceptable salt, ester, salt of an ester, or other derivative of a contrast agent or compositions that, upon administration to a recipient, is capable of providing (directly or indirectly) a contrast agent or an active metabolite or residue thereof. Other derivatives are those that increase the bioavailability when administered to a mammal (e.g., by allowing an orally administered compound to be more readily absorbed into the blood) or that enhance delivery of the parent compound to a biological compartment (e.g., the brain or lymphatic system) thereby increasing the exposure relative to the parent species. Pharmaceutically acceptable salts of the contrast agents include counter ions derived from pharmaceutically acceptable inorganic and organic acids and bases known in the art, including, without limitation, sodium, calcium, and N-methyl-glucamine.

Pharmaceutical compositions can be administered by any route, including both oral and parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, contrast agents can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g., in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions comprise the contrast agents and pharmaceutically acceptable salts thereof, with any pharmaceutically acceptable ingredient, excipient, carrier, adjuvant or vehicle.

In some embodiments, a contrast agent is administered to the patient in the form of an injectable composition. The method of administering a contrast agent is can include parenterally, meaning intravenously, intra-arterially, intrathecally, interstitially or intracavitarilly. Pharmaceutical compositions can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass.

EXAMPLES

Methods.

General. All chemicals and solvents were purchased commercially and used without further purification.

NMR. NMR spectra were recorded on a 500 MHz Varian spectrometer at 25° C. unless otherwise noted. Chemical shifts are reported in δ (ppm). For $^1$H and $^{13}$C NMR spectra, the residual solvent peaks were used as internal reference except for $^{13}$C NMR recorded in $D_2O$ where dioxane was used as the internal references (Fulmer, *Organometallics* 2010, 29, 2176).[1] Relaxivity measurements were performed on a Bruker mq60 Minispec, 1.41 T and 37° C. Longitudinal (Ti) relaxation was acquired via an inversion recovery experiment using 10 inversion times of duration ranging between $0.05 \times T_1$ and $5 \times T_1$; transverse ($T_2$) relaxation was measured using a Carl-Purcell-Meiboom-Gill spin-echo experiment. Relaxivity $r_{1,2}$) was determined from the slope of a plot of $1/T_{1,2}$ vs. [Mn] for at least 4 concentrations. The transverse ($T_2$) relaxation times of $^{17}O$ were acquired at 11.7 T from the full-width at half-height of the $H_2^{17}O$ signal (Gale, Carvan, *J. Am. Chem. Soc.* 2013, 135, 18600). $^{17}O$ $T_2$ relaxivity ($r_2^O$) was calculated by dividing the Mn-imparted increase in $1/T_2$ relative to neat $H_2O$ (pH 3) by the Mn concentration in mM. 0.7-1.0 mL NMR samples were enriched with a 10 µL of 18% $H_2^{17}O$.

Relaxivity in the presence of fibrin dots. The measurements were performed as previously described (Carvan, *J. Am. Chem. Soc.* 2008, 130, 6025). Briefly, $CaCl_2$ was added to a solution of compound 20, shown below, thrombin and human fibrinogen to trigger fibrin formation (final concentrations of $CaCl_2$, fibrinogen and thrombin were 10 mM, 10 mg/mL and 0.6 U/mL, respectively). The resultant fibrin gels were incubated for 20 min at 37° C. before measurement.

HPLC methods. Liquid chromatography-mass spectrometry (LC-MS) was performed using an Agilent 1100 Series apparatus with an LC/MSD trap and Daly conversion dynode detector with UV detection at 220, 254, and 280 nm. The methods used on this system are as follows: (A1) Kromasil C18 column (100×4.6 mm); eluent C: 90% MeCN/10% 10 mM ammonium acetate, D: 10 mM ammonium acetate; gradient 5% C to 95% C over 14 min; flow rate 0.8 mL/min. Reverse-phase semi-preparative purification was performed on the Rainin Dynamax HPLC system with UV detection from 220 to 280 nm using a Phenomenex C18 or C5 column (250×21.8 cm). The mobile phase A was water with 0.1% TFA added; mobile phase B was MeCN with 0.1% TFA added; mobile phase C was 50 mM ammonium acetate buffer, pH 6.5; mobile phase D was a mixture of 5% 50 mH ammonium acetate buffer, pH 6.5 and 95% MeCN. The methods used for purification are as follows: (P1) starting from 95% A/5% B, the fraction of B increased to 70% over 23 min. The column was washed with 95% B for 2 min and then ramped to 5% B. The system was re-equilibrated at 5% B for 3 min, (P2) starting from 95% C/5% D, the fraction of D increased to 70% over 23 min. The column was washed with 95% D for 2 min and then ramped to 5% B. The system was re-equilibrated at 5% B for 3 min, (P3) starting from 95% A/5% B, the fraction of B increased to 95% over 23 min. The column was washed with 95% B for 2 min and then ramped to 5% B. The system was re-equilibrated at 5% B for 3 min, (P4) starting from 95% C/5% D, the fraction of D increased to 95% over 23 min. The column was washed with 95% D for 2 min and then ramped to 5% D. The system was re-equilibrated at 5% B for 3 min, (P5) starting from 80% A/20% B, the fraction of B increased to 95% over 23 min. The column was washed with 95% B for 2 min and then ramped to 5% B. The system was re-equilibrated at 5% B for 3 min, (P6) starting from 95% A/5% B, the fraction of B increased to 60% over 40 min. The column was washed with 95% B for 2 min and then ramped to 5% B. The system was re-equilibrated at 5% B for 3 min, (P7) starting from 95% C/5D, the fraction of increased to 60% over 23 min. The column was washed with 95% D for 2 min and then ramped to 5% D. The system was re-equilibrated at 5% D for 3 min, (P8) starting from 95% C/5% D, the fraction of D increased to 60% over 40 min. The column was washed with 95% D for 2 ruin and then ramped to 5% D. The system was re-equilibrated at 5% D for 3 min, (P9) starting from 95% C/5% D, the fraction of D increased to 40% over 23 min. The column was washed with 95% D for 2 min and then ramped to 5% D. The system was re-equilibrated at 5% D for 3 min.

DD(E) binding assay. The affinity of the probes was assessed using a DD(E) fluorescence polarization displacement assay that was described previously.[5] The displacement of a tetramethylrhodamine labeled peptide (TRITC-Tn6) from DD(E) was detected by observing the corresponding change in fluorescence anisotropy. The $K_d$ of the TRITC-Tn6 probe was determined by titrating it with the DD(E) protein and fitting the resultant fluorescence data as described previously (Caravan, *Bioconjugate Chem.* 2012, 23, 548). This experiment was performed at room temperature using a concentration of TRITC-Tn6 of 0.1 µM in the following assay buffer: Tris base (50 mM), NaCl (100 mM), $CaCl_2$) (2 mM), Triton 100 (0.01%), pH=7.8. The anisotropy measurements were made using a TECAN Infinity F200 Pro plate reader equipped with the appropriate filter set for tetramethylrhodamine (excitation 535 nm, emission 590 run).

Mn quantification in tissues and blood. Metal concentrations were determined using an Agilent 8800-QQQ ICP-MS system. All samples were diluted with 0.1% Triton X-100 in 5% nitric acid. A linear calibration curve for each metal ranging from 0.1 ppb to 200 ppb was generated daily for the quantification.

Estimates of albumin binding. Measurements were performed on a series of solutions ranging between 150-300 μM chelate-metal complex in either 4.5% Wily BSA or bovine blood plasma. 150 μL of each solution was placed within a Millipore Ultra Free MC 5 kDa cutoff filtration vessel and ~10 μL of the solution was forced through the filter by centrifugation. Mn content in each unfiltered solution and filtrate were quantified by ICP-MS. The percentage of [Mn(PyC3A)(H$_2$O)]$^-$ hound to albumin was estimated from the difference in Mn concentrations between unfiltered solution and filtrate.

Rat model of carotid artery thrombosis. All experiments were performed in accordance with the National Institutes of Health Guide for the Care and Use of Laboratory Animals (*Guide for the care and use of laboratory animals* Bethesda, Md., 1985) and were approved by the Institutional Animal Care and Use Committee at Massachusetts General Hospital, Adult male Wistar rats (N=4; weight, 200-300 g; Charles River Laboratories) were used for this study. Arterial thrombosis was induced by application of 25% w/v AlCl$_{3(aq)}$ to the vessel outer wall. Under isoflurane anesthesia, the right common carotid artery was exposed, and a small strip of filter paper soaked in the AlCl$_3$ solution was applied. Injury was performed 1-2 cm proximal to carotid bifurcation by the same investigator to minimize variability. The femoral artery was catheterized using PE-50 tubing (Fisher Scientific) for probe injection. Probes, either compound 20 or gadolinium containing control compound EP-2104R, were injected 30 min after thrombus formation. Each rat was injected with 0.01 mmol/kg probe (0.04 mmol/kg based on metal ion). For blood draw experiments, rats were catheterized in the femoral vein and artery for injection and sampling, respectively. Blood was drawn at 2, 5, 10, 15, 30, 60 and 120 min, than 24 h after injection and collected in heparinized vials. Immediately after collection a portion of the blood was centrifuged for 10 min at 5000 rpm and the plasma separated and weighed, diluted 2-fold with PBS buffer and injected onto the analytical HPLC column.

MR imaging of thrombosis in rats. Imaging was performed on a human hole-body 1.5T system (Avanto, Siemens Healthcare; Erlangen, Germany) with a custom-built transmit-receive coil. Animals were anesthetized with isoflurane (1-2%) for the duration of the experiment. Catheters were placed in the femoral vein and the femoral artery for blood draws and contrast administration, respectively. First; the head and neck were visualized with Ti-weighted images in sagittal, coronal, and axial planes, followed by a 3D TOF angiogram acquired transversely. Next molecular imaging was performed at baseline with two different sequences: 3D Ti-weighted gradient echo (GRE) and 2D Ti-weighted dark-blood fast spin echo (DB-TSE). After all pre-contrast scans were completed, 0.01 mmol/kg of the imaging probe, either EP-2104R or 18, was injected as a bolus via the femoral artery. The molecular imaging sequences used at baseline were repeated for 60 minutes following contrast delivery. The TOF angiogram was acquired with the following parameters: 3D T$_1$-weighted gradient echo sequence, TR/TE/flip angle=26 ms/5.75 ms/25°, in-plane FOV=85×85 mm, matrix=320×320, 58 slices, slice thickness=0.47 mm, voxel size=0.3×0.3×0.47 mm, 1 average, and acquisition time=4:18 minutes. The GRE sequence for molecular imaging had identical parameters to the TOF angiogram, but smaller head-to-foot coverage (48 slices) and longer TR (35 ms) resulting in a scan time of 6:34 minutes. In addition, inferior saturation was performed to null inflowing arterial blood. DB-TSE was performed with TR/TE=800 ms/20 ms, in-plane FOV=85×85 mm, matrix=320×320, 11 slices, slice thickness=2 mm, voxel size=0.3×0.3×2 mm, echo train length=11, 1 average, and acquisition time=4 minutes. GRE and DB-TSE had overlapping volumetric coverage and were acquired with axial orientation. Images were analyzed in Matlab (Version R2104a, MathWorks, Natick, Mass.) by drawing ROIs and measuring mean SI of the clot, contralateral artery, and adjacent muscle. Noise was quantified as the standard deviation (SD) of the signal measured in the air outside the animal. SNR was calculated as described above for each tissue type. We also calculated contrast-to-noise ratios for the clot and the contralateral artery relative to muscle: $CNR=(SI_{tissue}-SI_{adj\ muscle})/SD_{air}$. SNR and CNR were estimated at baseline ($SNR_{pre}$ and $CNR_{pre}$) from pre-contrast images and at various time points after contrast injection ($SNR_{post}$ and $CNR_{post}$). Normalized SNR (nSNR) values were obtained by dividing SNR at each time point by $SNR_{pre}$. Unpaired Student's t-Test was used for statistical analysis where p<0.05 was considered as significant.

Histology. Carotid arteries were harvested 90 min after generation of induction of thrombosis, carefully rinsed in phosphate buffer, embedded in OCT mounting media (Tissue-Tek) and snap-frozen in −45° C. isopentane. Arteries were cryosectioned in 20 μM slices and processed for Hemotoxylin and Eosin staining according to the standard protocol. Images were acquired using a Nikon TE-2000 microscope (40× magnification).

Example 1: Synthesis of Chelating Ligands that Form Protein Binding Mn(II) Complexes A. Synthesis of N-((5-methoxycarbonyl)-pyridin-2-yl)methyl-N,N',N'-trans-1,2-cyclohexylenediaminetriacetate (PyC3A-5-methyl ester) (4)

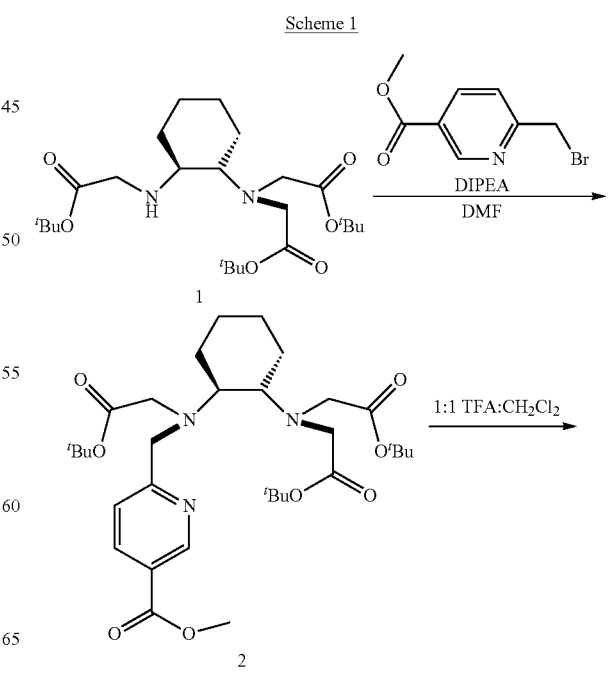

Scheme 1

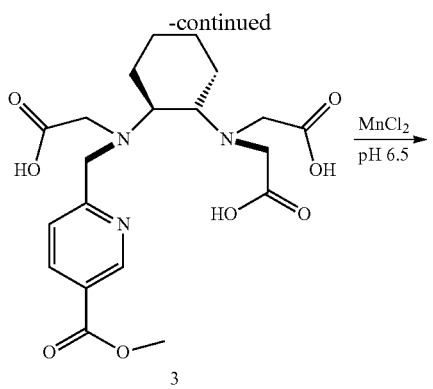

3

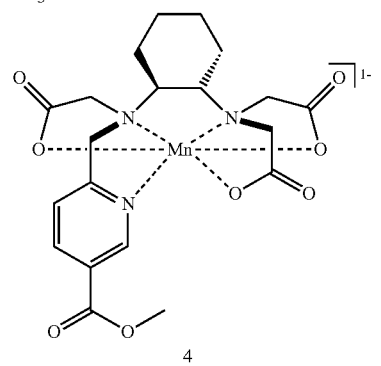

4

N-((5-methoxycarbonyl)-pyridin-2-yl)methyl-N,N',N'-trans-1,2-cyclohexylenediaminetri-tert-butylacetate (2). 6-(bromomethyl)-methylnicatinoate (0.450 g, 1.95 mmol) was added to 3 (1.00 g, 2.01 mmol), potassium iodide (0.243 g, 1.46 mmol), and diisopropylethylamine (0.468 g, 3.62 mmol) stirring in 4 mL DMF. After 3 h, the reaction was diluted to 100 mL with Et$_2$O, washed with satd. Na$_2$CO$_{3(aq)}$, copious water and brine before drying over Na$_2$SO$_4$ and concentration to a brown oil. The crude product was purified by flash chromatography (basic alumina, hexane:EtOAc, 0% to 20% EtOAc) and as 1.02 g (1.68 mmol, 84%) 6 was isolated as a clear colored oil. $^1$H NMR (500 MHZ, CDCl$_3$, δ from protio solvent): 9.07 (s, 1H), 8.24 (d, 1H), 8.03 (d, 1H), 4.20 (d, 1H), 3.04 (s, 3H), 3.86 (d, 1H), 3.53-3.30 (m, 6H), 2.73 (br t, 1H), 2.58 (br t, 1H), 2.05 (br m, 2H), 1.69 (br m, 2H), 1.65 (br m, 2H), 1.45 (s, 18H), 1.43 (s, 9H), 1.26-1.09 (m, 4H). $^{13}$C NMR (125.7 MHZ, CDCl$_3$, δ from solvent): 171.8, 171.7, 166.4, 166.3, 149.9, 137.5, 124.3, 123.7, 80.7, 80.6, 63.7, 62.0, 56.4, 54.0, 53.0, 52.4, 28.3, 26.0, 25.9. ESI-MS: m/z=606.4 [M+H]$^+$; calcd: 606.4.

N-((5-methoxycarbonyl)-pyridin-2-yl)methyl-N,N',N'-trans-1,2-cyclohexylenediaminetriacetate (PyC3A-5-methyl ester) (3). A batch of 2 (0.390 g, 0.645 mmol) was stirred in 5 mL 1:1 TFA:CH$_2$Cl$_2$ for 16 h. The reaction mixture was concentrated to en vacuo and purified by RP-HPLC using C18 column and method P1 to yield 3 (0.184 g, 0.421 mmol, 65% yield) as a white solid. $^1$H NMR (500 MHZ, D$_2$O, 70° C., δ from protio solvent): 9.83 (br s, 1H), 9.42 (br s, 1H), 8.68 (br s, 1H), 5.04-4.80 (br m, 2H), 4.61 (br s, 3H), 4.47-4.27 (br m, 6H), 3.98 (br s, 1 h), 3.74 (br s, 1 h), 2.86-2.77 (br m, 2H), 2.46 (br s, 2H), 2.09-2.01 (br m, 2H), 1.89 (br s, 2H). $^{13}$C NMR (125.7 MHZ, CDCl$_3$, 70° C.): 173.5, 170.7, 165.3 (one carboxylate C=O resonance was not resolved, likely due to coincidental overlay with another resonance), 157.0, 146.0, 145.0, 128.7, 127.1, 64.6, 62.9, 54.1, 53.0, 52.4, (one carboxylate CH$_2$ resonance was not resolved, likely due to coincidental overlay with another resonance), 24.7, 24.6, 24.5, 24.3. ESI-MS: m/z=438.2 [M+H]$^+$; calcd: 438.2.

Na[Mn(PyC3A-5-methyl ester)] (4). A batch of 3 (0.182 g, 0.416 mmol) was dissolved in 10 mL H$_2$O and the pH adjusted to 6.5 with ammonium acetate. MnCl$_2$.4H$_2$O (0.066 g, 0.130 mmol) were added and the pH re-adjusted to 6.5. The reaction mixture was purified via RPLC using the C18 column and method P2 to yield 4 (0.140 g, 0.273 mmol, 66% yield) as white solids. ESI-MS: m/z=491.1 [M+2H]$^+$; calcd: 491.1.

B. Synthesis of N—((S-hydroxymethyl)-pyridin-2-yl)methyl-N,N',N'-trans-1,2-cyclohexylenediaminetriacetate (PyC3A-5-hydroxymethyl) (7)

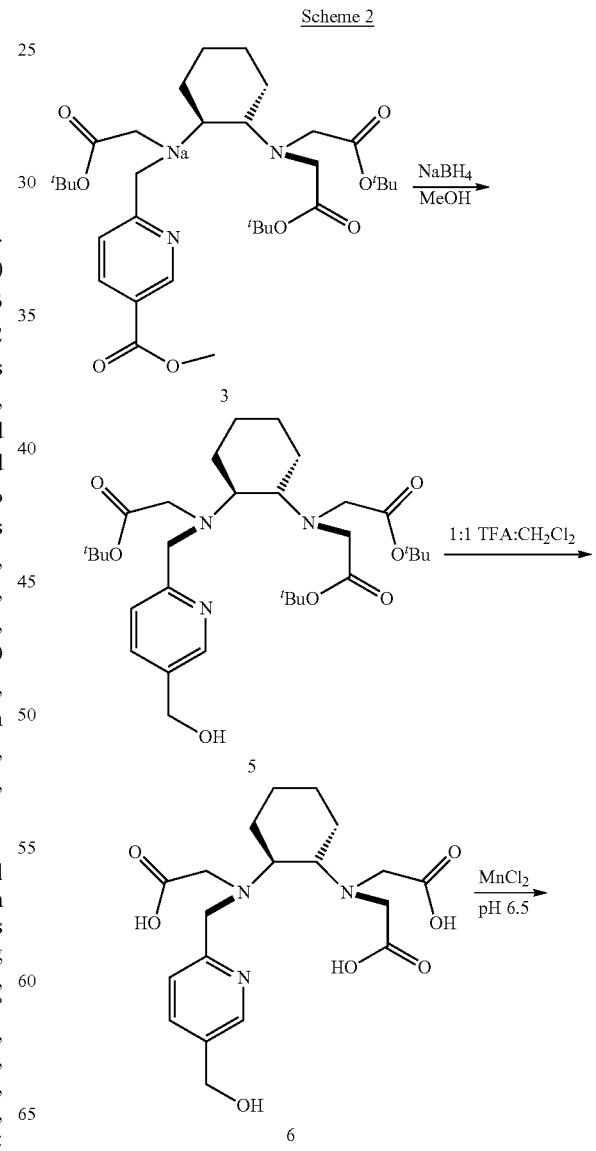

Scheme 2

C. Synthesis of N-((3-ethoxycarbonyl)-pyridin-2-yl)methyl-N,N',N'-trans-1,2-cyclohexylenediaminetriacetate (PyC3A-3-ethyl ester) (10)

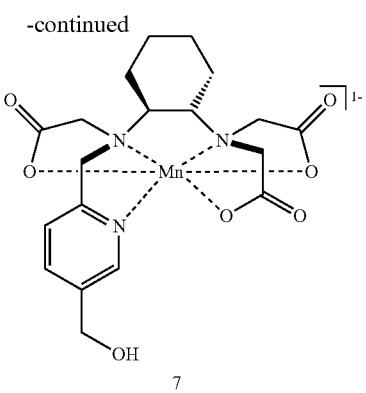

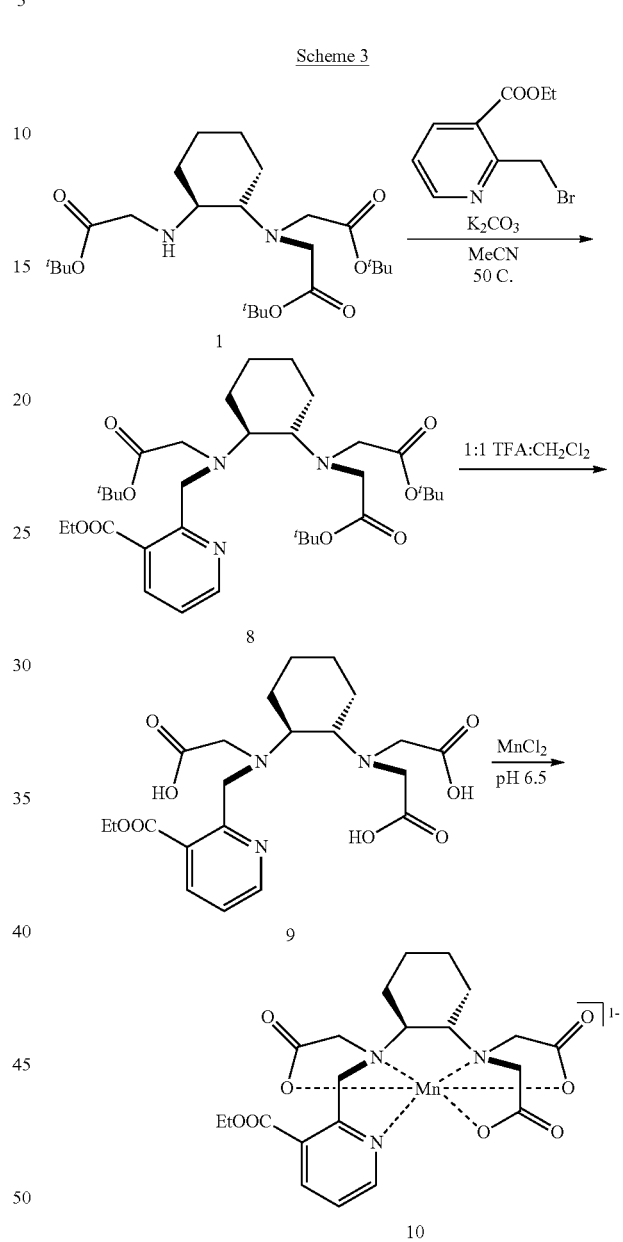

Scheme 3

N-((5-hydroxymethyl)-pyridin-2-yl)methyl-N,N',N'-trans-1,2-cyclohexylenediaminetri-tert-butylacetate (5). A batch of 2 (0.200 g, 0.331 mmol) was stirred in 20 mL MeOH at RT and NaBH$_4$ (0.562 g, 14.9 mmoL) added portionwise over the course of 24 h. The reaction was monitored by HPLC. At completion, 10 mL water was added and the reaction mixture was concentrated to dryness en vacuo. Crude 5 was carried directly through to the next step without further workup or NMR characterization. ESI-MS: m/z=578.4 [M+H]$^+$; calcd: 578.4.

N-((5-hydroxymethyl)-pyridin-2-yl)methyl-N,N',N'-trans-1,2-cyclohexylenediaminetriacetate (PyC3A-6-hydroxymethyl) (6). Crude 5 was stirred in 6 mL 1:1 TFA:CH$_2$Cl$_2$ for 16 h. The reaction mixture was concentrated en vacuo and then purified by RP-HPLC using the C18 column and method P1 to yield 6 (0.036 g, 0.082 mmol, 27% yield) as a white solid. $^1$H NMR (500 MHZ, D$_2$O, 70° C., δ from protio solvent): 9.32 (br s, 1H), 9.07 (br s, 1H), 8.65 (br s, 1H), 5.42 (br m, 2H), 4.92-4.71 (br m, 3H), 4.47-4.27 (br m, 3H), 4.16-4.07 (br m, 3H), 3.61 (br s, 1H). 2.83-2.78 (br m, 2H), 2.46 (br s, 2H), 2.04 (br s, 2H), 1.89 (br s, 2H). $^{13}$C NMR (125.7 MHZ, CDC$_3$, 70° C.): 176.8, 171.5 (one carboxylate C═O resonance was not resolved, likely due to coincidental overlay with another resonance), 153.7, 147.7, 163.0, 162.4, 129.6, 67.2, 63.8, 62.4, (one carboxylate CH$_2$ resonance was not resolved, likely due to coincidental overlay with another resonance), 55.3, 54.3, 26.5, 26.5, 26.4, 26.2. ESI-MS: m/z=410.2 [M+H]$^+$; calcd: 410.2.

Na[Mn(PyC3A-5-hydroxymethyl)] (7). A batch of 6 (0.036 g, 0.082 mmol) was dissolved in 4 mL H$_2$O and the pH adjusted to 6.5 by addition of ammonium acetate. MnCl$_2$.4H$_2$O (0.014 g, 0.070 mmol) were added and the pH re-adjusted to 6.5. The reaction mixture was purified using the C18 column and method P2 to yield 7 (0.040 g, 0.082 mmol, 100 yield) as white solids. ESI-MS: m/z=463.1 [M+2H]$^+$; calcd: 463.1.

N-((3-ethoxycarbonyl)-pyridin-2-yl)methyl-N,N',N'-trans-1,2-cyclohexylenediaminetri-tert-butylacetate (8). A batch of 0.042 g 1 (0.092 mmol) was combined with 0.152 g ethyl 2-(bromomethyl)nicotinate (0.661 mmol) and 0.120 g K$_2$CO$_3$ (8.70 mmol) in 5 mL MeCN and heated to 50° C. for 1 h. The crude reaction mixture was then concentrated to dryness and purified by flash chromatography (silica gel, 30:70 hexane:EtOAc). 8 was isolated as a crude oil with impurities and carried directly through to the next reaction without characterization.

N-((3-ethoxycarbonyl)-pyridin-2-yl)methyl-N,N',N'-trans-1,2-cyclohexylenediaminetriacetate ((PyC3A-3-methylester) (9). 0.092 g (0.148 mmol) 8 was dissolved in 2 mL TFA and stirred for 16 h. The TFA was removed en vacuo, the crude product taken up in CH$_2$Cl$_2$ and concentrated en vacuo. The product was purified by RP-HPLC using the C18 column and method P3 to yield 24 mg (0.053 mmol, 36% yield). $^1$H NMR (500 MHZ, D$_2$O, δ from protio solvent): 8.67 (d, 1H), 8.41 (d, 1H), 7.47 (t, 1H), 4.90 (br s, 1H), 4.33 (q, 2H), 4.16 (d, 1H), 3.80-3.30 (m, 6H), 3.08 (br m, 2H), 2.28 (br m, 1H), 2.11 (br m, 1H), 1.84 (br m, 1H), 1.76 (br m, 1H), 1.57 (br m, 1H), 1.35 (t, 3H), 1.35-1.21 (m, 3H)). H NMR (125.7 MHZ, d$_6$-DMSO): 174.7, 169.6, 166.4, 154.0, 152.6, 144.1, 126.4, 124.8, 66.3, 63.2, 61.9, 54.1, 50.4, 26.2, 26.2, 15.9, 25.6, 14.6. ESI-MS: m/z=452.2 [M+H]$^+$; calcd: 452.1.

Na[Mn(PyC3A-3-ethyl ester)] (10). A batch of 9 (0.024 g, 0.053 mmol) and the pH adjusted to 6.5. MnCl$_2$.4H$_2$O (0.015 g, 0.076 mmol) were combined in 1.5 mL water and the pH adjusted to 6.5. The reaction mixture was purified by RP-HPLC using C18 column and method P4 to yield 10 (0.020 g, 0.031 mmol, 58% yield) as white solids. ESI-MS: m/z=505.0 [M+2H]; calcd: 505.1.

D. Synthesis of N-((4-methoxy-3,5-dimethyl)-pyridin-2-yl)methyl-N,N',N'-trans-1,2-cyclohexylenediaminetriacetate (PyC3A-2-methoxy,3,5-dimethyl) (13)

Scheme 4

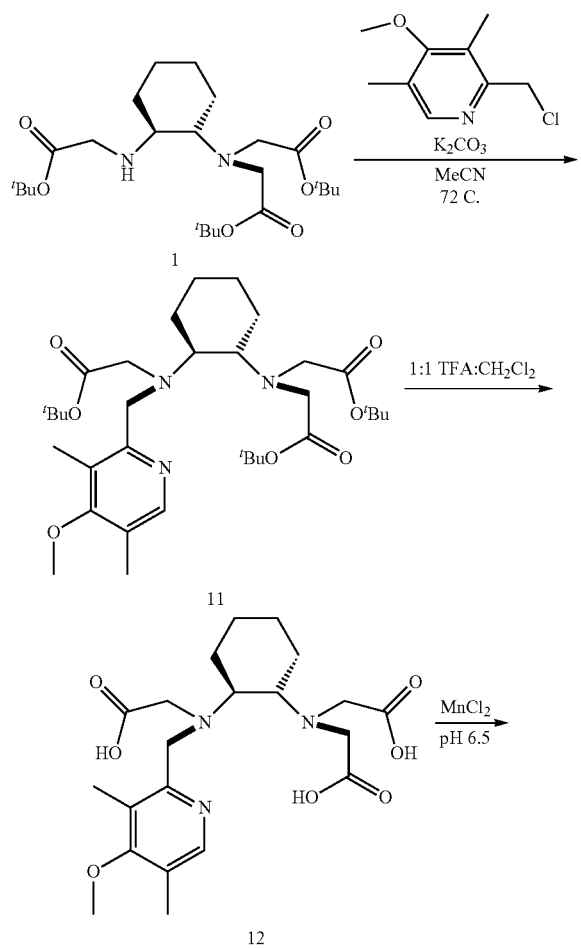

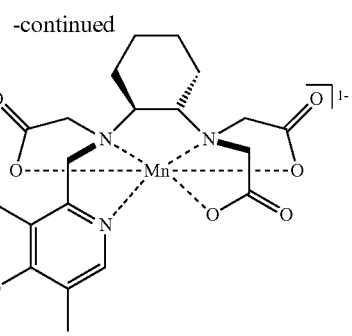

13

N-((4-methoxy-3,5-dimethyl)-pyridin-2-yl)methyl-N,N',N'-trans-1,2-cyclohexylenediaminetri-tert-butylacetate (1). A batch of 1 (0.127 g, 0.278 mmol) was combined with 2-(chloromethyl)-4-methoxy-3,5-dimethylpyridine (0.052 g, 0.280 mmol) and K$_2$CO$_3$ (0.103, 0.746 mmol) in 10 mL MeCN and heated to 72° C. for 24 h. The crude reaction mixture was then concentrated to dryness. 11 was isolated as a crude oil with impurities and carried directly through to the next reaction without characterization.

N-((4-methoxy-3,5-dimethyl)-pyridin-2-yl)methyl-N,N',N'-trans-1,2-cyclohexylenediaminetriacetate (PyC3A-2-methoxy,3,5-dimethyl) (12). Crude 11 was stirred in 1 mL TFA for 16 h, then concentrated to a yellow-colored oil and purified by RP-HPLC using the C18 column and method P3. 12 was isolated as a white solid (0.022 g, 0.050 mmol, 18% yield from 1). ESI-MS: m/z=438.2[M+H]; calcd: 438.2.

Na[Mn(PyC3A-4-methoxy-3,5-dimethyl) (13). A batch of 12 (0.022 g, 0.050 mmol) and the pH adjusted to 6.5. MnCl$_2$.4H$_2$O (0.012 g, 0.061 mmol) were combined in 1.2 mL water and the pH adjusted to 6.5. The reaction mixture was purified by RP-HPLC using the C18 column and method P4 yield 13 (0.021 g, 0.041 mmol, 82% yield) as white solids. ESI-MS: m/z=491.1 [M+2H]$^+$; calcd: 491.1.

N'-(6-methyl)nicotinoyl-N',N'',N'''trans-1,2-cyclohexylenediaminetri-$^t$Bu-acetate (14): Lithium hydroxide (0.044 g, 1.84 mmol) and 2 (1.02 g, 1.69 mmol) were combined in 16 mL of 1:1 THF:H$_2$O and stirred for 3 h at RT. The reaction was then concentrated to dryness and purified by preparative RP-HPLC using the C18 column and method P5. Fractions containing pure product were freeze dried to yield product as a white solid (0.670 g 1.13 mmol, 67%). $^1$H NMR (500 MHZ, D$_2$O, δ from protio solvent, stirred over K$_2$CO$_3$(s)): 9.09 (s, 1H), 8.15 (d, 1H), 7.07 (d, 1H), 3.95 (d, H), 3.63 (d, 1H), 3.28 (d, 1H), 3.14-3.06 (i, 5H), 2.33 (brt, 2H), 1.94 (m, 2H), 1.68 (m, 2H), 1.43 (9H), 1.38 (18H), 1.18-0.99 (m, 4H). $^{13}$C NMR (125.7 MHZ, CDC$_3$, δ from protio solvent, stirred over K$_2$CO$_3$(s))): 172.2, 171.9, 170.8, 158.2, 151.1, 1380, 131.1, 122.9, 81.8, 81.5, 62.1, 59.5, 55.9, 53.0, 52.6, 29.8, 28.1, 28.0, 25.9, 25.7, 25.4, 24.8. ESI-MS: m/z=592.3 [M+H]$^+$; calcd: 592.4.

E. Synthesis of N-((5-carboxylic acid)-pyridin-2-yl) methyl-N,N',N'-trans-1,2-cyclohexylenediaminetri-acetate (PyC3A-S-carboxylic acid) (15)

N-((5-carboxylic acid)-pyridin-2-yl)methyl-N,N',N'-trans-1,2-cyclohexylenediaminetriacetate (PyC3A-5-carboxylic acid) (15). A batch of 14 (0.140 g, 0.237 mmol) was stirred in 5 mL TFA for 16 h, then concentrated to yield 15 as a TFA adduct (0.12 g, 0.223 mmol, 94% yield) as a white solid. ESI-MS: m/z=424.2 [M+H]$^+$; calcd: 424.2.

Na[Mn(PyC3A-5-carboxylic acid) (16). To a batch of 15 (0.12 g, 0.223 mmol) adjusted to pH 6.5 was added with MnCl$_2$.4H$_2$O (0.047 g, 0.237 mmol) and the pH re-adjusted to pH 6.5. A portion of the reaction mixture was purified using method P7 to yield pure 15. ESI-MS: m/z=477.0 [M+2H]$^+$; calcd: 477.1.
Example 2: Synthesis of Fibrin-Targeted Chelate-Metal Complexes of Mn(II)
Scheme 5
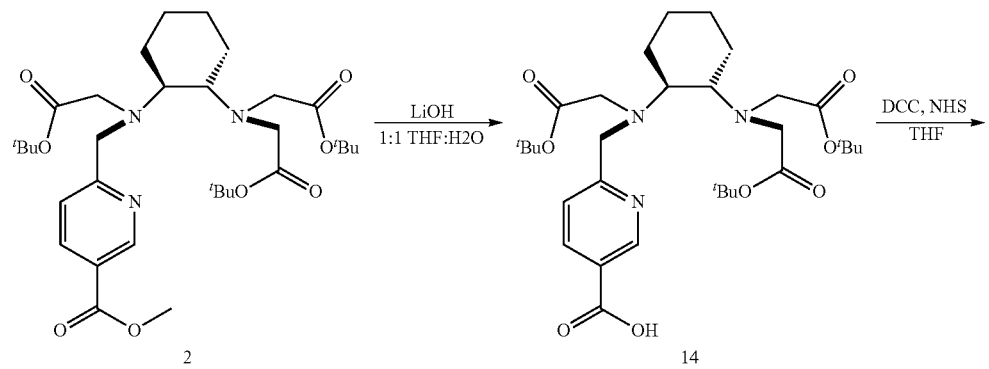
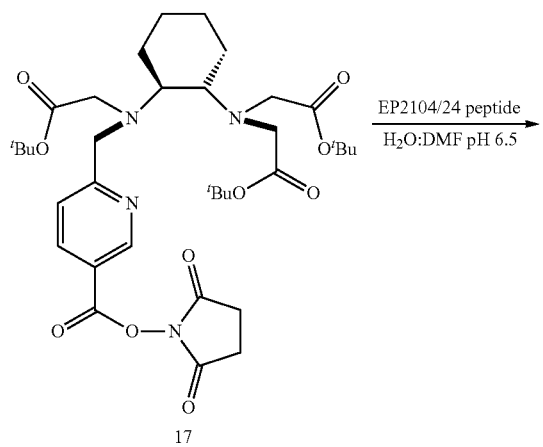
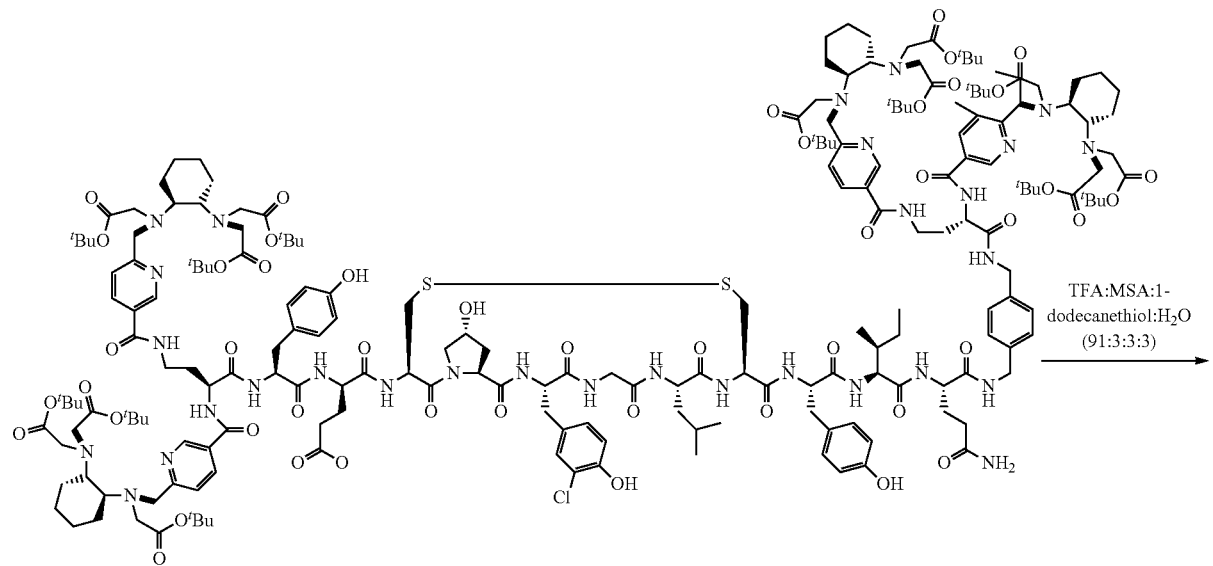

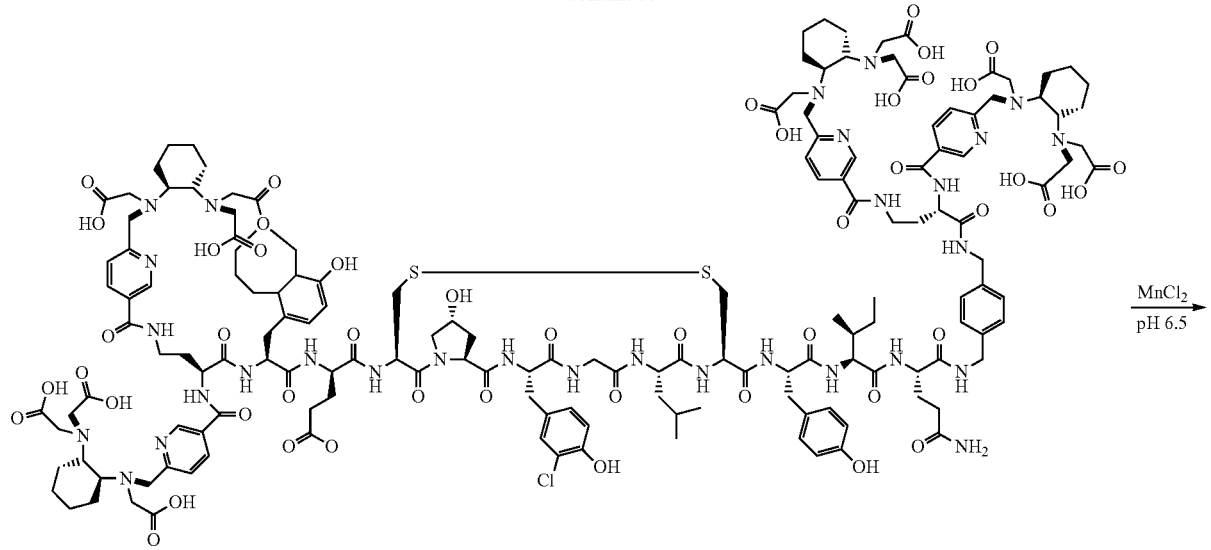

19

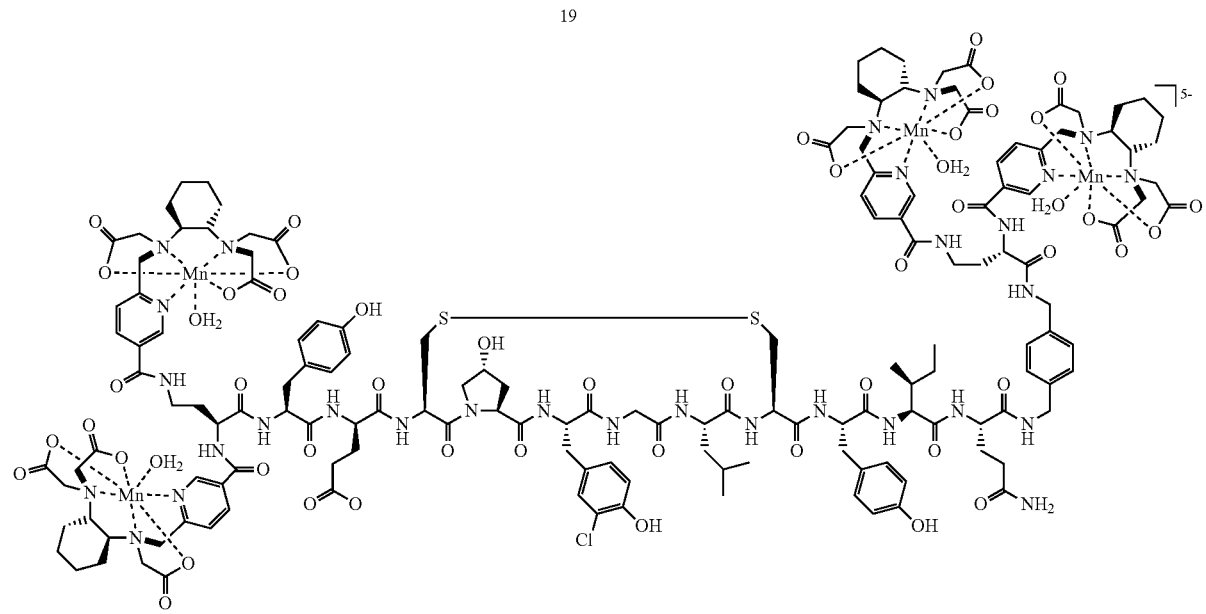

20

N-6-methyl)-N-hydroxysuccinimidylnicatinoyl-N,N',N'-trans-1,2-cyclohexylenwdiaminetri-tert-butylacetate (^tBu-PyC3A-NHS) (17): (0.471 g, 0.797 mmol) 14 was stirred with dicyclohexylcarbodiimide (0.167 g, 0.800 mmol) and N-hydroxysuccinimide (0.109, 0.94, mmol) in 10 mL THF. A white precipitate formed within seconds. LC-MS confirmed full conversion after 16 h stirring. The precipitate was removed by filtration and the clear mother liquor concentration to a pale, colorless oil. The product can be carried directly through to the next step, or purified by RP-HPLC using the C18 column and method P5. $^1$H NMR (500 MHZ, $D_2O$, δ from protio solvent): 9.15 (s, 1H), 8.32 (d, 1H), 8.21 (d, 1H), 4.33 (d, 1H), 4.15 (d, 1H), 3.55-3.25 (m, 6H), 2.91 (s, 4H), 2.73 (t, 1H), 2.50 (t, 1H), 1.91 (m, 2H), 1.81 (m, 2H), 1.45 (18H), 1.38 (9H), 1.18-1.02 (m 4H). $^{13}$C NMR (125.7 MHZ, $CDCl_3$, δ from protio solvent): 171.5, 169.3, 169.2, 161.3, 150.3, 138.2, 124.29, 119.7, 108.0, 98.5, 80.7, 80.6 (two coincidental peaks), 68.6, 63.9, 62.2, 54.0, 52.8, 49.3, 34.0, 28.2 (two coincidental peaks), 29.3, 25.9, 25.9 (two coincidental peaks), 25.8, 25.7. ESI-MS: m/z=689.3 [M+H]$^+$; calcd: 689.4.

$^t$Bu-protected FBP-CyP3A$_4$ (18): The oil was taken up in 2 mL DMF and added to L-2,4-diamino-N-butyramide-[Tyr-dGlu-Cys-Hyp-Typ(3-Cl)-Leu-Cys-Ile-Gln (3→8) disulfide]-1-(4-[(L-2,4-diamino-butyrylamino)-methyl]-benzyl-amide (EP2104/24: 0.211 g, 0.123 mmol)) and 4-dimethylaminopyridine (0.016 g, 0.131 mmol) stirring in 2 mL DMF. The reaction was adjusted to pH 6.5 with DIPEA and stirred at RT. After 16 h stirring, 250 mL satd. NaCl solution was added to the reaction mixture dropwise to precipitate white solids. $^t$Bu-protected FBP-CyP3A$_4$ was purified by RP-HPLC using the C5 column and method P6. Fractions containing product were freeze dried to yield product as a white solid (0.177 g, 0.0441 mmol, 35%). ESI-MS: m/z=1004.0 [M+4H]$^{4+}$; calcd. 1004.0. m/3z=1338.4 [M+3H]$^{3+}$; calcd. 1338.4. m/2z=2007.6 [M+2H]$^{2+}$; calcd. 2007.6.

FBP-CyP3A$_4$ (19): Compound 18 (0.177 g, 44.1 μmol) was stirred in 5 mL of a 91:3:3:3 mixture of TFA:methane sulfonic acid:n-dodecanethiol:water for 90 min before dilution with 50 mL Et$_2$O. The flocculent white solids were centrifuged to a solid pellet and the supernatant decanted. After several washes with Et$_2$O the solids were dried to yield pure product as a white powder (0.147 g, 44.0 μmol, 100%). ESI-MS: m/3z=1113.6 [M+3H]$^{3+}$; calcd. 1113.8. ESI-MS: m/z=1670.1 [M+2H]$^{3+}$; calcd. 1670.2.

Mn-FBP (20): The pH of a 10 mL solution of 19 (0.018 g, 5.4 μmol) adjusted to pH 6.5 was added MnCl$_2$.4H$_2$O (0.0053 g, 27.0 μmol). The solution was re-adjusted to pH 6.5 and purified by RP-HPLC using the C5 column and method P7. Fractions containing product were freeze dried to yield pure product as a while powder (0.0080 g, 2.2 μmol, 41%). ESI-MS: m/3z=1184.6 [M+8H]$^{3+}$; calcd. 1184.4. m/2z=1776.4 [M+6H]$^{2+}$; calcd. 1776.5.

Example 3: Synthesis of Collagen-Targeted Chelate-Metal Complexes of Mn(II)

$^t$Bu-Protected CBP-PyC3A$_4$ (21). To a batch of EP-3533 peptide (see Caravan, P., Biplab, D., Dumas, S., Epstein, F. H., Helm, P. A., Jacques, V., Koerner, S., Kolodziej, A., Shen, L., Sun, W.-C., Zhang, Z. Angew. Chem. Int. Ed 2007, 46, 8171) (0.154 g, 0.067 mmol) stirring in 3 mL DMF/1 mL H$_2$O adjusted to pH 9 with DIPEA (wet pH paper), was added 17 (0.280 g, 0.407 mmol) portionwise. After 16 h stirring, the solution was diluted with 100 mL water and freeze dried to a crude white residue. Compound 21 was carried through to the next step without further purification. ESI-MS: m/3=1337.0 [M+3H]$^{3+}$; calcd. 1337.0 CBP-PyC3A$_4$ (22). Compound 21 was stirred in 4 mL 91:3:3:3 TFA:methanesulfonic acid:1-dodecanethiol:H$_2$O for 2 h. The reaction mixture was then added to 100 mL cold Et$_2$O to precipitate the product. The solids were collected in the bottom of a 50 mL conical tubes by centrifugation and separated by decantation. Compound 22 was carried through to the next step without further purification. ESI-MS: m/3z=1168.0 [M+3H]$^{3+}$; calcd. 1167.8

Mn-CBP (23). A batch of MnCl2.4H$_2$O (0.047 g, 0.237 mmol) was added to crude 22 to form 23 which was then purified by HPLC. ESI-MS: m/6z=1221.0 [M+6H]$^{3+}$; calcd. 1221.1.

Example 4: Synthesis of Oxidized Collagen-Targeted Chelate-Metal Complexes of Mn(II)

N-((5-hydrazide)-pyridin-2-yl)methyl-N,N',N'-trans-1,2-cyclohexylenediaminetriacetate (PyC3A-5-hydrazide) (24). A batch of 17 (0.180 g, 0.262 mmol) and tert-butylcarbazate (0.070 g, 0.606 mmol) were stirred in 5 mL MeOH/2 mL THF. The pH of the reaction mixture was adjusted to ~9 (wet pH paper). After 2 h stirring, the reaction mixture was concentrated to dryness and taken up in 5 mL of 6M HCl. After 2 h stirring, the reaction mixture was concentrated to white solids and taken up in H$_2$O. Any solids were removed by filtration. Small aliquots of this reaction mixture were removed and purified by method P7 to yield 24 as white powder. ESI-MS: m/z=438.2 [M+H]$^+$; calcd: 438.2.

Na[Mn(PyC3A-5-hydrazide)] (25). Compound 25 was prepared in situ. To a solution of 24 in pH 7.4 Tris buffer (50 mM) was titrated MnCl$_2$.4H$_2$O. Chelation of Mn was monitored by HPLC. ESI-MS: m/z=491.2 [M+2H]$^+$; calcd: 491.1.

Example 5: Synthesis of a Peroxidase Reactive Complex

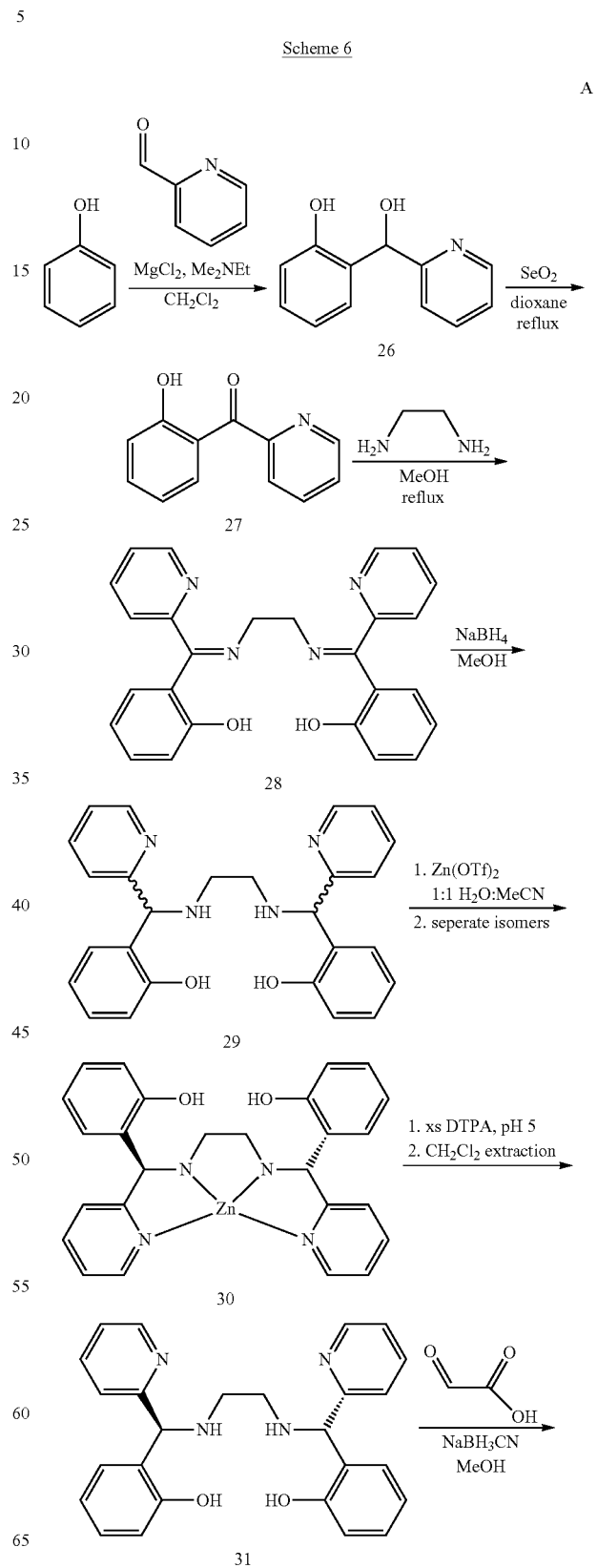

Scheme 6

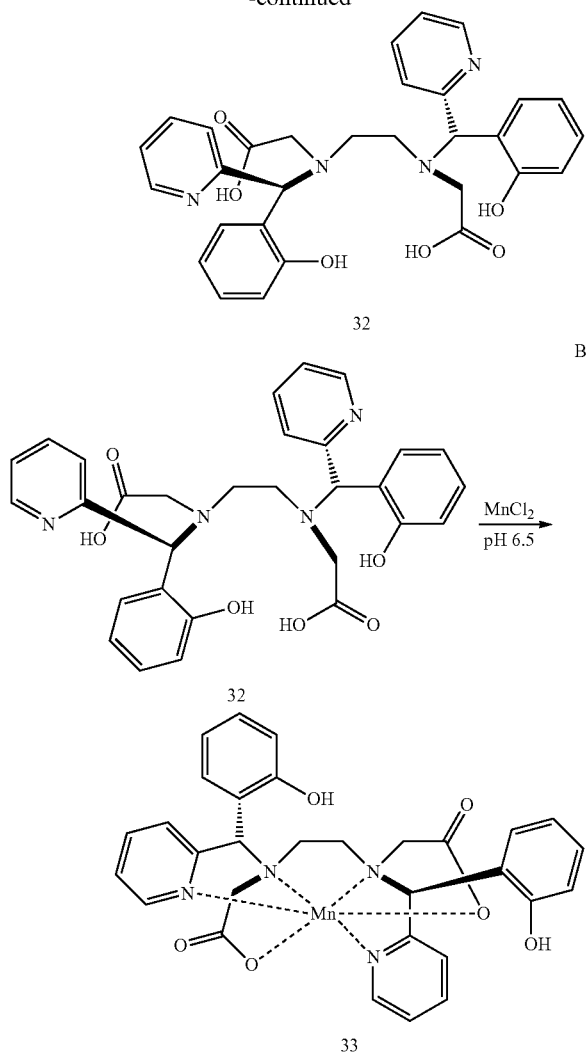

2-((hydroxy(pyridin-2-yl)methyl)phenol (26). A batch of 10.4 g(111 mmol) phenol in 50 mL CH$_2$Cl$_2$ was stirred with 18.48 g (193 mmol) magnesium chloride and 8.428 g (115 mmol) N,N-dimethylethylamine for 30 min. To this mixture, 5.85 g(55.0 mmol) 2-pyridinecarboxaldehyde in 25 mL CH$_2$Cl$_2$ was added dropwise over the course of 3 h. After completion of the addition, the resultant heterogenous, bright orange mixture was stirred at RT for 72 h. 100 mL H$_2$O was added to the reaction, and the mixture was titrated with conc. HCl to pH 1, than the pH adjusted to 9 via addition of conc. Na$_2$CO$_3$. The organic layer was separated, and the aqueous portion washed again with 100 mL CH$_2$Cl$_2$. The organic portions were pooled, dried over Na$_2$SO$_4$ and concentrated to an orange-colored syrup. The product was purified by flash chromatography (silica gel, hexane:EtOAc, 0-60% EtOAc) to yield 7.08 g (35.2 mmol, 64% yield) 26 as a white solid. $^1$H NMR (500 MHZ, CDCl$_3$, δ from TMS): 8.47 (d, 1H), 7.72 (t, 1H), 7.45 (d, 1H), 7.21 (d, 1H), 7.21 (m, 2H), 6.95 (d, 1H), 6.89 (t, 1H), 6.96 (s, 1H). $^{13}$C NMR (125.7 MHZ, CD$_3$Cl, δ from TMS): 161.7, 155.3, 147.6, 138.2, 129.5, 128.3, 127.0, 123.0, 120.4, 120.2, 118.5, 74.4. ESI-MS: m/z=202.0 [M+H]$^+$; calcd.: 202.0.

2-picoloylphenol (27). To a batch of 1.41 g (7.01 mmol) 2-(hydroxy(pyridin-2-yl)methyl)phenol in 40 mL dioxane was added 0.418 g (3.77 mmol) selenium(IV) dioxide. The mixture was heated to reflux and stirred for 90 min. The reaction was then cooled and black insoluble were removed filtration through celite and the mother liquor concentrated to a yellow-green oil. The oil was purified by flash chromatography (silica gel, hexane:EtOAc, 0-70% EtOAc) and 1.190 g (0.597 mmol, 85.2%) were isolated as a bright yellow oil.

2,2'-((1Z,1'Z)-(ethane-1,2-diylbis(azanylylidene))bis (pyridin-2-ylmethanylylidene))diphenol (28). To a batch of 0.168 g (2.80 mmol) ethylene diamine in 40 mL MeOH was added 1.190 g (5.98 mmol) 27. The reaction was heated to reflux and stirred 30 min, then cooled to RT and stirred for 16 h. The resultant yellow solids were isolated via filtration and dried en vacuo, yielding 0.942 g (2.22 mmol, 79.6% yield) 28 isolated as a yellow solid. $^1$H NMR (500 MHZ, CDCl$_3$, δ from TMS): 12.36 (s, 1H), 8.75 (d, 1H), 8.13 (d, 1H), 7.95 (m, 2H), 7.53 (m, 2H), 7.07 (d, 1H), 6.92 (t, 1H). $^{13}$C NMR (125.7 MHZ, CD$_3$Cl, δ from TMS): 197.3, 163.6, 155.5, 148.4, 137.6, 136.8, 134.5, 126.3, 124.7, 119.3, 119.0, 118.6. ESI-MS: m/z=200.0 [M+H]$^+$; calcd.: 200.1.

(+/−) (R,R/S,S) 2,2'-((ethane-1,2-diylbis(azanediyl))bis (pyridin-2-ylmethylene))diphenol (31). To a batch of 2.90 g (6.87 mmol) 28 stirring in 50 mL MeOH was added 0.758 g (20.0 mmol) sodium borohydride. Effervescence was observed as the color of the solution bleached from yellow to a clear beige. After 1 h, the reaction was quenched with 10 mL water and MeOH was removed en vacuo. The reaction was then partitioned between 50 mL each satd. NaHCO$_3$ $_{(aq)}$ and CH$_2$Cl$_2$. The layers were separated and the aqueous portion washed with another 100 mL CH$_2$C2. The organic portions were pooled, dried over Na$_2$SO$_4$ and concentrated to 2.92 g of 29 of yellow oil (6.85 mmol, 100% conversion to racemic diamine). The oil was taken up in 30 mL MeOH/10 mL H$_2$O and 2.490 g Zn(OTf)$_2$ (6.85 mmol) were added. The solution was adjusted to pH 6.5 by addition of solid ammonium acetate and stirred for 16 h before concentration to dryness.

The Zn chelated R,R/S,S and R,S/S,R isomers (30) were separated by RP-HPLC using the C18 column and method P7. A batch of 0.075 mmol (0.154 mmol)R,R/S,S isomer was dissolved 200 mM diethelynetriaminepentaacetic acid and the pH adjusted to 5.0. After 2 h stirring, the pH was adjusted to >8.0 and 31 was extracted with CH$_2$Cl$_2$, dried over Na$_2$SO$_4$ and dried en vacuo pure product isolated at 0.066 g (0.154 mmol). $^1$H NMR (500 MHZ, CDCl$_3$, δ from TMS): 8.57 (d, 2H), 7.60 (t, 2H), 7.21 (m, 4H), 7.03 (m, 4H), 6.84 (m, 4H), 4.94 (s, 2H), 2.94 (s, 4H).

Janus HBED/BPED "JED" (32). To a batch of 0.082 g (0.192 mmol) 31 in 20 mL MeOH was added 1.03 g (12.3 mmol) NaHCO$_3$ and 0.889 g (9.66 mmol) glyoxylic acid monohydrate). A batch of 0.119 g (1.89 mmol) sodium cyanoborohydride was added portionwise over the course of 8 h. After stirring for 16 h at RT, the reaction mixture was concentrated to dryness and purified by RP-HPLC using the C18 column and preparative method P8. Pure 32 was isolated as 0.104 g (0.192 mmol, 100% yield) of a white solid. ESI-MS: m/z=543.0 [M+H]$^+$; calcd.: 543.2.

Mn(II)-JED (33): To a batch of 0.104 g (0.192 mmol) 32 stirring in 4 mL each H$_2$O:MeCN was added 0.037 g (0.187 mmol) MnCl$_2$.H$_2$O and the solution adjusted to pH 6.5 by addition of solid ammonium acetate. The reaction mixture was purified by RP-HPLC using the C18 column and method P7. Pure 33 was isolated as 0.041 g (0.069 mmol, 35.9% yield) white solids. ESI-MS: m/z=596.0 [M+H]$^+$; calcd.: 596.2.

Example 6: Synthesis of a Thiol Reactive Complex

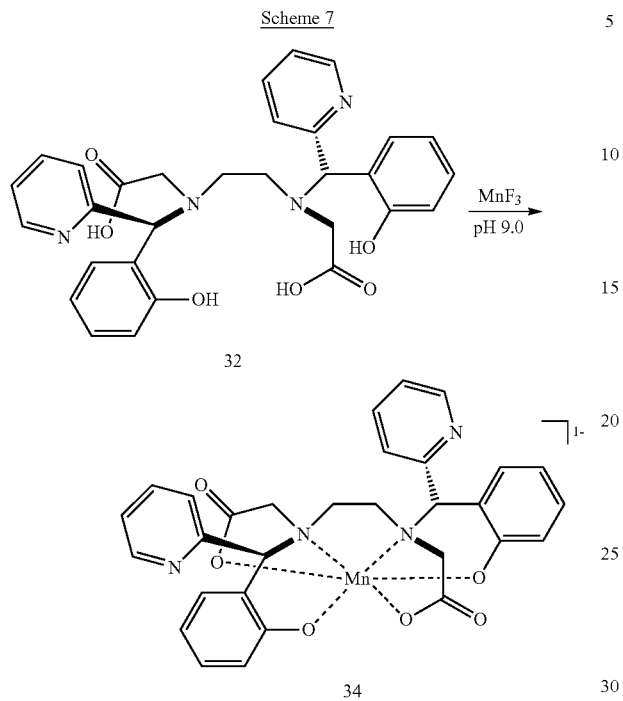

Mn(III)-JED (34): To a batch of 0.053 g (0.098 mmol) 32 stirring in 10 mL H$_2$O at pH 9.1 was added 0.009 g (0.080 mmol) of MnF$_3$ and the solution adjusted to pH 6.5. The reaction mixture was purified by RP-HPLC using the C18 column and method P9. Pure 34 was isolated as 0.018 mmol (0.029, 36.3% yield) brown solids. ESI-MS: m/z=595.0 [M+2H]$^+$; calcd.: 595.1.

Example 7: Relaxivity of Mn(II) Complexes that Target Proteins at 1.41 T, 37° C.

Incorporation of lipophilic functionality into the chelate-metal complexes promotes binding to plasma proteins such as serum albumin. This binding provides a change in relaxivity measured in human blood plasma compared to that measured in PBS. In most cases, a large (40-170%) increase in relaxivity ($r_1$ or $r_2$) is observed (Table 1).

| Chelate-metal complex | $r_1$ in PBS (mM$^{-1}$s$^{-1}$) | $r_2$ in PBS (mM$^{-1}$s$^{-1}$) | $r_1$ in human blood plasma (mM$^{-1}$s$^{-1}$) | $r_2$ in human blood plasma (mM$^{-1}$s$^{-1}$) |
|---|---|---|---|---|
| 4 | 3.1 | 6.9 | 2.1 | 7.8 |
| 7 | 2.1 | 3.5 | 5.7 | 12.4 |
| 10 | 2.7 | 5.6 | 5.8 | 16.8 |
| 13 | 2.5 | 4.8 | 3.5 | 8.9 |
| 25 | 3.4 | 8.7 | 5.2 | 14.6 |

Table 1 shows the relaxivity of four protein binding Mn(II)-based chelate-metal complexes.

Example 8. 18 has High Affinity for the Soluble Fibrin Degradation Product DD(E)

The affinity of the probes was assessed using the DD(E) fluorescence polarization displacement assay (see methods, above). The displacement of a tetramethylrhodamine labeled derivative of the fibrin binding peptide (termed TRITC-Tn6) from DD(E) as a function of 18 or EP-2104R concentration was detected by observing the corresponding change in fluorescence anisotropy (FIG. 1). The $K_d$ of the TRITC-Tn6 probe was determined by titrating it with the DD(E) protein and fitting the resultant fluorescence data as described by Kolodziej (Bioconjugate Chem. 53:548-556). 18 binds DD(E) with $K_d$=110 nM; we recorded $K_d$=240 nM for EP-2104R in the same DD(E) preparation.

Example 9. The Mn of 20 has a Rapidly Exchanging Inner Sphere Water Co-Ligand

Figure 2:
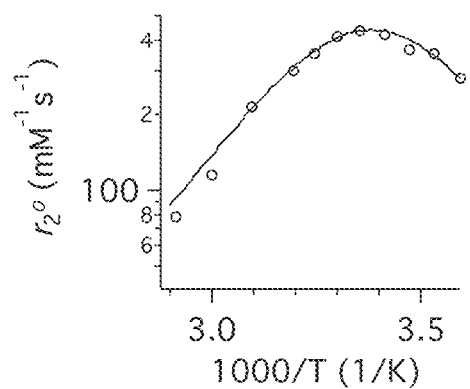
FIG. 2 shows that the Mn ions in compound 20 have one rapidly exchanging water ligand. $H_2^{17}O$ transverse relaxivity in the presence of compound 20 (open circles) as a function of temperature is shown. Solid lines are fits to the data.

The presence of a rapidly exchanging water co-ligand (rate of exchange=$10^8$ s$^{-1}$) was established by monitoring the temperature dependence of H$_2$$^{17}$O transverse relaxivity of 20 (FIG. 2) (see methods, above).

Example 10. 20 Exhibits High-Relaxivity in the Presence of Fibrin

Relaxivity values of 20 were recorded in pH 7.4 Tris buffer, bovine blood plasma, 4.5% wt/v BSA, human fibrinogen and human fibrin gel at 1.4 T, 37° C. (Table 2). 18 exhibits greater relaxivity in the presence of fibrin gel compared to human fibrinogen or to abundant plasma proteins

| conditions | $r_1$ (mM$^{-1}$s$^{-1}$) |
|---|---|
| PBS | 8.7 |
| Blood Plasma | 10.7 |
| Bovine Serum Albumin | 11.4 |
| Fibrinogen | 9.5 |
| Fibrin | 13.5 |

Table 2 shows the Ti-relaxivity of 20 measured in pH 7.4 Tris buffer, bovine blood plasma, 4.5% wt/v BSA, human fibrinogen and human fibrin gel at 1.4 T, 37° C.

Example 11. 20 Detects Carotid Artery Thrombosis

Figure 3:
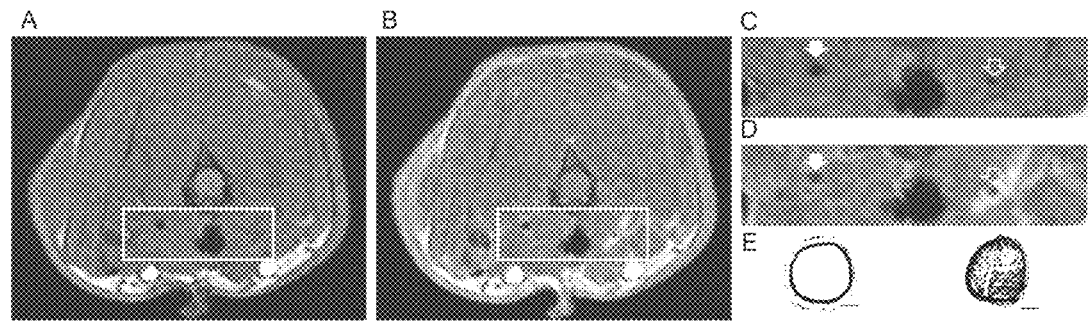
FIG. 3 shows MR imaging of carotid artery thrombosis in a rat model with compound 20. Axial $T_1$-weighted images before (A, C) and 35 minutes after intravenous administration of compound 20 (B, D) at 1.5T. (C) and (D) are expanded regions from (A) and (B), respectively showing the common carotid arteries. Compound 20 generates marked signal enhancement in the ipsilateral vessel (open arrow, D) after compound 20 injection, but not in contralateral vessel (filled arrow, D) or in the vessel prior to Mn-FBP injection (C). (E) Hematoxylin and Eosin stained sections of contralateral (left) and ipsilateral (right) carotid arteries showing occlusive thrombus in the injured vessel; scale bar=300 µm.
Figure 4:
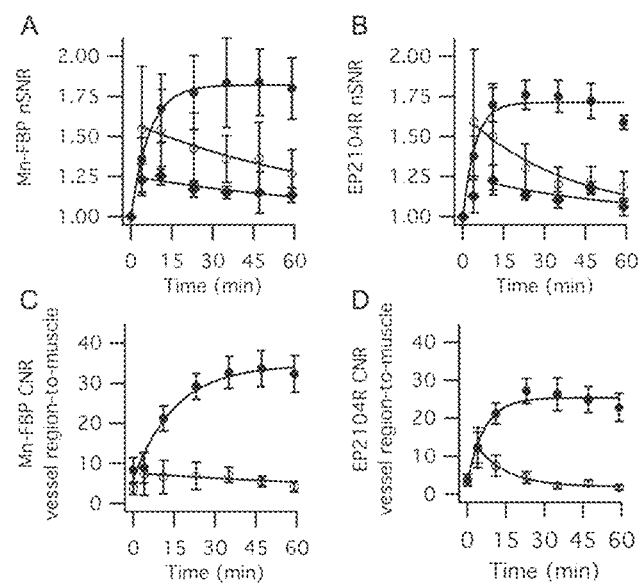
FIG. 4 shows the quantitation of the MR imaging data with compound 20. (A) and (B) show normalized signal-to-noise ratio (nSNR) of the thrombus (closed circles), contralateral vessel region (open circles), and muscle (closed diamonds) following administration of compound 20 and EP-2104R, respectively, showing persistently, enhanced thrombus with each probe and washout of signal from background tissue. (C) and (D) contrast-to-noise ratio (CNR) of thrombus-to-muscle (closed circles) and contralateral vessel region-to-muscle (open circles) following administration of compound 20 and EP21.04R respectively, showing large and persistently high CNR for the thrombus with each probe. N=4 for each probe, error bars represent standard error of the mean.

Compound 20 provides visualization of the arterial thrombus with high conspicuity and the imaging is supported by ex vivo histology (FIG. 3). Surprisingly, 20 provides equivalent thrombus nSNR and thrombus-to-muscle contrast to noise ratio (CNR) to the Gd based fibrin imaging probe EP-2104R that is known to have even higher relaxivity (J. Am. Chem. Soc. 2008, 130:6025) (FIG. 4). This data further highlights the efficacy of Mn to generate MR contrast.

Example 12. Intravenously Injected Mn-FBP is Wholly Cleared by 24 h

Figure 5:
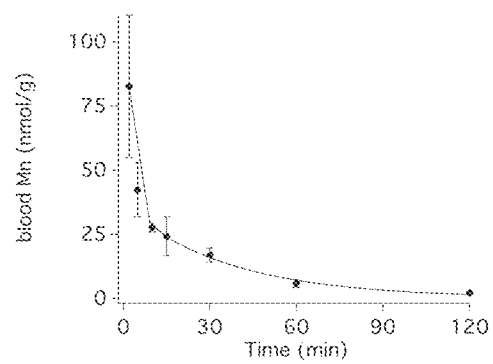
FIG. 5 shows blood clearance of compound 20 as a function of time (N=4)

Compound 20 clears form the blood with a half-life of 22.6±6.8 m (FIG. 5). The only significant increase in Mn over baseline levels were found in the kidney and muscle where 0.37±0.14 and 0.02±0.02 percent of the injected dose per gram remain, respectively (Table 3).

| Tissue | Endogenous Mn | | 24 h p.i | | |
|---|---|---|---|---|---|
| | nmol Mn/g | Std. dev. | nmol Mn/g | Std dev | P * < 0.05 |
| Lung | 4.48 | 2.62 | 4.90 | 0.51 | 0.76 |
| Kidney | 17.84 | 5.39 | 47.39 | 14.93 | 0.01* |

-continued

|  | Endogenous Mn | | 24 h p.i | | |
|---|---|---|---|---|---|
| Tissue | nmol Mn/g | Std. dev. | nmol Mn/g | Std dev | P * < 0.05 |
| Brain | 7.27 | 0.52 | 13.78 | 6.85 | 0.11 |
| Liver | 50.75 | 2.97 | 54.88 | 7.84 | 0.36 |
| Heart | 7.72 | 1.01 | 8.84 | 0.80 | 0.13 |
| Spleen | 6.21 | 3.53 | 12.90 | 5.76 | 0.09 |
| Muscle | 1.77 | 0.42 | 4.30 | 1.58 | 0.02* |
| Bone | 7.97 | 0.57 | 7.32 | 2.21 | 0.59 |
| Blood | 1.03 | 0.83 | 0.34 | 0.10 | 0.15 |

Table 3 shows endogenous Mn levels in male Wistar rats (N=4) and Mn levels 24 h after intravenous injection of 0.01 mmol/kg compound 20 (N=4). Statistically significant differences (*, P<0.05) were observed in kidney and muscle and represent 0.37±0.14 and 0.02±0.02 percent of the injected dose per gram tissue, respectively.

Example 13. The Relaxivity Difference Between Compounds 33 and 34 is Very Large and Field Independent The relaxivity of the compounds 33 and 34 were measured in water and human blood plasma (Table 4). The relaxivity changes observed between toggling between 33 and 34 oxidation states are 660%, 900%, 500%, and 400% for conditions A-D, respectively.

|  | r1 (mM$^{-1}$s$^{-1}$) | | | |
|---|---|---|---|---|
| Compound | Water | | Human blood plasma | |
|  | 1.41 T | 11.7 T | 1.41 T | 11.7 T |
| 33 | 0.5 | 0.5 | 0.9 | 0.5 |
| 34 | 3.3 | 2.5 | 8.1 | 1.9 |

Table 4 shows that the Mn(II)-based 26 demonstrates much higher relaxivity than its Mn(III)-based sister complex 27 and that this relaxivity difference is largely independent of applied magnetic field.

Figure 6:
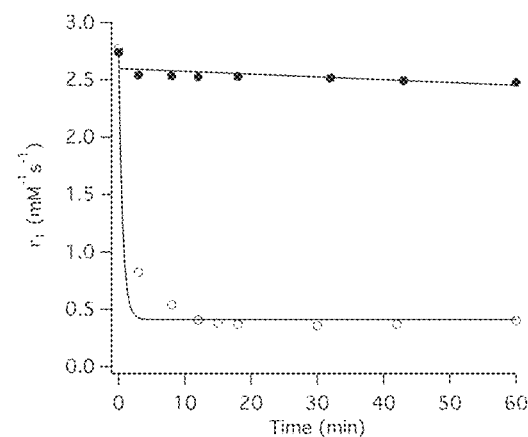
FIG. 6 shows relaxivity change as a function of time for the peroxidase reactive compound 20 in the presence of hydrogen peroxide without (closed circles) or with (open circles) horseradish peroxidase. A 7-fold in relaxivity is observed within 3 min of peroxidase exposure.

Example 14. Compound 33 is Rapidly Converted to Compound 34 by Peroxidase Enzymes with 7-Fold Relaxivity Change The relaxivity of compound 33 in PBS (1.41 T, 37° C.) was measured in the presence of a steady state concentration of hydrogen peroxide generated by 10 U/mL glucose oxidase+8 mM glucose (FIG. 6). Measurements were performed in the absence or presence of horseradish peroxidase. The filled and open circles depict relaxivity in the absence and presence of the peroxidase enzyme, respectively. Solid lines represent fits to the data.

Figure 7:
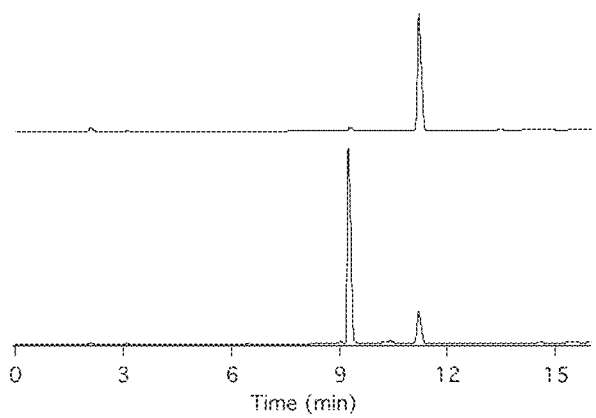
FIG. 7 shows that the conversion of compound 33 to compound 34 occurs cleanly and without byproducts. The top trace is compound 33 and the bottom trace is compound 33 (largely converted to compound 34) after treatment with hydrogen peroxide and horseradish peroxide.

FIG. 7 shows HPLC traces taken after the 1 h incubation period. The top trace HPLC trace corresponds to that of 33, the bottom trace corresponds to that of after 1 h incubation with hydrogen peroxide and peroxidase. 34 is the only product formed.

Figure 8:
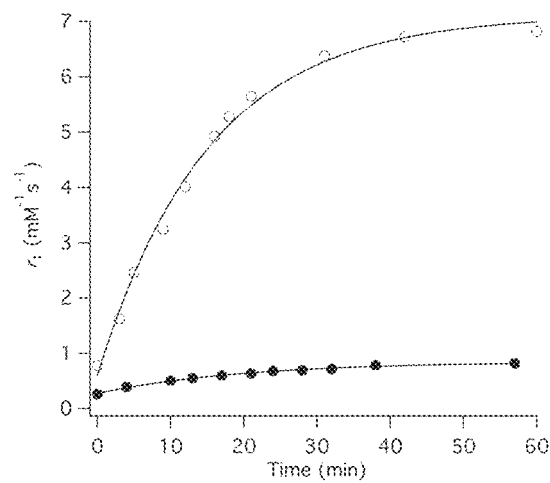
FIG. 8 shows relaxivity change (1.41 T, 37° C.) as a function of time for the thiol reactive compound 33 while incubating in human blood plasma without (closed circles) or with 5 mol. equiv. L-cysteine (open circles).

Example 15. In Human Blood Plasma, Compound 34 can be Converted to Compound 33 by Addition of L-Cysteine The $r_1$ as a function of time (1.4 T, 37° C.) of 34 in human blood plasma without and with 5 mol. equivalent L-cysteine is depicted by the filled and open circles, respectively (FIG. 8). Solid lines represent fits to the data. Addition of L-cysteine triggers rapid conversion of compound 34 to compound 33, this causes a large increase in $r_1$.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula (A):

$$(D^1)_a\text{-}(L^1)_b\text{-}TBM\text{-}(L^2)_c\text{-}(D^2)_d \quad (A)$$

or a pharmaceutically acceptable salt thereof,
wherein:
TBM is a target binding moiety:
$L^1$ is a linker:
$L^2$ is a linker:
a is an integer from 0 to 4:
b is 0 or 1:
wherein if a is 0, b is 0:
c is 0 or 1:
d is an integer from 0 to 4:
wherein if d is 0, c is 0:
wherein at least one of a and d is an integer from 1 to 4; and
each $D^1$ and $D^2$ are independently selected from a compound of Formula (I):

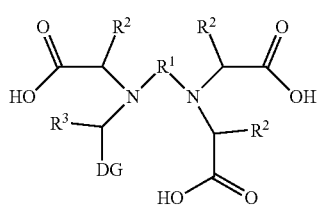

(I)

or a pharmaceutically acceptable salt thereof,
wherein:
$R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl)$(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;

each $R^2$ and $R^3$ is independently selected from the group consisting of H, $CO_2H$, $(C_1-C_6$ alkyl)$CO_2H$, $C_1-C_6$ alkyl, $C_2-C_6$ alkenyl, $C_2-C_6$ alkynyl, $C_4-C_6$ cycloalkyl, $C_6-C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, and $PO_3R^4R^5$;

each $R^4$ and $R^5$ is independently selected from the group consisting of H and $C_1-C_6$ alkyl, wherein the alkyl is optionally substituted by 1, 2, 3, or 4 independently selected $R^X$ groups;

DG is selected from the group consisting of:

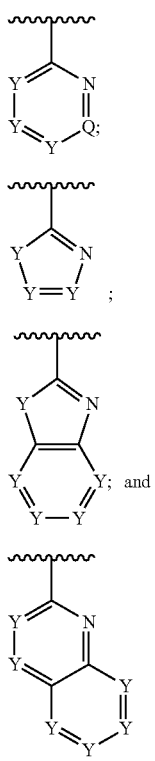

or any constitutional isomers of Formulas IV and V, wherein each Y is independently CH, CZ, N, O, S or $NR^4$;

Q is CH, CZ, N, O, S or $NR^4$;

each Z is independently selected from the group consisting of H, OH, $OR^4$, $CO_2R^4$, —$(C_{1-6}$ alkyl)$CO_2H$, $C_1-C_6$ alkyl, $C_2-C_6$ alkenyl, $C_2-C_6$ alkynyl, $C_4-C_6$ cycloalkyl, $C_6-C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, and $PO_3R^4R^5$, wherein the alkyl, alkenyl, alkynyl, cycloalkyl, heterocycloalkyl, aryl, and heteroaryl are each optionally substituted by 1, 2, 3, or 4 independently selected $R^X$ groups; and each $R^X$ is independently selected from the group consisting of OH, SH, CN, $NO_2$, halo, pseudo-halo, amino, thionyl, sulfinyl, sulfonyl, sulfo, $C_1-C_4$ alkyl, $C_2-C_4$ alkenyl, $C_2-C_4$ alkynyl, $C_1-C_4$ haloalkyl, $C_1-C_4$ cyanoalkyl, $C_1-C_4$ hydroxyalkyl, $C_1-C_4$ alkoxy, $C_1-C_4$ aminoalkyl, di($C_1-C_4$ alkyl) amino, $C_1-C_4$ alkylamine, phosphinate, phosphinate ester, phosphonate, phosphonate ester, phosphodiester, $C_{1-4}$ alkylphosphodiester, $C_3-C_6$ cycloalkyl, phenyl, 5-6 membered heteroaryl, 5-6 membered heterocycloalkyl, and ($C_1-C_4$ alkyl) phenyl;

wherein if Q is CH or CCOOH and all Y are CH, then at least one of $R^2$ or $R^3$ is not H;

wherein if all $R^2$ and $R^3$ are H and at least one Y of Formula IV is not CH, then $R^1$ is not $C_2$ alkylene;

wherein each $D^1$ is independently bound to $(L^1)_b$-TBM via $R^2$, $R^3$, $R^4$, $R^5$, Z, or $R^X$; and wherein each $D^2$ is independently bound to $(L^2)_c$-TBM via $R^2$, $R^3$, $R^4$, $R^5$, Z, or $R^X$.

2. The compound of claim 1, wherein DG is:

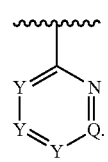

3. The compound of claim 1, wherein Q is CH.

4. The compound of claim 1, wherein Y is CH.

5. The compound of claim 1, wherein at least one Y is CZ, wherein Z is selected from the group consisting of $CO_2R^4$, $C_1-C_6$ alkyl, and $OR^4$.

6. The compound of claim 1, wherein one Y is CZ, wherein Z is selected from the group consisting of $CO_2R^4$, $C_1-C_6$ alkyl, and $OR^4$, and all other Y are CH.

7. The compound of claim 1, wherein each $R^4$ is H or $C_1-C_6$ alkyl, wherein the alkyl is optionally substituted by 1, 2, 3, or 4 OH groups.

8. The compound of claim 1, wherein $R^2$ and $R^3$ are each H.

9. The compound of claim 1, wherein $R^1$ is $C_3-C_{10}$ cycloalkylene.

10. The compound of a claim 1, wherein $R^1$ is a selected from the group consisting of:

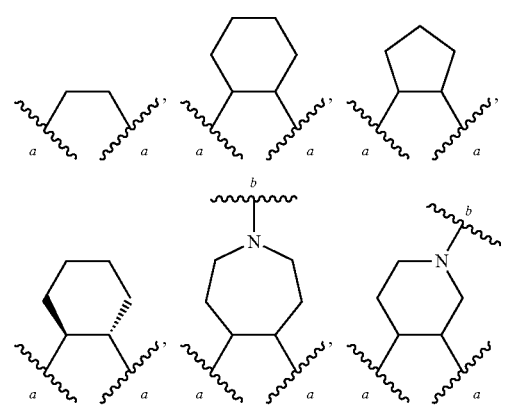

-continued

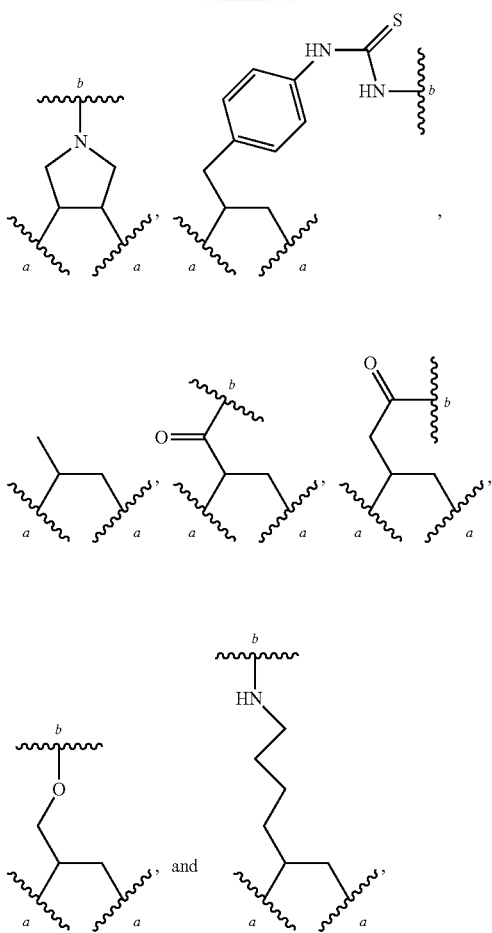

wherein "a" indicates the point of attachment of $R^1$ to each of the adjacent nitrogens and "b" indicates the point of attachment of $R^1$ to $(L^1)_b$-TBM or $(L^2)_c$-TBM.

11. The compound of any one claim 1, wherein $R^1$ is:

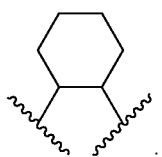 [SMILES: *C1CCCCC1*]

12. The compound of claim 1, wherein $R^1$ is a $C_2$-$C_6$ alkylene.

13. The compound of claim 1, wherein $R^1$ is:

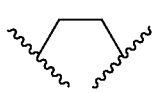

14. The compound of claim 1, wherein $R^2$ is H.
15. The compound of claim 1, wherein $R^3$ is H.
16. The compound of claim 1, wherein each $D^1$ and $D^2$ are independently selected from the group consisting of:

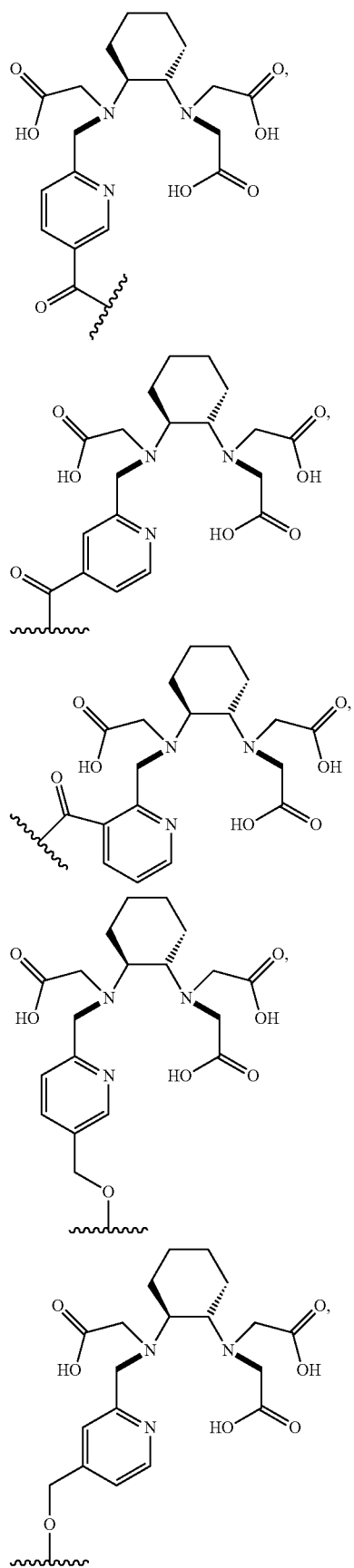

117
-continued
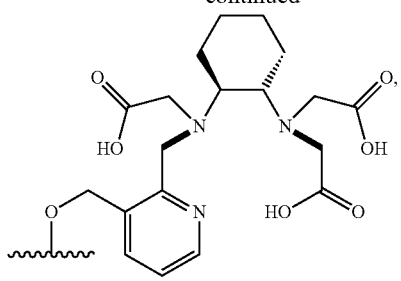
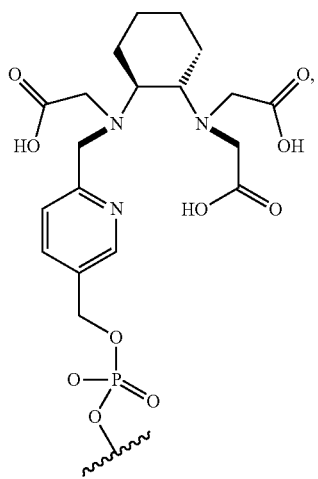
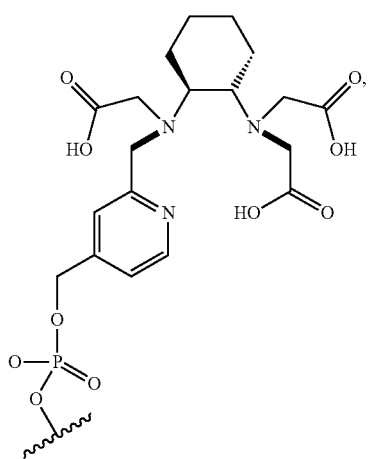
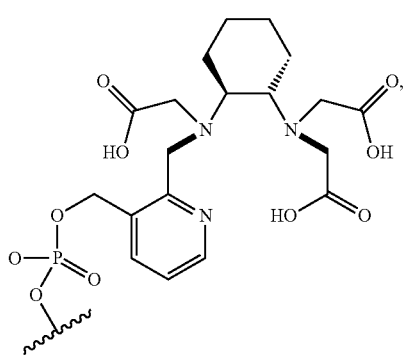
118
-continued
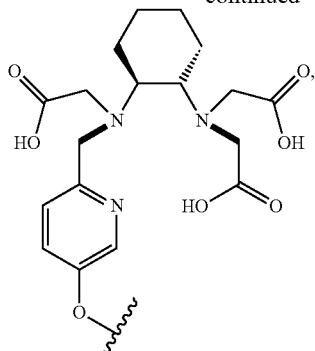
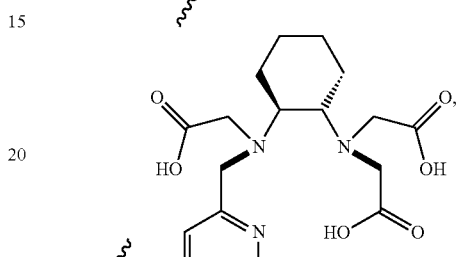
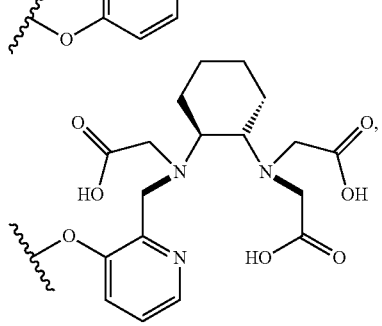
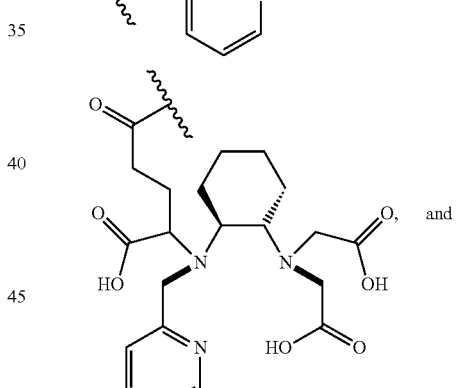
and
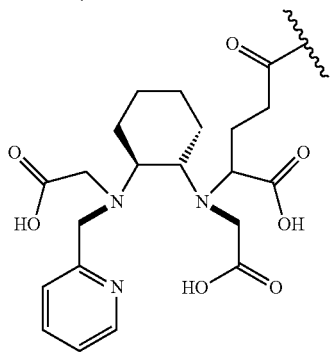
or a pharmaceutically acceptable salt thereof,
wherein ∼∼∼∼ indicates the point of attachment of $D^1$ to $(L^1)_b$-TBM or $D^2$ to $(L^2)_c$-TBM.

17. A compound of Formula (A):

$$(D^1)_a\text{-}(L^1)_b\text{-}TBM\text{-}(L^2)_c\text{-}(D^2)_d \quad (A)$$

or a pharmaceutically acceptable salt thereof, wherein:
TBM is a target binding moiety;
$L^1$ is a linker;
$L^2$ is a linker;
a is an integer from 0 to 4;
b is 0 or 1;
  wherein if a is 0, b is 0;
c is 0 or 1;
d is an integer from 0 to 4;
  wherein if d is 0, c is 0;
  wherein at least one of a and d is an integer from 1 to 4; and
each $D^1$ and $D^2$ are independently selected from a compound of Formula (XVII):

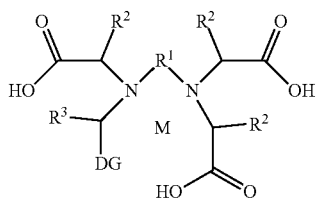

(XVII)

or a pharmaceutically acceptable salt thereof, wherein:
$R^1$ is selected from the group consisting of a $C_2$-$C_6$ alkylene, a $C_3$-$C_{10}$ cycloalkylene, 4-10 membered heterocycloalkylene, $C_6$-$C_{10}$ arylene, 5-10 membered heteroarylene, $(C_1$-$C_6)$dialkyl $(C_6$-$C_{10}$ arylene), and $(C_1$-$C_6)$dialkyl(5-10 membered heteroarylene), wherein the alkylene, cycloalkylene, heterocycloalkylene, arylene, and heteroarylene are each optionally substituted by 1, 2, 3, or 4 independently selected $R^X$ groups, and wherein $R^1$ is bound to the adjacent nitrogens via the 1,2 or 1,3 positions on $R^1$;
$R^2$ and $R^3$ are each independently selected from the group consisting of H, $CO_2H$, $(C_1$-$C_6$ alkyl) $CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, and $PO_3R^4R^5$;
$R^4$ and $R^5$ are each independently selected from the group consisting of H and $C_1$-$C_6$ alkyl, wherein the alkyl is optionally substituted by 1, 2, 3, or 4 independently selected $R^X$ groups:
DG is selected from the group consisting of:

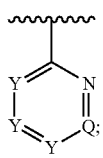

(II)

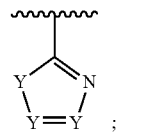

(III)

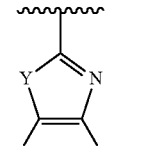

(IV)

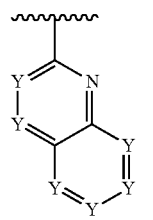

(V)

or any constitutional isomers of Formulas IV and V, wherein
each Y is independently CH, CZ, N, O, S, or $NR^4$:
Q is CH, CZ, N, O, S, or $NR^4$:
each Z is independently selected from the group consisting of H, OH, $OR^4$, $CO_2R$, —$(C_{1-6}$ alkyl)$CO_2H$, $C_1$-$C_6$ alkyl, $C_2$-$C_6$ alkenyl, $C_2$-$C_6$ alkynyl, $C_4$-$C_6$ cycloalkyl, $C_6$-$C_{10}$ aryl, 5-6 membered heterocyclyl, 5-6 membered heteroaryl, $C(O)NR^4R^5$, $CH_2NHCOR^4$, $C(O)N(OH)R^4$, $C(O)NHSO_2R^4$, $CH_2NHSO_2R^4$, $N(OH)C(O)R^4$, $P(R^4)O_2R^5$, and $PO_3R^4R^5$, wherein the alkyl, alkenyl, alkynyl, cycloalkyl, heterocycloalkyl, aryl, and heteroaryl are each optionally substituted by 1, 2, 3, or 4 independently selected $R^X$ groups;
each $R^X$ is independently selected from the group consisting of OH, SH, CN, $NO_2$, halo, pseudohalo, amino, thionyl, sulfinyl, sulfonyl, sulfo, $C_1$-$C_4$ alkyl, $C_2$-$C_4$ alkenyl, $C_2$-$C_4$ alkynyl, $C_1$-$C_4$ haloalkyl, $C_1$-$C_4$ cyanoalkyl, $C_1$-$C_4$ hydroxyalkyl, $C_1$-$C_4$ alkoxy, $C_1$-$C_4$ aminoalkyl, di($C_1$-$C_4$ alkyl) amino, $C_1$-$C_4$ alkylamine, phosphinate, phosphinate ester, phosphonate, phosphonate ester, phosphodiester, $C_{1-4}$ alkylphosphodiester, $C_3$-$C_6$ cycloalkyl, phenyl, 5-6 membered heteroaryl, 5-6 membered heterocycloalkyl, and $(C_1$-$C_4$ alkyl) phenyl; and
M is selected from the group consisting of Gd(III), Fe(III), Mn(II), Mn(III), Cr(III), Cu(II), Cu(III), Dy(III), Ho(III), Er(III), Pr(III), Eu(II), Eu(III), Nd(III), La(III), Lu(III), Sm(III), Tb(III), Tb(IV), Tm(III), Y(III), In(III), Ga(III), Tc(III), Tc(IV), Tc(V), Re(III), Re(IV), Re(V), Bi(III), and Yb(III);
wherein, if Q is CH or $CCO_2H$ and all Y are CH, then at least one of $R^2$ or $R^3$ is not H;
wherein if all $R^2$ and $R^3$ are H and at least one Y of Formula IV is not CH, then $R^1$ is not $C_2$ alkylene;
wherein each $D^1$ is independently bound to $(L^1)_b$-TBM via $R^2$, $R^3$, $R^4$, $R^5$, Z, or $R^X$; and
wherein each $D^2$ is independently bound to $(L^2)_c$-TBM via $R^2$, $R^3$, $R^4$, $R^5$, Z, or $R^X$.

18. The compound of claim 17, wherein TBM is:

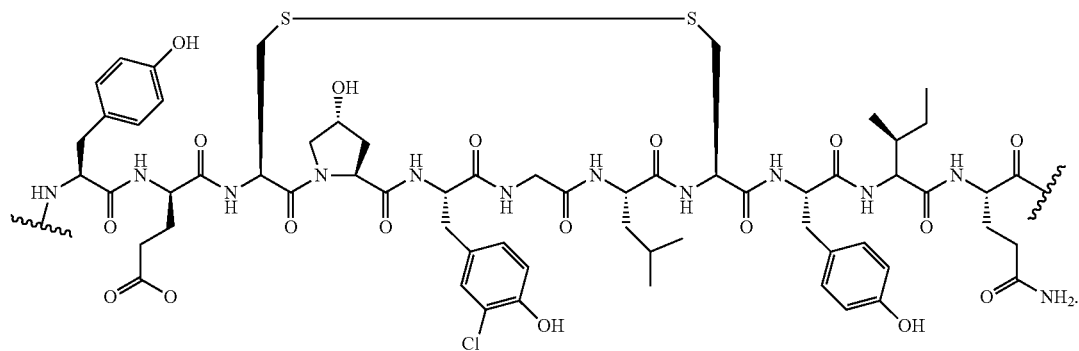 [SMILES: *N[C@@H](Cc1ccc(O)cc1)C(=O)N[C@H](CCC(=O)O)C(=O)N[C@H]1CSSC[C@@H](C(=O)N[C@@H](Cc2ccc(O)cc2)C(=O)NC(C(=O)N[C@@H](CCC(N)=O)C(*)=O)[C@@H](C)CC)NC(=O)[C@H](CC(C)C)NC(=O)CNC(=O)[C@H](Cc2ccc(O)c(Cl)c2)NC(=O)[C@@H]2C[C@@H](O)CN2C1=O]

19. The compound of claim 17, wherein TBM is:

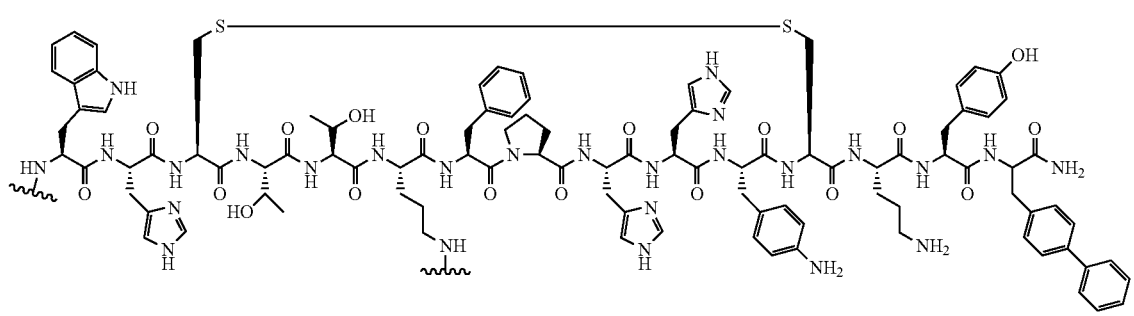

20. The compound of claim 17, wherein for each $D^1$ and $D^2$, $R^1$ is 1,2-cyclohexylene, $R^2$ is H, $R^3$ is H, DG is Formula II, Q is CH, the Y positioned α- to Q is $(L^1)_b$-TBM or C-$(L^2)_c$-TBM, and all other Y are CH, and $L^1$ and $L^2$ are each —C(O)—.

21. The compound of claim 17, wherein the compound is selected from the group consisting of:

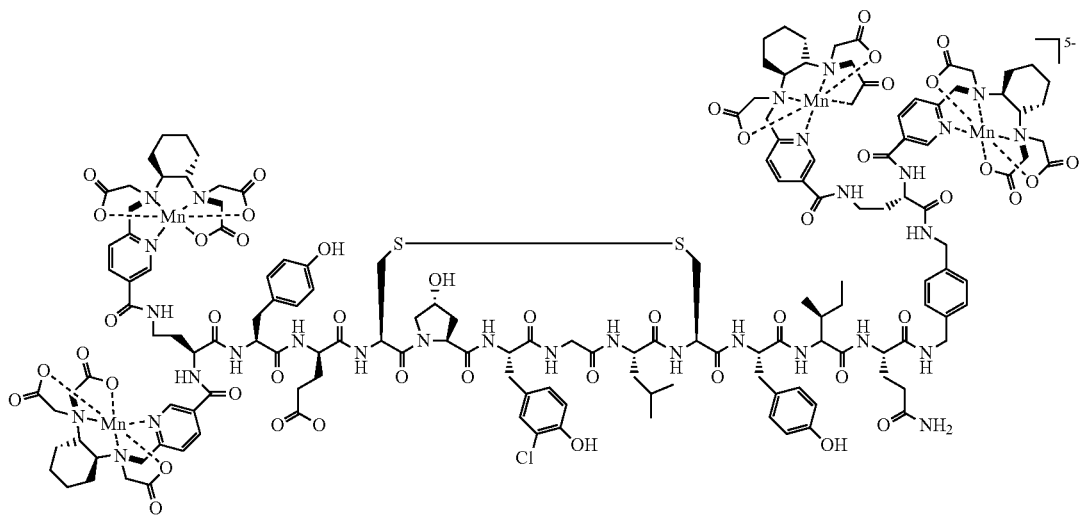

and

-continued

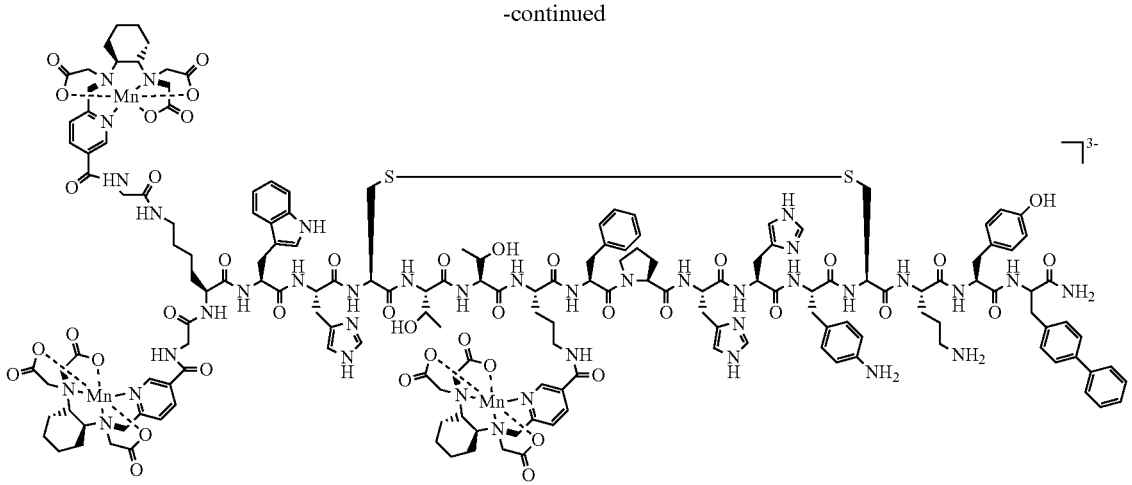

22. A method of magnetic resonance (MR) imaging a patient, the method comprising:
   a) administering to the patient an effective amount of a compound of claim 17; and
   b) acquiring an MR image of the patient.

23. The compound of claim 17, wherein DG is:

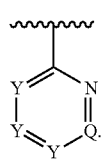

(II)

24. The compound of claim 17, wherein Q is CH.
25. The compound of claim 17, wherein Y is CH.
26. The compound of claim 17, wherein at least one Y is CZ, wherein Z is selected from the group consisting of $CO_2R^4$, $C_1$-$C_6$ alkyl, and $OR^4$.
27. The compound of claim 17, wherein one Y is CZ, wherein Z is selected from the group consisting of $CO_2R^4$, $C_1$-$C_6$ alkyl, and $OR^4$, and all other Y are CH.
28. The compound of claim 17, wherein each $R^4$ is H or $C_1$-$C_6$ alkyl, wherein the alkyl is optionally substituted by 1, 2, 3, or 4 OH groups.
29. The compound of claim 17, wherein $R^2$ and $R^3$ are each H.
30. The compound of claim 17, wherein $R^1$ is $C_3$-$C_{10}$ cycloalkylene.
31. The compound of claim 17, wherein $R^1$ is selected from the group consisting of:

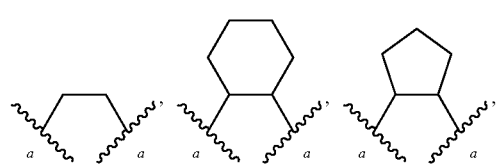

-continued

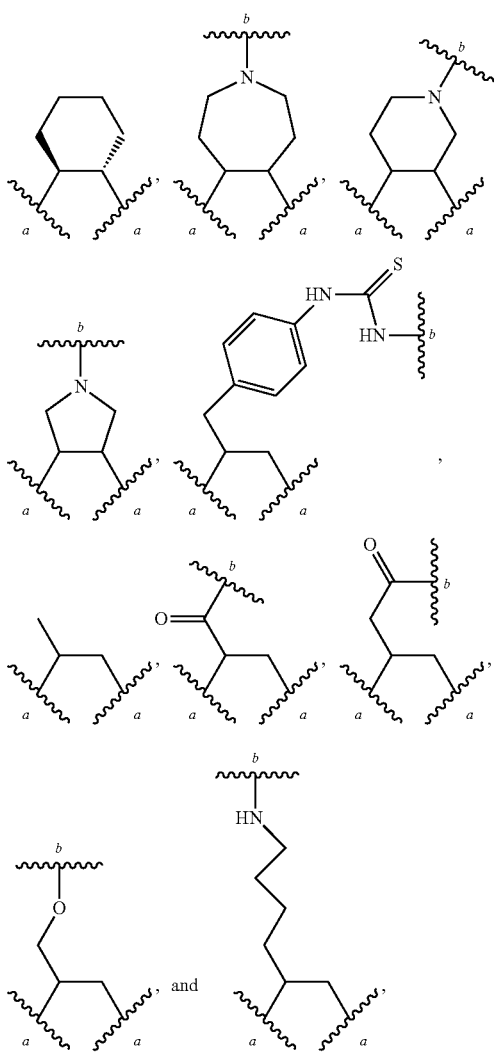

wherein "a" indicates the point of attachment of $R^1$ to each of the adjacent nitrogens and "b" indicates the point of attachment of $R^1$ to $(L^1)_b$-TBM or $(L^2)_c$-TBM.

32. The compound of claim 17, wherein R¹ is:
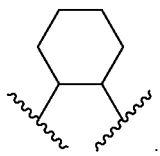 [SMILES: *C1CCCCC1*]
33. The compound of claim 17, wherein R¹ is a $C_2$-$C_6$ alkylene.
34. The compound of claim 17, wherein R¹ is:
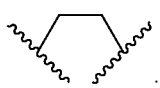 [SMILES: *CC*]
35. The compound of claim 17, wherein R² is H.
36. The compound of claim 17, wherein R³ is H.
37. The compound of claim 17, wherein each D¹ and D² are independently selected from the group consisting of:
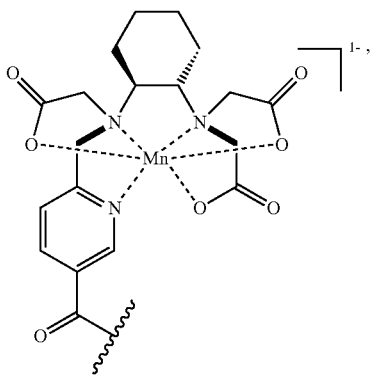
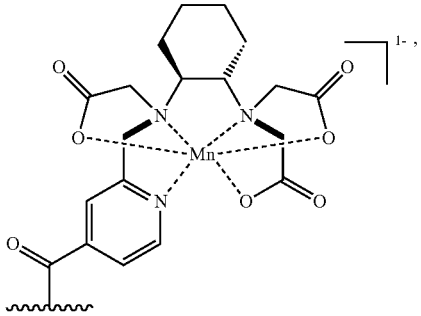
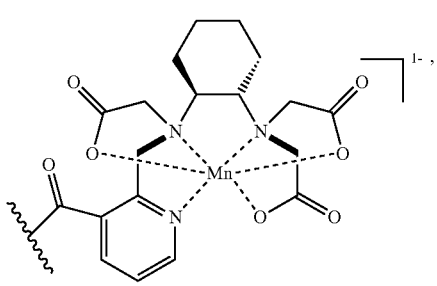
-continued
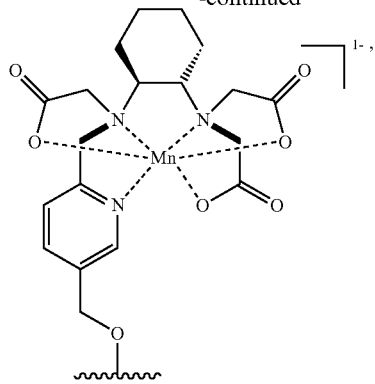
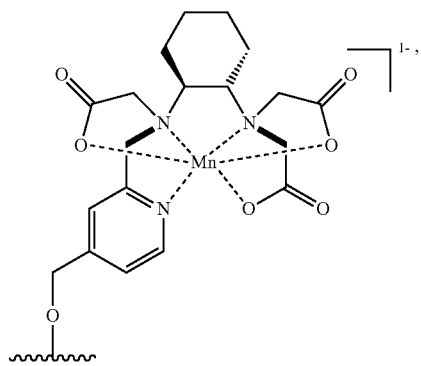
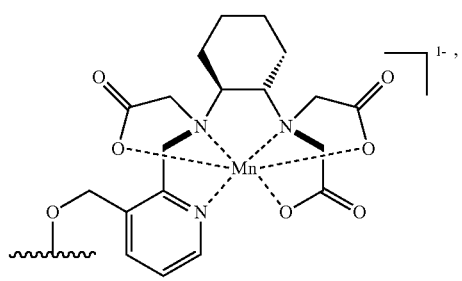
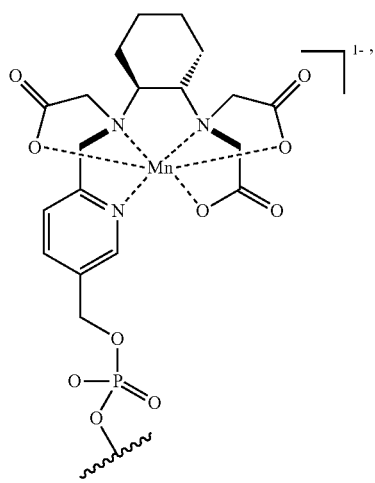

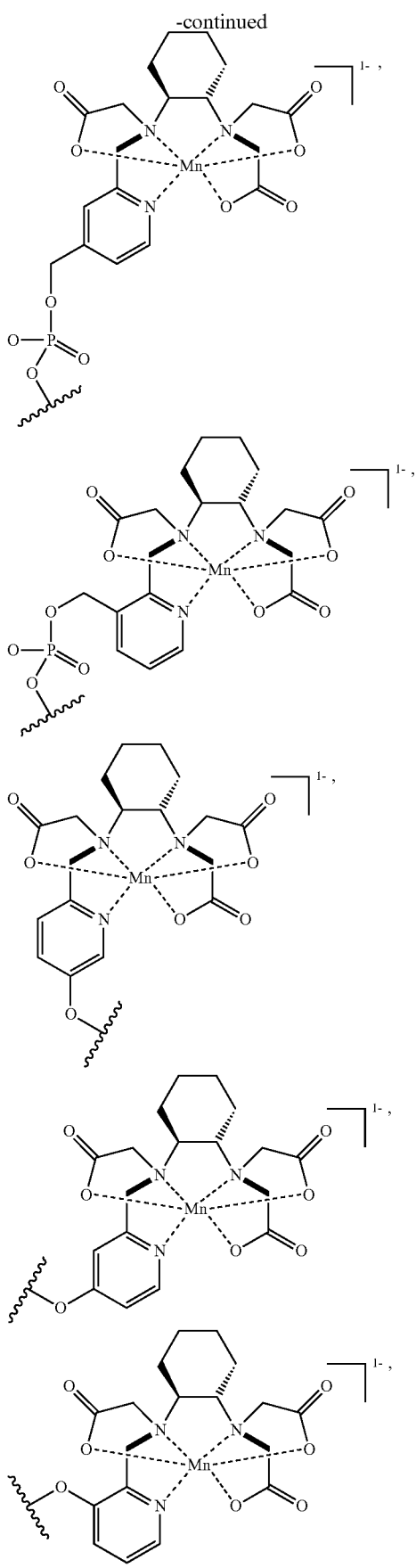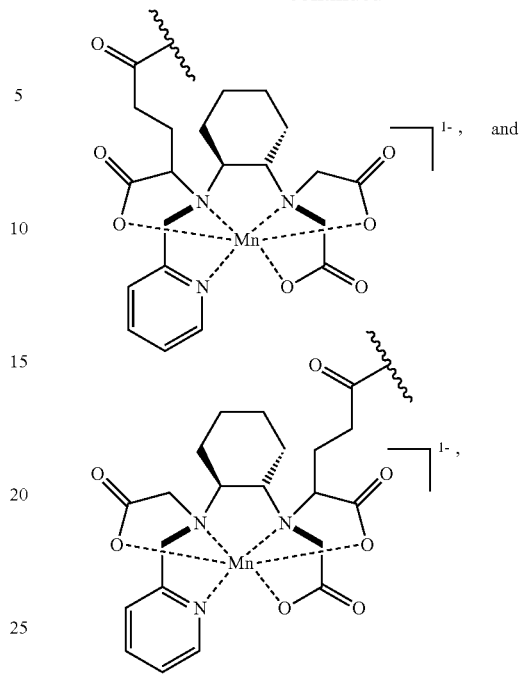
wherein ~~~ indicates the point of attachment of $D^1$ to $(L^1)_b$-TBM or $D^2$ to $(L^2)_c$-TBM.
38. The compound of claim 17, wherein c and d are each 0 and TBM is selected from the group consisting of:
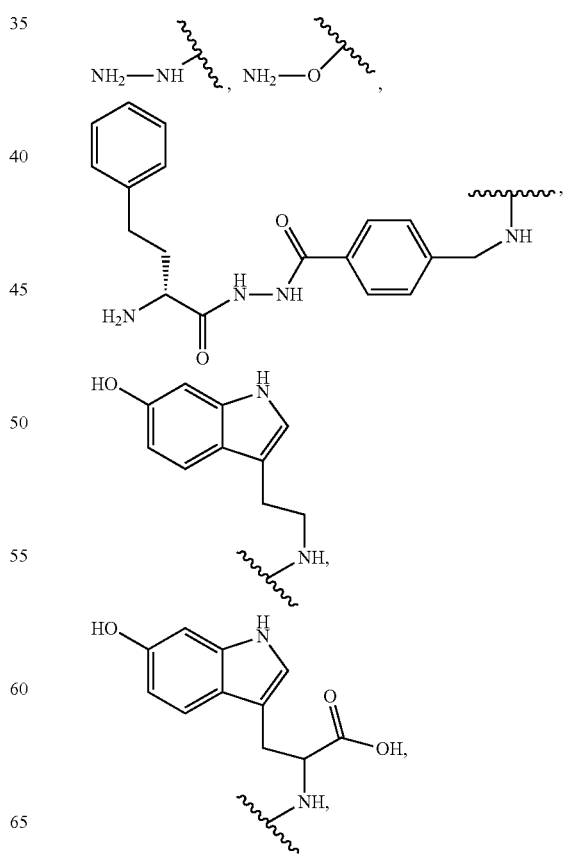

-continued

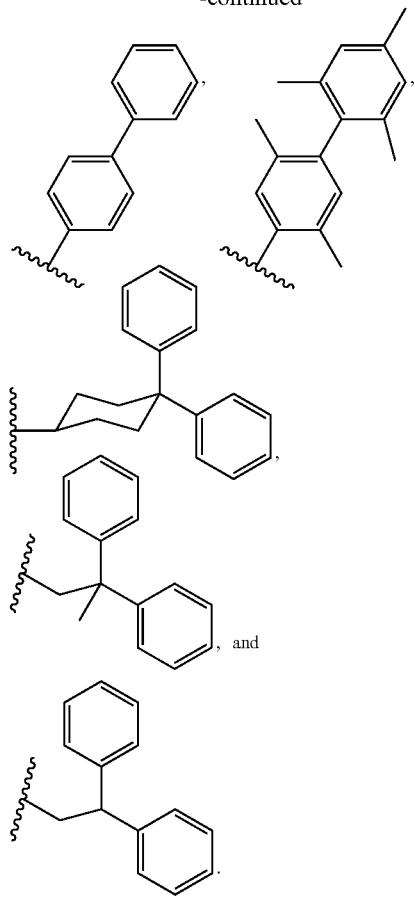

39. The compound of claim 18, wherein for each $D^1$ and $D^2$:

DG is Formula II;

Q is CH;

for each $D^1$, the Y positioned α-, β-, or γ- to Q are each independently selected from the group consisting of C—C(O)—$(L^1)_b$, C—NH-$(L^1)_b$, and C—O-$(L^1)_b$;

for each $D^2$, the Y positioned α-, β-, or γ- to Q are each independently selected from the group consisting of C—C(O)—$(L^2)_c$, C—NH-$(L^2)_c$, and C—O-$(L^2)_c$;

$(L^1)_b$ and $(L^2)_c$ are each independently selected from the group consisting of C(O), $R^X$, C(O)—$R^X$, C(O)—$R^X$—C(O), NH—$R^X$, NH—$R^X$—NH, and C(O)C(NH)—$CH_2CH_2$—NH; and $R^X$ is $C_1$-$C_6$ alkyl.

40. The compound of claim 19, wherein for each $D^1$ and $D^2$:

DG is Formula II;

Q is CH;

for each $D^1$, the Y positioned α-, β-, or γ- to Q are each independently selected from the group consisting of C—C(O)—$(L^1)_b$, C—NH-$(L^1)_b$, and C—O-$(L^1)_b$;

for each $D^2$, the Y positioned α-, β-, or γ- to Q are each independently selected from the group consisting of C—C(O)—$(L^2)_c$, C—NH-$(L^2)_c$, and C—O-$(L^2)_c$;

$(L^1)_b$ and $(L^2)_c$ are each independently selected from the group consisting of C(O), $R^X$, C(O)—$R^X$, C(O)—$R^X$—C(O), NH—$R^X$, NH—$R^X$—NH, and C(O)C(NH)—$CH_2CH_2$—NH; and $R^X$ is $C_1$-$C_6$ alkyl.

41. The compound of claim 1, wherein TBM is:

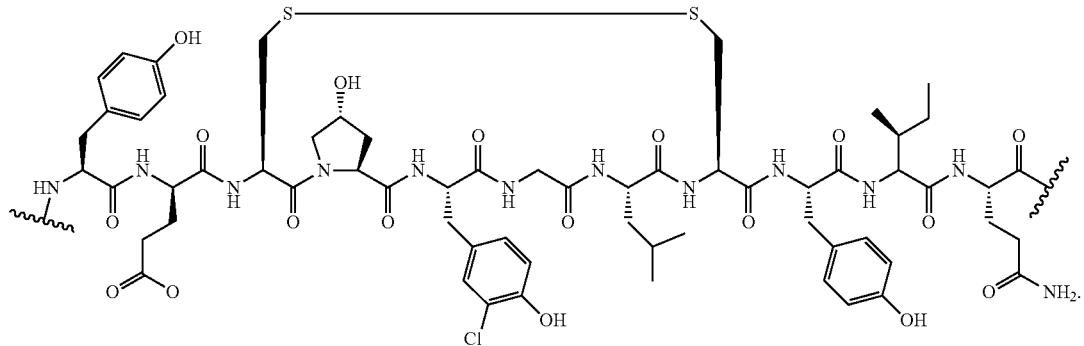 [SMILES: *N[C@@H](Cc1ccc(O)cc1)C(=O)N[C@H](CCC(=O)O)C(=O)N[C@H]1CSSC[C@@H](C(=O)N[C@@H](Cc2ccc(O)cc2)C(=O)NC(C(=O)N[C@@H](CCC(N)=O)C(*)=O)[C@@H](C)CC)NC(=O)[C@H](CC(C)C)NC(=O)CNC(=O)[C@H](Cc2ccc(O)c(Cl)c2)NC(=O)[C@@H]2C[C@@H](O)CN2C1=O]

42. The compound of claim 1, wherein TBM is:

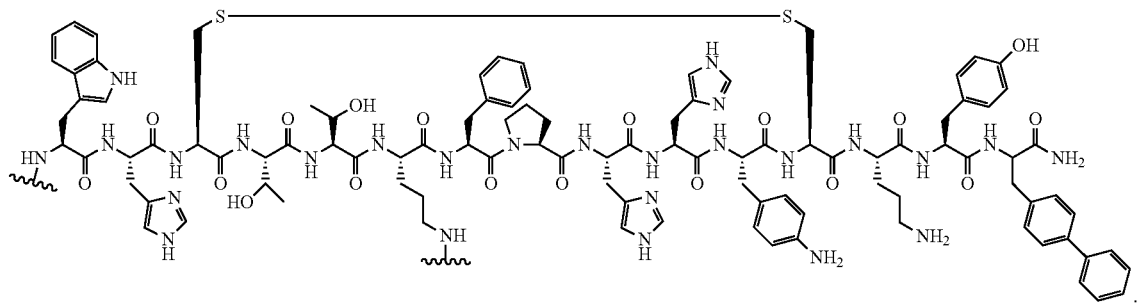 [SMILES: *NCCC[C@@H]1NC(=O)[C@H](C(C)O)NC(=O)[C@H](C(C)O)NC(=O)[C@@H](NC(=O)[C@H](Cc2c[nH]cn2)NC(=O)[C@H](Cc2c[nH]c3ccccc23)N*)CSSC[C@@H](C(=O)N[C@@H](CCCN)C(=O)N[C@@H](Cc2ccc(O)cc2)C(=O)NC(Cc2ccc(-c3ccccc3)cc2)C(N)=O)NC(=O)[C@H](Cc2ccc(N)cc2)NC(=O)[C@H](Cc2c[nH]cn2)NC(=O)[C@H](Cc2c[nH]cn2)NC(=O)[C@@H]2CCCN2C(=O)[C@H](Cc2ccccc2)NC1=O]

43. The compound of claim 1, wherein c and d are each 0 and TBM is selected from the group consisting of:

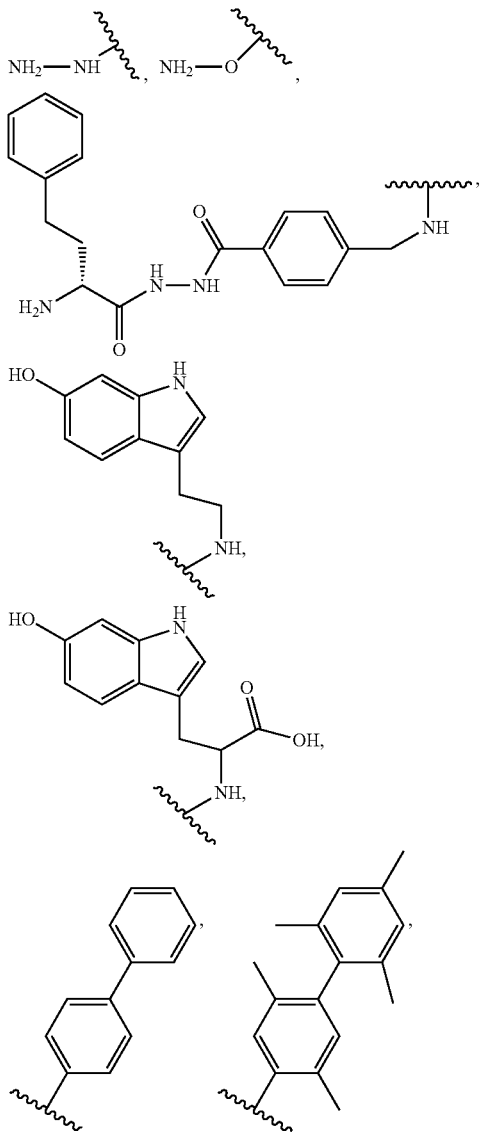

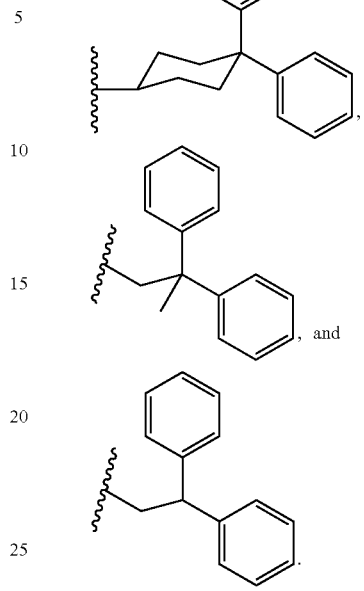

44. The compound of claim 43, wherein:
c and d are each 0;
DG is Formula II;
Q is CH;
the Y positioned α-, β-, or γ- to Q are each independently selected from the group consisting of C—C(O)—$(L^1)_b$, C—NH-$(L^1)_b$, and C—O-$(L^1)_b$;
$(L^1)_b$ is selected from the group consisting of C(O), $R^X$, C(O)—$R^X$, C(O)—$R^X$-C(O), NH-$R^X$, NH—$R^X$—NH, and C(O)C(NH)—$CH_2CH_2$—NH; and
$R^X$ is $C_1$-$C_6$ alkyl.

45. The compound of claim 1, wherein for each $D^1$ and $D^2$, $R^1$ is 1,2-cyclohexylene, $R^2$ is H, $R^3$ is H, DG is Formula II, Q is CH, the Y positioned α- to Q is C-$(L^1)_b$-TBM or C-$(L^2)_c$-TBM, and all other Y are CH, and $L^1$ and $L^2$ are each —C(O)—.

* * * * *

UNITED STATES PATENT AND TRADEMARK OFFICE
CERTIFICATE OF CORRECTION

PATENT NO. : 11,400,171 B2
APPLICATION NO. : 16/990368
DATED : August 2, 2022
INVENTOR(S) : Eric M. Gale and Peter Caravan It is certified that error appears in the above-identified patent and that said Letters Patent is hereby corrected as shown below:

In the Claims

In Column 111, Line 54 (approx.), Claim 1, delete "moiety:" and insert -- moiety; --

In Column 111, Line 55 (approx.), Claim 1, delete "linker:" and insert -- linker; --

In Column 111, Line 56 (approx.), Claim 1, delete "linker:" and insert -- linker; --

In Column 111, Line 57 (approx.), Claim 1, delete "4:" and insert -- 4; --

In Column 111, Line 58 (approx.), Claim 1, delete "1:" and insert -- 1; --

In Column 111, Line 59 (approx.), Claim 1, delete "0:" and insert -- 0; --

In Column 111, Line 60 (approx.), Claim 1, delete "1:" and insert -- 1; --

In Column 111, Line 61 (approx.), Claim 1, delete "4:" and insert -- 4; --

In Column 111, Line 62 (approx.), Claim 1, delete "0:" and insert -- 0; --

In Column 112, Line 63 (approx.), Claim 1, delete "dialkyl)" and insert -- dialkyl --

In Column 114, Line 48, Claim 10, after "of" delete "a"

In Column 114, Line 48, Claim 10, after "is" delete "a"

In Column 115, Line 42, Claim 11, after "of" delete "any one"

In Column 119, Line 57, Claim 17, delete "groups:" and insert -- groups; --

Signed and Sealed this
Thirty-first Day of January, 2023

*Katherine Kelly Vidal*

Katherine Kelly Vidal
*Director of the United States Patent and Trademark Office*

CERTIFICATE OF CORRECTION (continued)
U.S. Pat. No. 11,400,171 B2

In Column 120, Line 28, Claim 17, delete "NR⁴:" and insert -- NR⁴; --

In Column 120, Line 29, Claim 17, delete "NR⁴:" and insert -- NR⁴; --

In Columns 121-122, Line 4 (approx.), Claim 19, delete

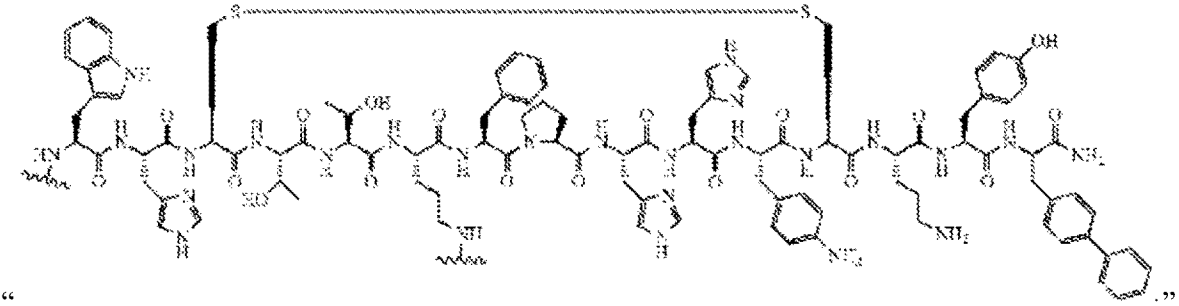

"  ,"

and insert

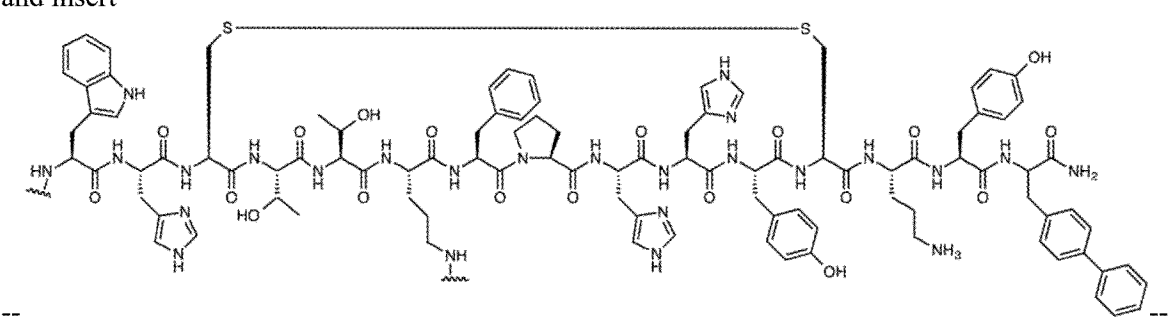

--  --

In Column 121, Line 41, Claim 20, delete "(L¹)ᵦ-TBM" and insert -- C-(L¹)ᵦ-TBM --

In Columns 123-124, Lines 1-22 (approx.), Claim 21, delete

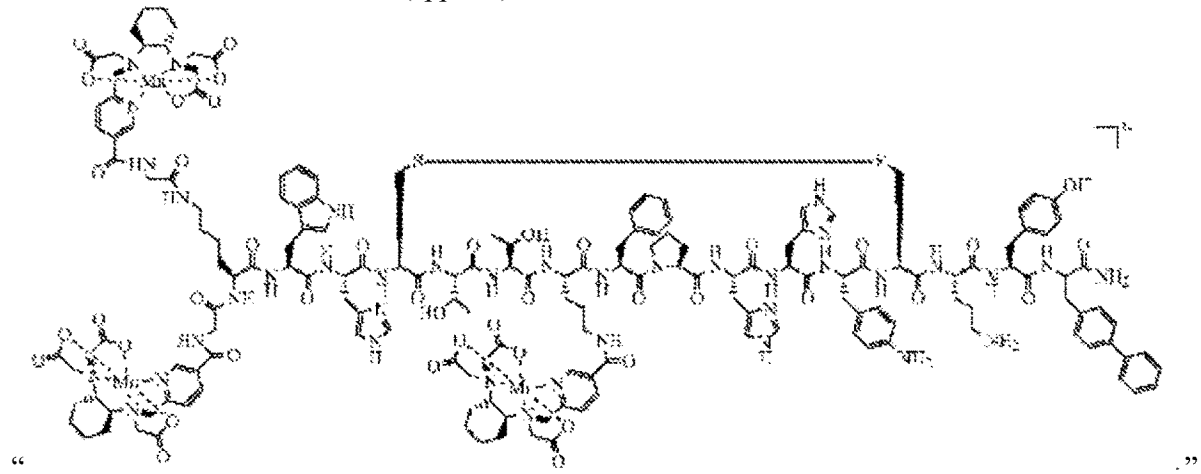

"  ,"

and insert

CERTIFICATE OF CORRECTION (continued)
U.S. Pat. No. 11,400,171 B2

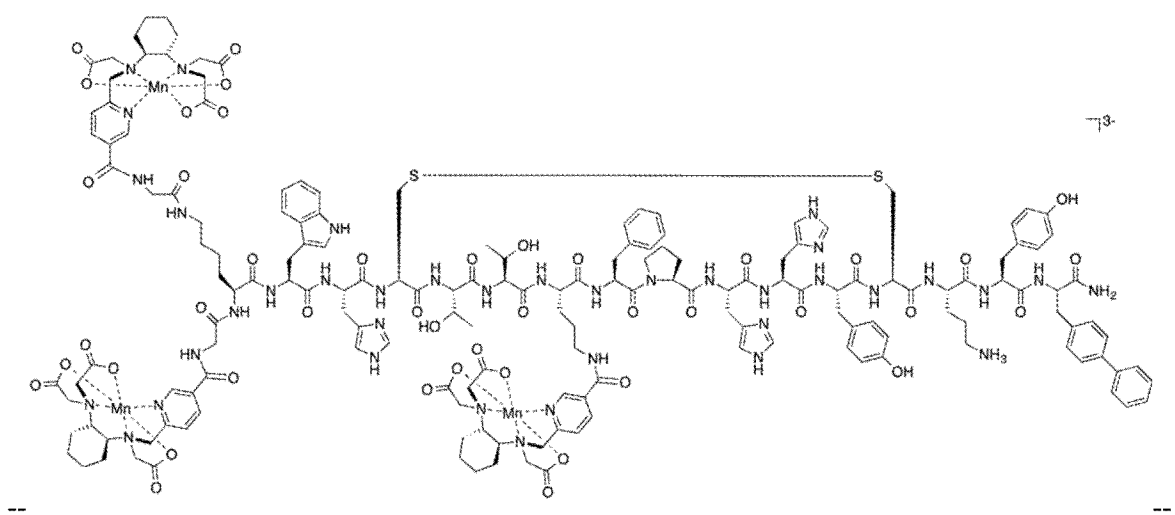

--   --

In Columns 129-130, Line 39 (approx.), Claim 42, delete

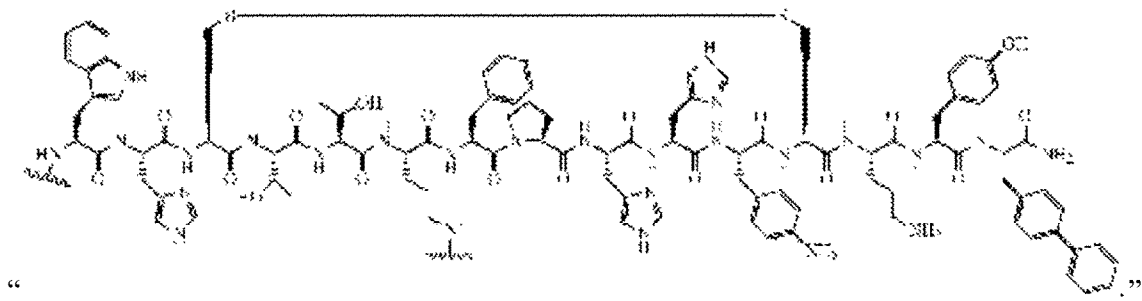

" "

and insert

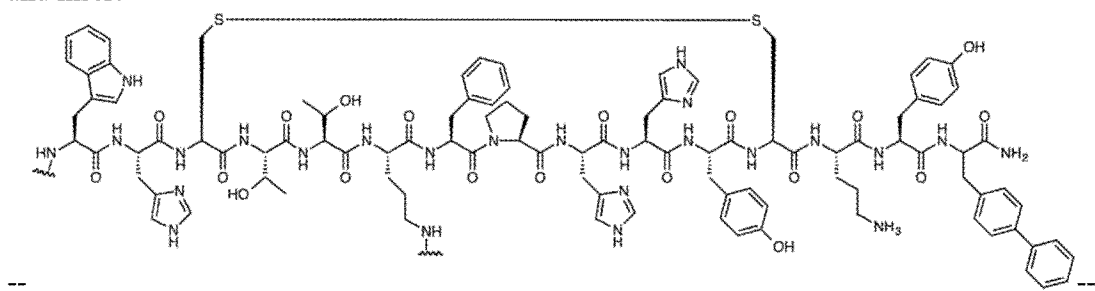

--   --